US012247977B2

(12) United States Patent
Burke et al.

(10) Patent No.: US 12,247,977 B2
(45) Date of Patent: Mar. 11, 2025

(54) NASOPHARYNGEAL PROTEIN BIOMARKERS OF ACUTE RESPIRATORY VIRUS INFECTION AND METHODS OF USING SAME

(71) Applicant: Duke University, Durham, NC (US)

(72) Inventors: Thomas W. Burke, Durham, NC (US); Ricardo Henao Giraldo, Durham, NC (US); Erik Soderblom, Raleigh, NC (US); Joseph Lucas, Chapel Hill, NC (US); Christopher W. Woods, Durham, NC (US); Geoffrey S. Ginsburg, Durham, NC (US)

(73) Assignee: Duke University, Durham, NC (US)

(*) Notice: Subject to any disclaimer, the term of this patent is extended or adjusted under 35 U.S.C. 154(b) by 1181 days.

(21) Appl. No.: 16/483,113

(22) PCT Filed: Feb. 2, 2018

(86) PCT No.: PCT/US2018/016611
§ 371 (c)(1),
(2) Date: Aug. 2, 2019

(87) PCT Pub. No.: WO2018/144834
PCT Pub. Date: Aug. 9, 2018

(65) Prior Publication Data
US 2019/0376969 A1    Dec. 12, 2019

Related U.S. Application Data

(60) Provisional application No. 62/454,260, filed on Feb. 3, 2017.

(51) Int. Cl.
G01N 33/569      (2006.01)
C07K 14/005     (2006.01)
G01N 33/577     (2006.01)

(52) U.S. Cl.
CPC ..... G01N 33/56983 (2013.01); C07K 14/005 (2013.01); G01N 33/577 (2013.01); G01N 2333/005 (2013.01); G01N 2469/10 (2013.01)

(58) Field of Classification Search
None
See application file for complete search history.

(56) References Cited

U.S. PATENT DOCUMENTS 8,821,876 B2 * 9/2014 Ginsburg ............. C12Q 1/6883
                                                    424/147.1
2005/0209785 A1 * 9/2005 Wells ..................... G16B 40/30
                                                    702/19

FOREIGN PATENT DOCUMENTS

WO    WO-2015048098 A1 * 4/2015 ............ A61K 31/00
WO    2016/185385         11/2016
WO    2017/004390         1/2017

OTHER PUBLICATIONS

Weisshaar et al. DNA Cell Biol; 34(8):505-10) (Year: 2015).*
Woods A Host Transcriptional Signature for Presymptomatic Detection of Infection in Humans Exposed to Influenza H1N1 or H3N2. PLoS ONE 8(1): e52198. (Year: 2013).*
International Search Report and Written Opinion corresponding to International Application No. PCT/US2018/016611, mailed Apr. 19, 2018 (13 pages).
World Health Organization. "Global Action Plan on Antimicrobial Resistance", S Afr Med J., 105(5), 2015, 325.
Addona, Terri A., et al., "Multi-site assessment of the precision and reproducibility of multiple reaction monitoring-based measurements of proteins in plasma", Nature Biotechnology, 27, 2009, 633-641.
Aebersold, Ruedi, et al., "Western Blots versus Selected Reaction Monitoring Assays: Time to Turn the Tables?", Molecular & Cellular Proteomics, 12 (9), 2013, 2381-2382.
Bhoj, Vijay G., et al., PNAS, 105(37), 2008, 14046-14051.
Boja, Emily S., et al., "The path to clinical proteomics research: integration of proteomics, genomics, clinical laboratory and regulatory science", Korean J Lab Med., 31(2), 2011, 61-71.
Byington, Carrie L., et al., "Community Surveillance of Respiratory Viruses Among Families in the Utah Better Identification of Germs-Longitudinal Viral Epidemiology (BIG-LOVE) Study", Clinical Infectious Diseases, 61(8), 2015, 1217-1224.
Cameron, Cheryl M., et al., "Gene Expression Analysis of Host Innate Immune Responses during Lethal H5N1 Infection in Ferrets", Journal of Virology, 82(22), 2008, 11308-11317.
Cameron, Mark J., et al., "Interferon-Mediated Immunopathological Events Are Associated with Atypical Innate and Adaptive Immune Responses in Patients with Severe Acute Respiratory Syndrome", Journal of Virology, 81(16), 2007, 8692-8706.
Fawcett, Tom, "An Introduction to ROC Analysis", Pattern Recognition Letters, 27, 2006, 861-874.
Friedman, Jerome, et al., "Regularization Paths for Gneralized Linear Models via Coordinate Descent", J Stat Softw., 33(1), 2010, 1-22.
Gaboriaud, Christine, et al., "Structure and activation of the C1 complex of complement: unraveling the puzzle", Trends in Immunology, 25(7), 2004, 368-373.
Gersten, Robert E., et al., "Integration of proteomic-based tools for improved biomarkers of myocardial injury", Clinical Chemistry, 56(2), 2010, 194-201.
Hersh, Adam L., et al., "Antibiotic Prescribing in Ambulatory Pediatrics in the United States", Pediatrics, 128 (6), 2011, 1053-1061.

(Continued)

Primary Examiner — Shanon A. Foley
Assistant Examiner — Myron G Hill
(74) Attorney, Agent, or Firm — Myers Bigel, P.A.

(57) ABSTRACT

The present disclosure provides methods for determining the presence or absence of and/or the etiology of an acute respiratory viral infection in a subject, as well as methods of treating the subject based on the determination, by measuring on a platform the expression levels of a pre-defined set of gene products.

20 Claims, 8 Drawing Sheets
Specification includes a Sequence Listing.

(56) References Cited

OTHER PUBLICATIONS

Hong, Ching-Ye, et al., "Acute respiratory symptoms in adults in general practice", Family Practice, (21(3), 2004, 317-323.
House, W., "National strategy for combating antibiotic-resistant bacteria", The White House-Office of the Press Secretary, 2014.
Huang, Da Wei, et al., "Bioinformatics enrichment tools: paths toward the comprehensive functional analysis of large gene lists", Nucleic Acids Research, 37(1), 2009, 1-13.
Huang, Yongsheng, et al., "Temporal Dynamics of Host Molecular Responses Differentiate Symptomatic and Asymptomatic Influenza A Infection", PLoS Genetics, 7(8), 2011, e1002234.
Jackson, George Gee, et al., "Transmission of the Common COld to Volunteers Under Controlled Conditions. IV. Specific Immunity to the Common Cold", AMA Arch Intern Med, 101(2), 1958, 762-769.
Johnston, S. L., et al., "Use of polymerase chain reaction for diagnosis of picornavirus infection in subjects with and without respiratory symptoms", J Clin Microbiology, 31(1), 1993, 111-117.
Johnstone, Jennie, et al., "Viral Infection in Adults Hospitalized With Community-Acquired Pneumonia: Prevalence, Pathogens, and Presentation", CHEST, 134(6), 2008, 1141-1148.
Kimura, Hirokazu, et al., "Cytokine production and signaling pathways in respiratory virus infection", Front. Microbiol., 4(276), 2013, 1-9.
Kiyonami, Reiko, et al., "Increased selectivity, analytical precision, and throughput in targeted proteomics", Molecular & Cellular Proteomics, 10(2), 2011, M110 002931.
Koyama, Shohei, et al., "Innate immune response to viral infection", Cytokine, 43(3), 2008, 336-341.
Liu, Tzu-Yu, et al., "An individualized predictor of health and disease using paired reference and target samples", BMC Bioinformatics, 17(1), 2016, 1-15.
Marion, Tony, et al., "Respiratory Mucosal Proteome Quantification in Human Influenza Infections", PLoS One, 11 (4), 2016, 1-16, e0153674.
Mccaig, Linda F., et al., "Trends in antimicrobial drug prescribing among office-based physicians in the United States", JAMA, 273(3), 1995, 214-219.
Mcclain, Micah T., et al., "A Genomic Signature of Influenza Infection Shows Potential for Presymptomatic Detection, Guiding Early Therapy, and Monitoring Clinical Responses", Open Forum Infectious Diseases, 3(1), 2016, 1-4.
O'Neill, J, "Rapid Diagnostics: Stopping Unnecessary Use of Antibiotics", 2015.
Oshansky, Christine M., et al., "Mucosal immune responses predict clinical outcomes during influenza infection independently of age and viral load", Am J Respir Crit Care Med., 189(4), 2014, 449-462.
Pirillo, Angela, et al., "HDL in infectious diseases and sepsis", Handb Exp Pharmacol, 224, 2015, 473-498.
Ramilo, Octavio, et al., "Gene expression patterns in blood leukocytes discriminate patients with acute infections", Blood, 109(5), 2007, 2066-2077.
Ramilo, Octavio, et al., "Shifting the paradigm: host gene signatures for diagnosis of infectious diseases", Cell Host & Microbe, 6(3), 2009, 199-200.
Ricklin, Daniel, et al., "Complement: a key system for immune surveillance and homeostasis", Nat Immunol., 11(9), 2010, 785-797.
Thompson, M. G., et al., "Estimates of deaths associated with seasonal influenza-United States, 1976-2007", Morbidity and Mortality Weekly Report, 59(33), 2010, 1057-1062.
Tsalik, Ephraim L., et al., "Host gene expression classifiers diagnose acute respiratory illness etiology", Sci Transl Med., 8(322), 2016, 1-22.
Woods, Christopher W., et al., "A host transcriptional signature for presymptomatic detection of infection in humans exposed to influenza H1N1 or H3N2", PLoS, 8(1), e52198, 2013, 1-9.
Yoneyama, Mitsutoshi, et al., "Recognition of viral nucleic acids in innate immunity", Rev Med Virol, 20(1), 2010, 4-22.
Zaas, Aimee K., et al., "A Host-Based RT-PCR Gene Expression Signature to Identify Acute Respiratory Viral Infection", Science Translational Medicine, 5(203), 203ra126, 2013, 1-19.
Zaas, Aimee K., et al., "Gene expression signatures diagnose influenza and other symptomatic respiratory viral infections in humans", Cell Host Microbe, 6(3), 2009, 207-217.
Zaas, Aimee K., et al., "The current epidemiology and clinical decisions surrounding acute respiratory infections", Trends Mol Med, 20(10), 2014, 579-588.
Manabe, Toshie, et al., "Favipiravir for the treatment of patients with COVID-19: a systematic review and meta-analysis", BMC Infectious Diseases 21:489, 2021.
Mir, Wasey Ali Yadullahi, et al., "Successful Treatment of Respiratory Syncytial Virus Infection in an Immunocompromised Patient With Ribavirin", Cureus 13(8):e16930, 2021.

* cited by examiner

POOLED DISCOVERY DATASET

CFAB

TIG1

TBA1B

STAT

SEQUENCE LISTING

<160> NUMBER OF SEQ ID NOS: 56

<210> SEQ ID NO 1
<211> LENGTH: 9

```
<212> TYPE: PRT
<213> ORGANISM: Artificial
<220> FEATURE:
<223> OTHER INFORMATION: peptide

<400> SEQUENCE: 1

Ala Asn Glu Leu Leu Ile Asn Val Lys
1               5

<210> SEQ ID NO 2
<211> LENGTH: 8
<212> TYPE: PRT
<213> ORGANISM: Artificial
<220> FEATURE:
<223> OTHER INFORMATION: peptide

<400> SEQUENCE: 2

Ile Gly Asp Tyr Ala Gly Ile Lys
1               5

<210> SEQ ID NO 3
<211> LENGTH: 10
<212> TYPE: PRT
<213> ORGANISM: Artificial
<220> FEATURE:
<223> OTHER INFORMATION: peptide

<400> SEQUENCE: 3

Val Leu Gly Ile Asp Gly Gly Glu Gly Lys
1               5                   10

<210> SEQ ID NO 4
<211> LENGTH: 8
<212> TYPE: PRT
<213> ORGANISM: Artificial
<220> FEATURE:
<223> OTHER INFORMATION: peptide

<400> SEQUENCE: 4

Glu Ala Leu Asp Phe Phe Ala Arg
1               5

<210> SEQ ID NO 5
<211> LENGTH: 13
<212> TYPE: PRT
<213> ORGANISM: Artificial
<220> FEATURE:
<223> OTHER INFORMATION: peptide

<400> SEQUENCE: 5

Val Val Gly Leu Ser Thr Leu Pro Glu Ile Tyr Glu Lys
1               5                   10

<210> SEQ ID NO 6
<211> LENGTH: 14
<212> TYPE: PRT
<213> ORGANISM: Artificial
<220> FEATURE:
<223> OTHER INFORMATION: peptide

<400> SEQUENCE: 6

Glu Gln Leu Gly Glu Phe Tyr Glu Ala Leu Asp Cys Leu Arg
1               5                   10

<210> SEQ ID NO 7
<211> LENGTH: 9
<212> TYPE: PRT
```

```
<213> ORGANISM: Artificial
<220> FEATURE:
<223> OTHER INFORMATION: peptide

<400> SEQUENCE: 7

Ser Asp Val Val Tyr Thr Asp Trp Lys
1               5

<210> SEQ ID NO 8
<211> LENGTH: 10
<212> TYPE: PRT
<213> ORGANISM: Artificial
<220> FEATURE:
<223> OTHER INFORMATION: peptide

<400> SEQUENCE: 8

Leu Ser Ile Thr Gly Thr Tyr Asp Leu Lys
1               5                   10

<210> SEQ ID NO 9
<211> LENGTH: 10
<212> TYPE: PRT
<213> ORGANISM: Artificial
<220> FEATURE:
<223> OTHER INFORMATION: peptide

<400> SEQUENCE: 9

Ser Val Leu Gly Gln Leu Gly Ile Thr Lys
1               5                   10

<210> SEQ ID NO 10
<211> LENGTH: 10
<212> TYPE: PRT
<213> ORGANISM: Artificial
<220> FEATURE:
<223> OTHER INFORMATION: peptide

<400> SEQUENCE: 10

Thr Ser Ile Val His Leu Phe Glu Trp Arg
1               5                   10

<210> SEQ ID NO 11
<211> LENGTH: 12
<212> TYPE: PRT
<213> ORGANISM: Artificial
<220> FEATURE:
<223> OTHER INFORMATION: peptide

<400> SEQUENCE: 11

Ala Leu Val Phe Val Asp Asn His Asp Asn Gln Arg
1               5                   10

<210> SEQ ID NO 12
<211> LENGTH: 12
<212> TYPE: PRT
<213> ORGANISM: Artificial
<220> FEATURE:
<223> OTHER INFORMATION: peptide

<400> SEQUENCE: 12

Ala Leu Gln Asp Gln Leu Val Leu Val Ala Ala Lys
1               5                   10

<210> SEQ ID NO 13
<211> LENGTH: 24
<212> TYPE: PRT
<213> ORGANISM: Artificial
```

```
<220> FEATURE:
<223> OTHER INFORMATION: peptide

<400> SEQUENCE: 13

Ala Asp Ser Gln Ala Gln Leu Leu Leu Ser Thr Val Val Gly Val Phe
1               5                   10                  15

Thr Ala Pro Gly Leu His Leu Lys
            20

<210> SEQ ID NO 14
<211> LENGTH: 14
<212> TYPE: PRT
<213> ORGANISM: Artificial
<220> FEATURE:
<223> OTHER INFORMATION: peptide

<400> SEQUENCE: 14

Gly Val Asp Glu Val Thr Ile Val Asn Ile Leu Thr Asn Arg
1               5                   10

<210> SEQ ID NO 15
<211> LENGTH: 10
<212> TYPE: PRT
<213> ORGANISM: Artificial
<220> FEATURE:
<223> OTHER INFORMATION: peptide

<400> SEQUENCE: 15

Thr Asn Gln Glu Leu Gln Glu Ile Asn Arg
1               5                   10

<210> SEQ ID NO 16
<211> LENGTH: 14
<212> TYPE: PRT
<213> ORGANISM: Artificial
<220> FEATURE:
<223> OTHER INFORMATION: peptide

<400> SEQUENCE: 16

Leu Leu Asp Asn Trp Asp Ser Val Thr Ser Thr Phe Ser Lys
1               5                   10

<210> SEQ ID NO 17
<211> LENGTH: 11
<212> TYPE: PRT
<213> ORGANISM: Artificial
<220> FEATURE:
<223> OTHER INFORMATION: peptide

<400> SEQUENCE: 17

Ala Thr Glu His Leu Ser Thr Leu Ser Glu Lys
1               5                   10

<210> SEQ ID NO 18
<211> LENGTH: 20
<212> TYPE: PRT
<213> ORGANISM: Artificial
<220> FEATURE:
<223> OTHER INFORMATION: peptide

<400> SEQUENCE: 18

Glu Pro Cys Val Glu Ser Leu Val Ser Gln Tyr Phe Gln Thr Val Thr
1               5                   10                  15

Asp Tyr Gly Lys
            20
```

```
<210> SEQ ID NO 19
<211> LENGTH: 10
<212> TYPE: PRT
<213> ORGANISM: Artificial
<220> FEATURE:
<223> OTHER INFORMATION: peptide

<400> SEQUENCE: 19

Ser Lys Glu Gln Leu Thr Pro Leu Ile Lys
1               5                   10

<210> SEQ ID NO 20
<211> LENGTH: 9
<212> TYPE: PRT
<213> ORGANISM: Artificial
<220> FEATURE:
<223> OTHER INFORMATION: peptide

<400> SEQUENCE: 20

Leu Thr Pro Tyr Ala Asp Glu Phe Lys
1               5

<210> SEQ ID NO 21
<211> LENGTH: 9
<212> TYPE: PRT
<213> ORGANISM: Artificial
<220> FEATURE:
<223> OTHER INFORMATION: peptide

<400> SEQUENCE: 21

Leu Ala Pro Leu Ala Glu Asp Val Arg
1               5

<210> SEQ ID NO 22
<211> LENGTH: 8
<212> TYPE: PRT
<213> ORGANISM: Artificial
<220> FEATURE:
<223> OTHER INFORMATION: peptide

<400> SEQUENCE: 22

Ser Leu Asp Ala Asp Glu Phe Arg
1               5

<210> SEQ ID NO 23
<211> LENGTH: 15
<212> TYPE: PRT
<213> ORGANISM: Artificial
<220> FEATURE:
<223> OTHER INFORMATION: peptide

<400> SEQUENCE: 23

Leu Gly Leu Val Leu Asp Gln Ala Glu Ala Glu Gly Val Cys Arg
1               5                   10                  15

<210> SEQ ID NO 24
<211> LENGTH: 10
<212> TYPE: PRT
<213> ORGANISM: Artificial
<220> FEATURE:
<223> OTHER INFORMATION: peptide

<400> SEQUENCE: 24

Glu Ala Val Ile Ala Ala Ala Phe Ala Lys
1               5                   10
```

```
<210> SEQ ID NO 25
<211> LENGTH: 9
<212> TYPE: PRT
<213> ORGANISM: Artificial
<220> FEATURE:
<223> OTHER INFORMATION: peptide

<400> SEQUENCE: 25

Leu Ala Leu Ile Leu Cys Val Thr Lys
1               5

<210> SEQ ID NO 26
<211> LENGTH: 8
<212> TYPE: PRT
<213> ORGANISM: Artificial
<220> FEATURE:
<223> OTHER INFORMATION: peptide

<400> SEQUENCE: 26

Val Tyr Ile Ile Gln Ala Cys Arg
1               5

<210> SEQ ID NO 27
<211> LENGTH: 11
<212> TYPE: PRT
<213> ORGANISM: Artificial
<220> FEATURE:
<223> OTHER INFORMATION: peptide

<400> SEQUENCE: 27

Tyr Gly Leu Val Thr Tyr Ala Thr Tyr Pro Lys
1               5                   10

<210> SEQ ID NO 28
<211> LENGTH: 16
<212> TYPE: PRT
<213> ORGANISM: Artificial
<220> FEATURE:
<223> OTHER INFORMATION: peptide

<400> SEQUENCE: 28

Glu Ala Gly Ile Pro Glu Phe Tyr Asp Tyr Asp Val Ala Leu Ile Lys
1               5                   10                  15

<210> SEQ ID NO 29
<211> LENGTH: 8
<212> TYPE: PRT
<213> ORGANISM: Artificial
<220> FEATURE:
<223> OTHER INFORMATION: peptide

<400> SEQUENCE: 29

Val Pro Glu Pro Cys Gln Pro Lys
1               5

<210> SEQ ID NO 30
<211> LENGTH: 17
<212> TYPE: PRT
<213> ORGANISM: Artificial
<220> FEATURE:
<223> OTHER INFORMATION: peptide

<400> SEQUENCE: 30

Val Pro Glu Pro Cys Pro Ser Thr Val Thr Pro Ala Pro Ala Gln Gln
1               5                   10                  15

Lys
```

<210> SEQ ID NO 31
<211> LENGTH: 12
<212> TYPE: PRT
<213> ORGANISM: Artificial
<220> FEATURE:
<223> OTHER INFORMATION: peptide

<400> SEQUENCE: 31

Thr Gln Val Val Ala Gly Thr Asn Tyr Tyr Ile Lys
1               5                   10

<210> SEQ ID NO 32
<211> LENGTH: 18
<212> TYPE: PRT
<213> ORGANISM: Artificial
<220> FEATURE:
<223> OTHER INFORMATION: peptide

<400> SEQUENCE: 32

Ser Leu Pro Gly Gln Asn Glu Asp Leu Val Leu Thr Gly Tyr Gln Val
1               5                   10                  15

Asp Lys

<210> SEQ ID NO 33
<211> LENGTH: 11
<212> TYPE: PRT
<213> ORGANISM: Artificial
<220> FEATURE:
<223> OTHER INFORMATION: peptide

<400> SEQUENCE: 33

Glu Asn Ala Gly Glu Asp Pro Gly Leu Ala Arg
1               5                   10

<210> SEQ ID NO 34
<211> LENGTH: 11
<212> TYPE: PRT
<213> ORGANISM: Artificial
<220> FEATURE:
<223> OTHER INFORMATION: peptide

<400> SEQUENCE: 34

Asp Ala Val Glu Asp Leu Glu Ser Val Gly Lys
1               5                   10

<210> SEQ ID NO 35
<211> LENGTH: 14
<212> TYPE: PRT
<213> ORGANISM: Artificial
<220> FEATURE:
<223> OTHER INFORMATION: peptide

<400> SEQUENCE: 35

His Ser Gly Ile Gly His Gly Gln Ala Ser Ser Ala Val Arg
1               5                   10

<210> SEQ ID NO 36
<211> LENGTH: 11
<212> TYPE: PRT
<213> ORGANISM: Artificial
<220> FEATURE:
<223> OTHER INFORMATION: peptide

<400> SEQUENCE: 36

Asn Pro Ser Ala Ala Phe Phe Cys Val Ala Arg
1               5                   10

```
<210> SEQ ID NO 37
<211> LENGTH: 10
<212> TYPE: PRT
<213> ORGANISM: Artificial
<220> FEATURE:
<223> OTHER INFORMATION: peptide

<400> SEQUENCE: 37

Val Ser Glu Glu Ile Glu Asp Ile Ile Lys
1               5                   10

<210> SEQ ID NO 38
<211> LENGTH: 9
<212> TYPE: PRT
<213> ORGANISM: Artificial
<220> FEATURE:
<223> OTHER INFORMATION: peptide

<400> SEQUENCE: 38

Ala Ile Leu Asn Tyr Ile Ala Ser Lys
1               5

<210> SEQ ID NO 39
<211> LENGTH: 8
<212> TYPE: PRT
<213> ORGANISM: Artificial
<220> FEATURE:
<223> OTHER INFORMATION: peptide

<400> SEQUENCE: 39

Ile Ser Asn Leu Pro Thr Val Lys
1               5

<210> SEQ ID NO 40
<211> LENGTH: 10
<212> TYPE: PRT
<213> ORGANISM: Artificial
<220> FEATURE:
<223> OTHER INFORMATION: peptide

<400> SEQUENCE: 40

Val Pro Ala Leu Gly Tyr Leu Asp Val Arg
1               5                   10

<210> SEQ ID NO 41
<211> LENGTH: 10
<212> TYPE: PRT
<213> ORGANISM: Artificial
<220> FEATURE:
<223> OTHER INFORMATION: peptide

<400> SEQUENCE: 41

Thr Gln Asp Val Ser Pro Gln Ala Leu Lys
1               5                   10

<210> SEQ ID NO 42
<211> LENGTH: 10
<212> TYPE: PRT
<213> ORGANISM: Artificial
<220> FEATURE:
<223> OTHER INFORMATION: peptide

<400> SEQUENCE: 42

Asp Phe Thr Cys Val His Gln Ala Leu Lys
1               5                   10
```

```
<210> SEQ ID NO 43
<211> LENGTH: 10
<212> TYPE: PRT
<213> ORGANISM: Artificial
<220> FEATURE:
<223> OTHER INFORMATION: peptide

<400> SEQUENCE: 43

Leu Leu Asp Ser Leu Pro Ser Asp Thr Arg
1               5                   10

<210> SEQ ID NO 44
<211> LENGTH: 14
<212> TYPE: PRT
<213> ORGANISM: Artificial
<220> FEATURE:
<223> OTHER INFORMATION: peptide

<400> SEQUENCE: 44

Phe Pro Ser Val Ser Leu Gln Glu Ala Ser Ser Phe Phe Arg
1               5                   10

<210> SEQ ID NO 45
<211> LENGTH: 8
<212> TYPE: PRT
<213> ORGANISM: Artificial
<220> FEATURE:
<223> OTHER INFORMATION: peptide

<400> SEQUENCE: 45

His Pro Gln Glu Gln Pro Leu Trp
1               5

<210> SEQ ID NO 46
<211> LENGTH: 9
<212> TYPE: PRT
<213> ORGANISM: Artificial
<220> FEATURE:
<223> OTHER INFORMATION: peptide

<400> SEQUENCE: 46

Val Leu Ala Glu Val Gln Glu Gly Arg
1               5

<210> SEQ ID NO 47
<211> LENGTH: 9
<212> TYPE: PRT
<213> ORGANISM: Artificial
<220> FEATURE:
<223> OTHER INFORMATION: peptide

<400> SEQUENCE: 47

Val His Val Val Phe Ser Thr Glu Arg
1               5

<210> SEQ ID NO 48
<211> LENGTH: 8
<212> TYPE: PRT
<213> ORGANISM: Artificial
<220> FEATURE:
<223> OTHER INFORMATION: peptide

<400> SEQUENCE: 48

Val Pro Glu Pro Gly Tyr Thr Lys
1               5
```

```
<210> SEQ ID NO 49
<211> LENGTH: 8
<212> TYPE: PRT
<213> ORGANISM: Artificial
<220> FEATURE:
<223> OTHER INFORMATION: peptide

<400> SEQUENCE: 49

Val Pro Glu Pro Gly Ser Ile Lys
1               5

<210> SEQ ID NO 50
<211> LENGTH: 30
<212> TYPE: PRT
<213> ORGANISM: Artificial
<220> FEATURE:
<223> OTHER INFORMATION: peptide

<400> SEQUENCE: 50

Phe Gly Tyr Gly Tyr Gly Pro Tyr Gln Pro Val Pro Glu Gln Pro Leu
1               5                   10                  15

Tyr Pro Gln Pro Tyr Gln Pro Gln Tyr Gln Gln Tyr Thr Phe
            20                  25                  30

<210> SEQ ID NO 51
<211> LENGTH: 15
<212> TYPE: PRT
<213> ORGANISM: Artificial
<220> FEATURE:
<223> OTHER INFORMATION: peptide

<400> SEQUENCE: 51

Ala Val Phe Val Asp Leu Glu Pro Thr Val Ile Asp Glu Val Arg
1               5                   10                  15

<210> SEQ ID NO 52
<211> LENGTH: 16
<212> TYPE: PRT
<213> ORGANISM: Artificial
<220> FEATURE:
<223> OTHER INFORMATION: peptide

<400> SEQUENCE: 52

Ile His Phe Pro Leu Ala Thr Tyr Ala Pro Val Ile Ser Ala Glu Lys
1               5                   10                  15

<210> SEQ ID NO 53
<211> LENGTH: 17
<212> TYPE: PRT
<213> ORGANISM: Artificial
<220> FEATURE:
<223> OTHER INFORMATION: peptide

<400> SEQUENCE: 53

Val Glu Ala Pro Thr Thr Leu Gly Asp Asn Thr Ala Ala Asn Asn Val
1               5                   10                  15

Arg

<210> SEQ ID NO 54
<211> LENGTH: 12
<212> TYPE: PRT
<213> ORGANISM: Artificial
<220> FEATURE:
<223> OTHER INFORMATION: peptide

<400> SEQUENCE: 54
```

```
Gly Leu Gly Asp Asp Thr Ala Leu Asn Asp Ala Arg
1               5                   10

<210> SEQ ID NO 55
<211> LENGTH: 10
<212> TYPE: PRT
<213> ORGANISM: Artificial
<220> FEATURE:
<223> OTHER INFORMATION: peptide

<400> SEQUENCE: 55

Leu Val Asn Glu Val Thr Glu Phe Ala Lys
1               5                   10

<210> SEQ ID NO 56
<211> LENGTH: 16
<212> TYPE: PRT
<213> ORGANISM: Artificial
<220> FEATURE:
<223> OTHER INFORMATION: peptide

<400> SEQUENCE: 56

Arg Pro Cys Phe Ser Ala Leu Glu Val Asp Glu Thr Tyr Val Pro Lys
1               5                   10                  15
```

NASOPHARYNGEAL PROTEIN BIOMARKERS OF ACUTE RESPIRATORY VIRUS INFECTION AND METHODS OF USING SAME

RELATED APPLICATIONS

This application is a 35 U.S.C. § 371 national phase application of International Application Serial No. PCT/US2018/016611, filed Feb. 2, 2018, which claims the benefit of U.S. Provisional Patent Application Ser. No. 62/454,260, filed Feb. 3, 2017, the disclosure of which is incorporated by reference herein in its entirety.

FEDERAL FUNDING LEGEND

This invention was made with Government Support under Federal Grant Nos. N6601-09-C-2082 and N6601-07-C-2024 awarded by the DOD/DARPA. The Government has certain rights to this invention.

STATEMENT REGARDING ELECTRONIC FILING OF A SEQUENCE LISTING

A Sequence Listing in ASCII text format, submitted under 37 C.F.R. § 1.821, entitled 5470-505_ST25.txt, 11,488 bytes in size, generated on Jul. 30, 2019 and filed via EFS-Web, is provided in lieu of a paper copy. This Sequence Listing is incorporated by reference into the specification for its disclosures.

BACKGROUND

Acute respiratory infections are common causes of presentation in outpatient and emergent care settings, and represent a significant cause of morbidity and mortality. Currently available diagnostics are limited, creating uncertainty in decisions to use antimicrobials or supportive care. As a result, a large fraction of patients receive "unnecessary" antimicrobial prescriptions, contributing to the emergence and spread of antimicrobial resistant pathogens. Measurement of the host response to infection is an alternative to pathogen-based diagnostic testing and may complement and improve diagnostic accuracy. We identified host proteins in the nasopharyngeal space associated with acute respiratory viral infection, and developed analyte specific assays and a multianalyte classifier capable of detecting a respiratory virus (e.g., influenza, rhinovirus, etc.) infection with high accuracy.

SUMMARY

The present disclosure provides, in part, a molecular diagnostic test that overcomes many of the limitations of current methods for the determination of the etiology of respiratory infection. The test detects the host's response to an acute respiratory virus (ARV) infection by measuring and analyzing the expression of a discrete set of proteins or component peptides in nasal samples. The proteins or peptides in this "signature", revealed by statistical analysis, are differentially expressed in individuals presenting with an ARV infection. Monitoring the host response to ARV infection using this multianalyte test in conjunction with analytic methods provides a classifier of high diagnostic accuracy and clinical utility, allowing health care providers to use the response of the host (the subject or patient) to reliably determine the presence or absence of a respiratory viral infection.

One aspect of the present disclosure provides a method for making an acute respiratory viral illness classifier for a platform, wherein the classifier comprises a plurality of viral ARV subsets, said method comprising, consisting of, or consisting essentially of: (a) obtaining biological samples from a plurality of subjects known to be suffering from a viral acute respiratory infection; (b) measuring on said platform the expression levels of a plurality of gene products in each of said biological samples from step (a); (c) normalizing the gene product expression levels obtained in step (b) to generate normalized expression values; and (c) generating a viral ARI classifier for the platform based upon said normalized gene product expression values to thereby make the acute respiratory viral illness classifiers for said platform.

In some embodiments, the measuring comprises, or is preceded by, one or more steps of: purifying cells, cellular materials, or secreted materials from said sample, preserving or disrupting the cells or cellular materials of said sample, and reducing complexity of sample through isolating or fractionating gene products from the sample.

In other embodiments, the measuring comprises quantitative or semi-quantitative direct detection or indirect detection using analyte specific reagents such as antibodies, antibody fragments, or aptamers.

In another embodiment, the platform comprises an array platform, a gene product analyte hybridization or capture platform, multi-signal coded (e.g., fluorescence) detector platform, a mass spectrometry platform, an amino acid sequencing platform, or a combination thereof.

In some embodiments, the generating comprises iteratively: (i) assigning a weight for each normalized gene product expression value, entering the weight and expression value for each gene product into a classifier (e.g., a linear regression classifier) equation and determining a score for outcome for each of the plurality of subjects, then (ii) determining the accuracy of classification for each outcome across the plurality of subjects, and then (iii) adjusting the weight until accuracy of classification is optimized to provide said viral ARI for the platform, wherein analytes having a non-zero weight are included in the respective classifier, and optionally uploading components of each classifier (gene product analytes, weights and/or etiology threshold value) onto one or more databases.

In some embodiments, the classifier is a linear regression classifier and said generating comprises converting a score of said classifier to a probability.

In other embodiments, the method further comprises validating said ARI classifier against a known dataset comprising at least two relevant clinical attributes.

In other embodiments, the viral classifier comprises expression levels of 1, 5, 10, 15, 20, 25 or 26 of the gene products listed as part of a viral ARI classifier in Table 2. In certain embodiments, the pre-defined set of gene products comprises from 1-26 proteins and/or component peptides/epitopes of gene products listed in Table 2/2A or Table S4.

In another embodiment, the biological sample is selected from the group consisting of peripheral blood, sputum, nasal or nasopharyngeal swab, nasopharyngeal lavage, bronchoalveolar lavage, endotracheal aspirate, respiratory expectorate, respiratory epithelial cells or tissue, or other respiratory cell, tissue, or secretion samples and combinations thereof In another embodiment, the biologic sample is obtained as a nasal or respiratory spray captured onto paper-based matrix for extraction or direct assay (e.g., colorimetric test):

In some embodiments, the biologic sampling site is the nasopharyngeal space, endotracheal, etc. In some embodiments, the sampling method is lavage, swab, curettage, expectorate, etc.

Another aspect of the present disclosure provides a method for determining the presence of a respiratory virus in a subject comprising, consisting of, or consisting essentially of: (a) obtaining a biological sample from the subject; (b) measuring on a platform expression levels of a pre-defined set of gene products (i.e., signature) in said biological sample; (c) normalizing the gene product expression levels to generate normalized expression values; (d) entering the normalized gene product expression values into one or more acute respiratory virus illness classifiers, said classifier(s) comprising pre-defined weighting values (i.e., coefficients) for each of the gene products of the pre-determined set of proteins and/or peptides for the platform, optionally wherein said classifier(s) are retrieved from one or more databases; and (e) calculating presence probability for one or more of a viral ARI illness based upon said normalized expression values and said classifier(s), to thereby determine the presence of a respiratory virus infection in the subject.

Another aspect of the present disclosure provides a method for determining the etiology of an acute respiratory viral (ARV) illness in a subject suffering therefrom, comprising, consisting of, or consisting essentially of: (a) obtaining a biological sample from the subject; (b) measuring on a platform expression levels of a pre-defined set of gene products (i.e., signature) in said biological sample; (c) normalizing the gene product expression levels to generate normalized expression values; (d) entering the normalized gene product expression values into one or more acute respiratory virus illness classifiers, said classifier(s) comprising pre-defined weighting values (i.e., coefficients) for each of the gene products of the pre-determined set of gene products for the platform, optionally wherein said classifier(s) are retrieved from one or more databases; and (e) calculating an etiology probability for one or more of a viral ARI illness based upon said normalized expression values and said classifier(s), to thereby determine the etiology of the acute respiratory virus illness in the subject. In some embodiments, the determination is to identify influenza virus.

Another aspect of the present disclosure provides a method for determining whether a subject is at risk of developing an ARV illness, comprising, consisting of, or consisting essentially of: (a) obtaining a biological sample from the subject; (b) measuring on a platform expression levels of a pre-defined set of gene products (i.e., signature) in said biological sample; (c) normalizing the gene product expression levels to generate normalized expression values; (d) entering the normalized gene product expression values into one or more acute respiratory virus illness classifiers, said classifier(s) comprising pre-defined weighting values (i.e., coefficients) for each of the gene products of the pre-determined set of proteins and/or peptides for the platform, optionally wherein said classifier(s) are retrieved from one or more databases; and (e) calculating a risk probability for one or more of a viral ARI illness based upon said normalized expression values and said classifier(s), to thereby determine whether the subject is a risk of developing an ARV illness.

Another aspect of the present disclosure provides a method for determining the presence of a latent or subclinical respiratory viral infection in a subject exhibiting no symptoms comprising, consisting of, or consisting essentially of: (a) obtaining a biological sample from the subject; (b) measuring on a platform expression levels of a pre-defined set of gene products (i.e., signature) in said biological sample; (c) normalizing the gene product expression levels to generate normalized expression values; (d) entering the normalized gene product expression values into one or more acute respiratory virus illness classifiers, said classifier(s) comprising pre-defined weighting values (i.e., coefficients) for each of the gene products of the pre-determined set of gene products for the platform, optionally wherein said classifier(s) are retrieved from one or more databases; and (e) calculating a probability for one or more of a viral ARI illness based upon said normalized expression values and said classifier(s), to thereby determine the presence of a latent or subclinical respiratory viral infection in the subject.

In some embodiments, the methods further comprise (f) comparing the probability to pre-defined thresholds, cut-off values, or ranges of values (e.g., a confidence interval) that indicate an infection or a likelihood of infection.

In some embodiments, the gene product comprises proteins and/or component peptides (e.g., all expressed proteins and/or peptides, or expressed proteome, epitopes or a subset thereof).

In some embodiments, the subject is suffering from acute respiratory virus illness symptoms. In other embodiments, the subject is suspected of having a viral infection.

In some embodiments, a combined host protein or peptide viral ARI classifier is combined or measured in parallel with pathogen detection from said samples.

In yet another embodiment, the method further comprises generating a report assigning the subject a score indicating the probability of the presence and/or etiology of the acute respiratory illness.

In yet another embodiment, the etiology of the AVR illness comprises a respiratory virus. In some embodiments, the AVR illness is selected from the group consisting of, but not limited to, human rhinovirus (HRV), respiratory syncytial virus (RSV), influenza, and combinations thereof.

In some embodiments, the pre-defined set of analytes comprises from 1-26 gene products. In certain embodiments, the pre-defined set of gene products comprises from 1-26 proteins and/or component peptides of gene products listed in Table 2/2A or Table S4.

In another embodiment, the viral ARI classifier is obtained by any method described herein.

In some embodiments, the method of treating comprises administering to the subject an appropriate treatment regimen based on an etiology determined by a method as described herein. In certain embodiments, the appropriate treatment regimen comprises an antiviral therapy.

Another aspect of the present disclosure provides a method of monitoring response to a vaccine, drug or other antiviral therapy in a subject suffering from, or at risk of developing, an acute respiratory viral illness comprising determining a host response of said subject using any of the methods described herein. In some embodiments, the drug is an antiviral drug.

Yet another aspect of the present disclosure provides a system for determining the presence of and/or determining an etiology of an acute respiratory viral illness in a subject comprising, consisting of, or consisting essentially of: (i) at least one processor; (ii) a sample input circuit configured to receive a biological sample from the subject; (iii) a sample analysis circuit coupled to the at least one processor and configured to determine gene product expression levels of the biological sample; (iv) an input/output circuit coupled to the at least one processor; (v) a storage circuit coupled to the at least one processor and configured to store data, parameters, and/or classifiers; and (iv) a memory coupled to the processor and comprising computer readable program code embodied in the memory that when executed by the at least one processor causes the at least one processor to perform operations comprising: (a) controlling/performing measurement via the sample analysis circuit of protein and/or peptide expression levels of a pre-defined set of gene products (i.e., signature) in said biological sample; (b) normalizing the gene product expression levels to generate normalized gene product expression values; retrieving from the storage circuit a viral ARI classifier, said classifier(s) comprising predefined weighting values (i.e., coefficients) for each of the analytes of the pre-defined set of gene products; (c) entering the normalized gene product expression values into one or more acute respiratory viral illness classifiers selected from the viral ARI classifier; (d) calculating a presence and/or etiology probability for one or more of a viral ARI based upon said classifier(s); and (e) controlling output via the input/output circuit of a determination of the presence of, or the etiology of, the acute respiratory viral illness in the subject.

In some embodiments, the system comprises computer readable code to transform quantitative, or semi-quantitative, detection of gene product expression to a cumulative score or probability of the etiology of the ARI.

In another embodiment, the system comprises an array platform, a gene product (e.g., protein and/or peptide) analyte hybridization or capture platform, multi-signal coded (e.g., fluorescence) detector platform, a mass spectrometry platform, an amino acid sequencing platform, or a combination thereof.

In some embodiments, the pre-defined set of analytes comprises from 1-26 gene products. In certain embodiments, the pre-defined set of analytes comprises from 1-26 proteins and/or component peptides/epitopes of gene products listed in Table 2/2A or Table S4.

The methods described herein are also useful in screening a population of subjects for the presence or absence of viral infections in, for example, a pandemic outbreak. Hence, another aspect of the present disclosure provides a method for determining the presence or absence of a respiratory virus in a population of subjects comprising, consisting of, or consisting essentially of: (a) obtaining a biological sample from the subjects; (b) measuring on a platform expression levels of a pre-defined set of gene products (i.e., signature) in said biological samples; (c) normalizing the gene product expression levels to generate normalized expression values; (d) entering the normalized gene product expression values into one or more acute respiratory virus illness classifiers, said classifier(s) comprising pre-defined weighting values (i.e., coefficients) for each of the gene products of the pre-determined set of proteins and/or peptides for the platform, optionally wherein said classifier(s) are retrieved from one or more databases; and (e) calculating presence probability for one or more of a viral ARI illness based upon said normalized expression values and said classifier(s), to thereby determine the presence or absence of a respiratory virus in the population of subjects. In some embodiments, the methods further comprise administering an antiviral treatment to the subject(s) that have been determined to have an acute viral infection. In other embodiments, the method may further comprise quarantining those subjects determined to have an acute respiratory infection.

The methods described herein are also useful for practitioners to help determine when an antibiotic should or should not be prescribed to a subject suffering from an acute respiratory infection. Yet another aspect of the present disclosure provides a method for determining whether an antibiotic should be administered to a subject suffering from a respiratory virus infection comprising, consisting of, or consisting essentially of: (a) obtaining a biological sample from the subject; (b) measuring on a platform expression levels of a pre-defined set of gene products (i.e., signature) in said biological sample; (c) normalizing the gene product expression levels to generate normalized expression values; (d) entering the normalized gene product expression values into one or more acute respiratory virus illness classifiers, said classifier(s) comprising pre-defined weighting values (i.e., coefficients) for each of the gene products of the pre-determined set of proteins and/or peptides for the platform, optionally wherein said classifier(s) are retrieved from one or more databases; and (e) calculating presence probability for one or more of a viral ARI illness based upon said normalized expression values and said classifier(s), to thereby determine the presence of a respiratory virus in the subject; and (f) not administering to the subject an antibacterial therapy if the presence of a respiratory virus is determined.

Another aspect of the present disclosure provides a kit for determining the presence or absence of viral etiology of an ARI/illness in a subject comprising, consisting of, or consisting essentially of (a) a means for extracting a biological sample; (b) a means for generating one or more arrays or assay panels consisting of a plurality of antibodies, antibody fragments, aptamers, or other analyte specific or signal-generating (e.g. labeled secondary antibody) reagents for use in measuring gene product expression levels as taught herein; and (c) instructions for use.

Another aspect of the present disclosure provides a kit for determining the presence or absence of viral etiology of an ARI illness in a subject comprising, consisting of, or consisting essentially of (a) a means for extracting a biological sample; (b) a means for measuring expression levels of one or more gene products consisting of "spike-in" labeled peptides or protein fragments (e.g. stable isotope labeled peptides) for use in relative quantitation of endogenous gene product expression levels (e.g. mass spectrometry) as taught herein; and (c) instructions for use.

Yet another aspect of the present disclosure provides a kit for detecting the presence of a respiratory virus in a subject comprising, consisting of, or consisting essentially of (a) a means for extracting a biological sample; (b) a means for generating one or more arrays consisting of a plurality of antibodies or other analyte specific reagents for use in measuring gene product expression levels as taught herein; and (c) instructions for use.

Yet another aspect of the present disclosure provides all that is disclosed and illustrated herein.

BRIEF DESCRIPTION OF THE DRAWINGS

The foregoing aspects and other features of the disclosure are explained in the following description, taken in connection with the accompanying drawings, herein:

(FIG. 4A) Probability of positive is plotted (x-axis) for individual participant samples from 4 cohorts, with threshold for positive classification set at >0.5. Lines connect paired samples from individuals at baseline (left) and time T (right). Inf=infected; Uninf=uninfected; Sham=uninfected sham inoculation; open circles=classifier agrees with phenotype label; X=classifier disagrees with phenotype label. (FIG. 4B) Receiver operating curve for LOOCV with the 10 peptide (9 unique proteins) classifier. The optimal threshold on the curve (open circle) produces 0.8623 AUROC, 75% TPR, 97.46% TNR, with the confusion matrix and peptide weights shown in Tables 3A and 3B, respectively.

(FIG. 7B) Yeast ADH spiked control reproducibility is plotted as average coefficient of variation (%) of 5 measured heavy/light SIL pairs across individual sample data acquisitions for each experimental challenge cohort. (FIG. 7C) QC pool reproducibility as average coefficient of variation (%) of 56 measured heavy/light SIL pairs across QC pool data acquisitions (every ~12 hrs) for each experimental challenge cohort.

DETAILED DESCRIPTION

Figure 1:
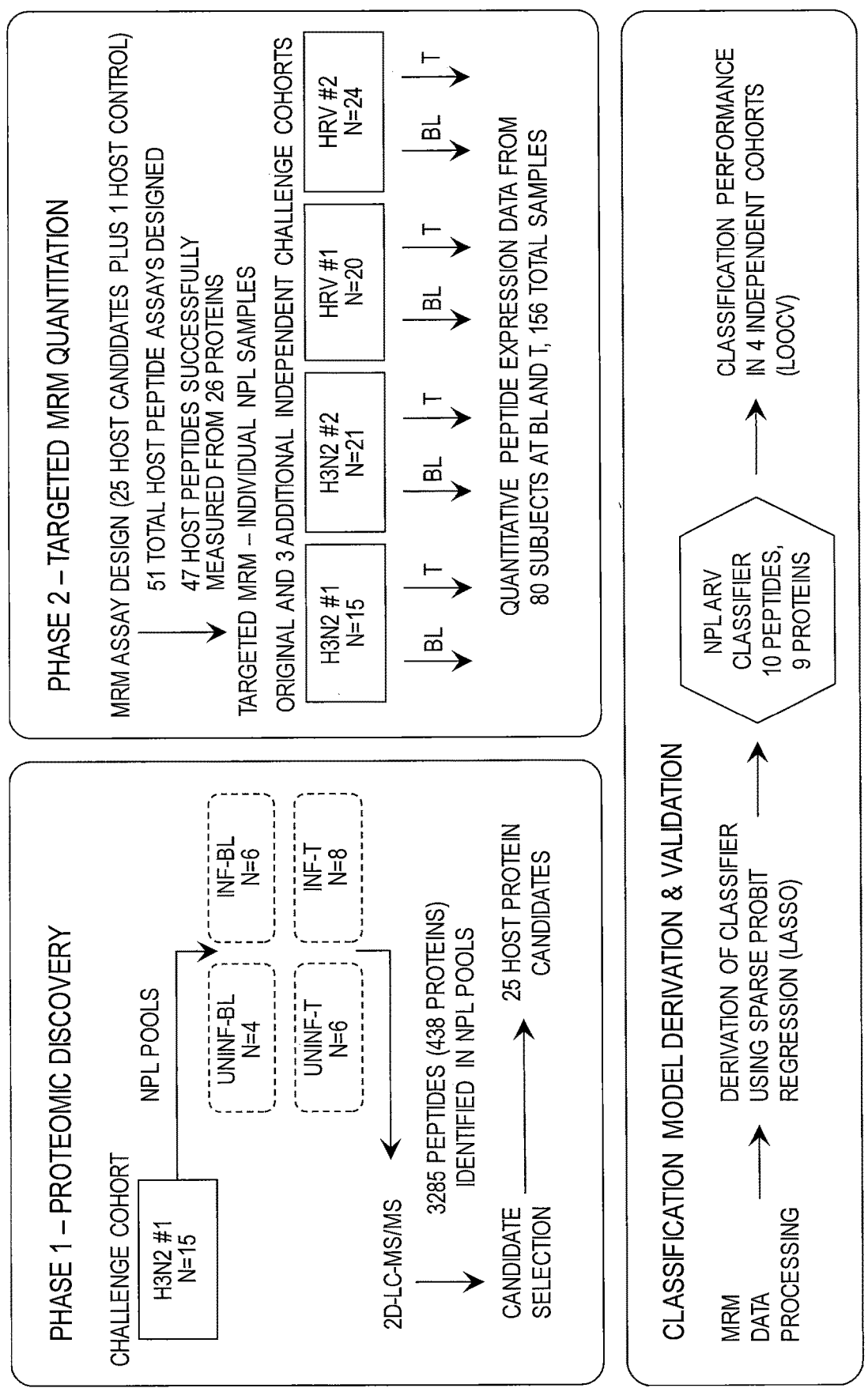
FIG. 1 is a flow chart showing the study design and workflow for development and verification of protein and/or peptide biomarkers in a human challenge model of ARV infection in accordance with one embodiment of the present disclosure. A two-phased strategy was employed to identify and characterize candidate protein biomarkers of ARV infection from NPL samples collected from participants in four experimental ARV challenge cohorts. For phase 1 discovery analysis, four NPL pools were prepared from H3N2 #1 cohort and analyzed using unbiased 2D-LC-MS/MS. The numbers of subject (N) with samples included in each pool are shown (Uninf =uninfected individuals; Inf=infected individuals; BL=baseline; T=time of maximal symptoms). For phase 2, the original and three additional independent challenge cohorts were assayed by targeted MRM. Quantitative peptide expression data from 80 individuals and 156 total samples were used in the derivation of an NPL ARV classifier, and classification performance was assessed in independent challenge cohorts using LOOCV.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs. One basis of the present disclosure provides that alterations in gene products, including protein, peptides, and metabolite expression in biological samples in response to pathogen exposure that causes acute respiratory infections can be used to classify the presence or absence of viral etiology of the ARI in a subject with a high degree of accuracy.

Definitions

As used herein, the term "Acute Respiratory infection" or "ARI" refers to those infections of the upper or lower respiratory tract, usually due to a bacterial or viral pathogen, and characterized by rapid progression of symptoms over hours to days. ARIs may primarily be of the upper respiratory tract (URIs), the lower respiratory tract infections (LRIs), or a combination of the two. ARIs may have systemic effects due to spread of the infection beyond the respiratory tract or due to collateral damage induced by the immune response. The term "Acute Respiratory Viral" or "ARV" refers to those ARIs caused by a viral pathogen. Many viruses cause such acute respiratory illnesses, including but not limited to, human rhinovirus (HRV), respiratory syncytial virus (RSV), and influenza.

As used herein, the term "signature" as used herein and refer to a set of biological analytes and the measurable quantities of said analytes whose expression level signifies the presence or absence of the specified biological state.

These signatures are discovered in a plurality of subjects with known infection status (e.g. a confirmed respiratory viral infection, or lacking respiratory virus infection), and are discriminative (individually or jointly) of one or more categories or outcomes of interest. These measurable quantities, also known as biological markers can be (but not limited to) gene expression levels, protein or peptide levels, or metabolite levels.

In some embodiments, a "signature" may comprise a particular combination of gene products whose expression levels, when incorporated into a classifier as taught herein, discriminate a condition such as a viral ARI. The term "viral ARI gene product expression levels," "viral ARI signature", and "ARV signature" are used interchangeably and refer to the level of gene products, for example, such as those proteins and/or peptides found in Table 2/2A or Table S4. The altered expression of one or more of these gene products is indicative of the subject having a viral ARI. In some embodiments, the signature is able to distinguish individuals with infection due to viral pathogen from individuals lacking infection or infected with non-viral pathogen.

As used herein, the term "gene product" refers to any biochemical material resulting from the expression of a gene. Examples include, but are not limited to, nucleic acids such as RNA and mRNA, proteins, component peptides, expressed proteomes, epitopes, and any subsets thereof, and combinations thereof. In certain embodiments, the gene product comprises proteins and/or component peptides (e.g., all expressed proteins and/or peptides, or expressed proteome, epitopes or a subset thereof).

The term "genetic material" refers to a material used to store genetic information in the nuclei or mitochondria of an organism's cells. Examples of genetic material include, but are not limited to double-stranded and single-stranded DNA, cDNA, RNA, mRNA, or their encoded products.

As used herein, the terms "classifier" and "predictor" are used interchangeably and refer to a mathematical function that uses the values of the signature (e.g. gene expression levels or protein and/or peptide levels from a defined set of gene products) and a pre-determined coefficient for each signature component to generate scores for a given observation or individual patient for the purpose of assignment to a category. A classifier is linear if scores are a function of summed signature values weighted by a set of coefficients. Furthermore, a classifier is probabilistic if the function of signature values generates a probability, a value between 0 and 1.0 (or 0 and 100%) quantifying the likelihood that a subject or observation belongs to a particular category or will have a particular outcome, respectively. Probit regression and logistic regression are examples of probabilistic linear classifiers.

Figure 5:
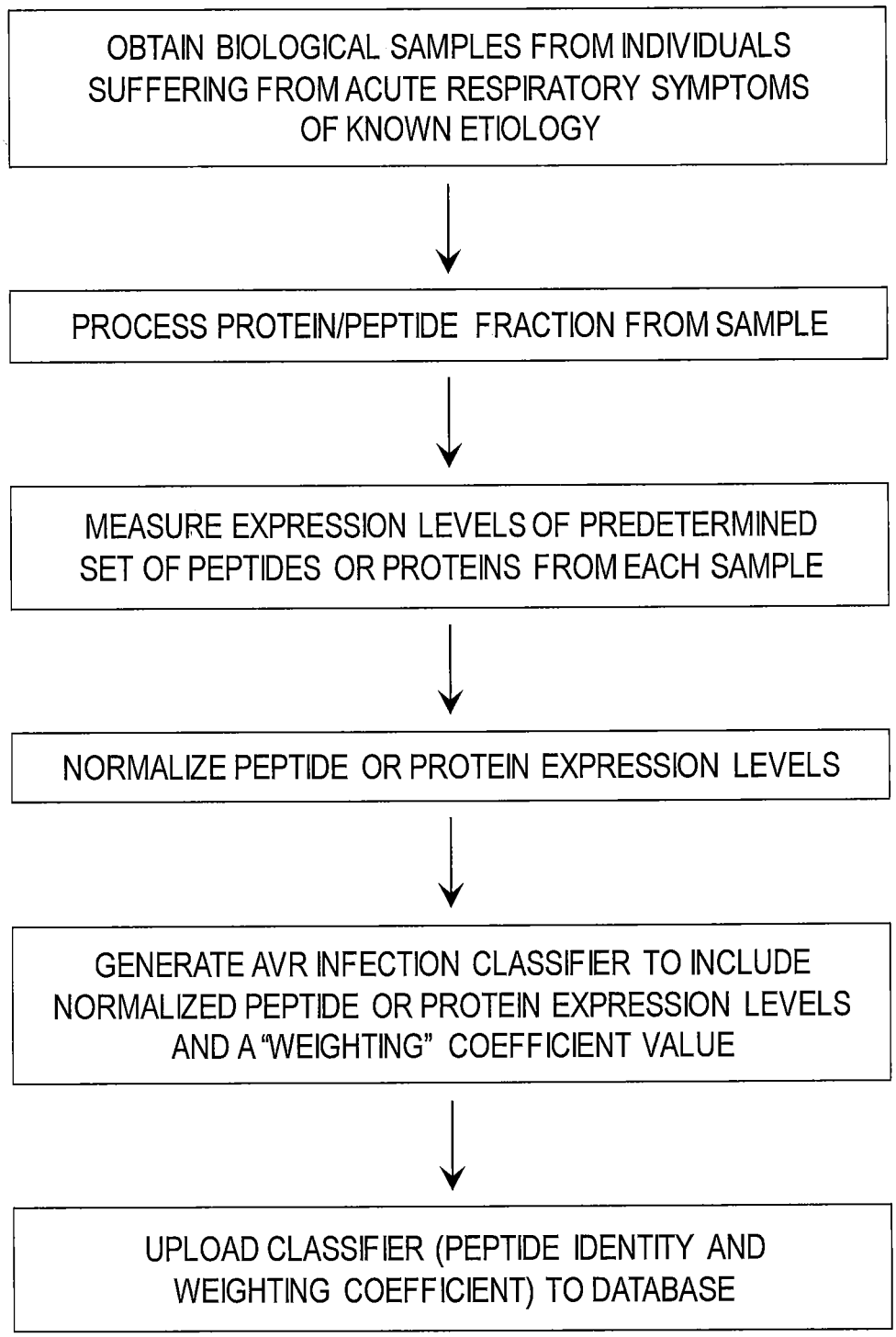
FIG. 5 is a flow chart outlining the training steps in accordance with one embodiment of the present disclosure.

A classifier, including a linear classifier, may be obtained by a procedure known as training, which consists of using a set of data containing observations with known category membership (see, e.g., FIG. 5). Specifically, training seeks to find the optimal coefficient for each component of a given signature, where the optimal result is determined by the highest classification accuracy. In some embodiments, a unique classifier may be developed and trained with respect to a particular platform upon which the signature is measured.

Classification is the activity of assigning an observation or a patient to one or more categories or outcomes (e.g. a patient is infected with a pathogen or is not infected, another categorization may be that a patient is infected with a virus or infected with a bacterium). In some cases, an observation or a patient may be classified to more than one category, e.g. in case of co-infection. The outcome, or category, is determined by the value of the scores provided by the classifier, when such predicted values are compared to a cut-off or threshold value or limit. In other scenarios, the probability of belonging to a particular category may be given if the classifier reports probabilities.

As used herein, the term "indicative" when used with a gene product (e.g., protein and/or peptide) expression levels, means that the expression levels are up-regulated or down-regulated, altered, or changed compared to the expression levels in alternative biological states or control (e.g., uninfected). The term "indicative" when used with protein and/or peptide levels means that the expression levels are higher or lower, increased or decreased, altered, or changed compared to the standard protein levels.

The term "subject" and "patient" are used interchangeably and refer to any organism being examined, studied or treated. It is not intended that the present disclosure be limited to any particular type of subject. In some embodiments of the present invention, humans are the preferred subject, while in other embodiments nonhuman animals are the preferred subject, including but not limited to mice, monkeys, ferrets, cattle, sheep, goats, pigs, chicken, turkeys, dogs, cats, horses and reptiles. In some embodiments, the subject is suffering from an ARI or is displaying ART-like symptoms. In certain embodiments, the subject is suffering from an ARV or is displaying ARV-like symptoms. In certain embodiments, the subject is suspected of having been exposed to an ARV but is not suffering apparent ARI symptoms.

"Platform" or "technology" as used herein refers to an apparatus (e.g., instrument and associated parts, computer, computer-readable media comprising one or more databases as taught herein, reagents, etc.) that may be used to measure a signature, e.g., gene expression levels, in accordance with the present disclosure. Examples of platforms include, but are not limited to, an array platform, a nucleic acid sequencing platform, a thermocycler platform (e.g., multiplexed and/or real-time PCR platform [e.g., a TaqMan® Low Density Array (TLDA), a Biocartis Idylla™ sample-to-result technology, etc.]), a gene product hybridization or capture platform (e.g., a protein and/or peptide hybridization or capture platform), a multi-signal coded (e.g., fluorescence) detector platform, etc., a mass spectrometry platform, an amino acid sequencing platform, a magnetic resonance platform (e.g., the T2 Biosystem® T2 Magnetic Resonance (T2MR®) technology; electrospray ionization (ESI), matrix-assisted laser desorbtion/ionization (MALDI), etc.), and combinations thereof In some embodiments, the platforms may comprise a protein and/or peptide hybridization or capture platform, a multi-signal coded (e.g., fluorescence) detector platform, etc., an amino acid sequencing platform and combinations thereof.

In some embodiments, the platform is configured to measure gene product (e.g., protein and/or peptide) expression levels semi-quantitatively, that is, rather than measuring in discrete or absolute expression, the expression levels are measured as an estimate and/or relative to each other or a specified marker or markers (e.g., expression of another, "standard" or "reference," gene or gene product [e.g., protein or peptide]).

In some embodiments, semi-quantitative measuring includes immunodetection methods including ELISA or protein arrays, which utilize analyte specific immuno-reagents to provide specificity for particular protein or peptide sequence and/or structure, coupled with signal detection modalities such as fluorescence or luminescence to provide the estimated or relative expression levels of the genes within the signature.

The terms "array," "microarray" and "micro array" are interchangeable and refer to an arrangement of a collection of reagents presented on a substrate. Any type of array can be utilized in the methods provided herein. For example, arrays can be on a solid "planar" substrate (a solid phase array), such as a glass slide, or on a semi-solid substrate, such as nitrocellulose membrane. Arrays can also be presented on beads, i.e., a bead array. These beads are typically microscopic and may be made of, e.g., polystyrene. The array can also be presented on nanoparticles, which may be made of, e.g., particularly gold, but also silver, palladium, or platinum. Magnetic nanoparticles may also be used. Other examples include nuclear magnetic resonance microcoils. The analyte specific reagents can be antibody or antibody fragments or nucleic acid aptamers, for example. The arrays may additionally comprise other compounds, such as nucleic acids, peptides, proteins, cells, chemicals, carbohydrates, and the like that specifically bind proteins, peptides, or metabolites.

An array platform may include, for example, the MesoScaleDiscovery (MSD) platform for measurement of multiple analytes per well, configured as antibody "spots" in each assay well. The MSD platform utilizes chemiluminescent reagents activated upon electrical stimulation, or "electrochemiluminescence" detection.

A hybridization and multi-signal coded detector platform includes, for example, NanoString nCounter® technology, in which hybridization of a color-coded barcode attached to a target-specific probe (e.g., barcoded antibody probe) is detected; and Luminex® technology, in which microsphere beads are color coded and coated with a target-specific reagents (e.g., color-coded beads coated with analyte-specific antibody) probe for detection.

Gene products may also be measured using mass spectrometry. For example, protein and/or peptide mass spectrometry (MS) utilizes instruments capable of accurate mass determination and includes a variety of instruments and methods. In some embodiments, the measurement by MS is performed using two primary methods: electrospray ionization (ESI) and matrix-assisted laser desorbtion/ionization (MALDI). Proteins may be analyzed either as "top-down" approach characterizing intact proteins, or a "bottom up" approach characterizing digested protein fragments or peptides. Protein or peptide MS may be performed in conjunction with up-front methods to reduce complexity of biological samples, such as gel electrophoresis or liquid chromatography. Resulting MS data can be used to identify and quantify specific proteins and/or peptides.

The term "computer readable medium" refers to any device or system for storing and providing information (e.g., data and instructions) to a computer processor. Examples of computer readable media include, but are not limited to, DVDs, CDs hard disk drives, magnetic tape and servers for streaming media over networks, and applications, such as those found on smart phones and tablets. In various embodiments, aspects of the present invention including data structures and methods may be stored on a computer readable medium. Processing and data may also be performed on numerous device types, including but not limited to, desk top and lap top computers, tablets, smart phones, and the like.

Any combination of one or more computer readable media may be utilized. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

As used herein, the term biological sample comprises any sample that may be taken from a subject that contains gene product material (e.g. proteins or peptides) that can be used in the methods provided herein. For example, a biological sample may comprise a nasopharyngeal lavage or wash sample or a nasal swab. Other samples may comprise those taken from the upper respiratory tract, including but not limited to, sputum, nasopharyngeal swab, respiratory expectorate, epithelial cells or tissue from upper respiratory tract. A biological sample may also comprise those samples taken from the lower respiratory tract, including but not limited to, bronchoalveolar lavage and endotracheal aspirate. A biological sample may also comprise peripheral blood. A biological sample may also comprise any combinations thereof.

As used herein, the terms "treat", "treatment" and "treating" refer to the reduction or amelioration of the severity, duration and/or progression of a disease or disorder or one or more symptoms thereof resulting from the administration of one or more therapies. Such terms refer to a reduction in the replication of a virus, or a reduction in the spread of a virus to other organs or tissues in a subject or to other subjects. Such terms also refer to the reduction of symptoms by suppression of host response to the infecting organism. Treatment may also include therapies for ARIs resulting from non-infectious illness, such as allergy treatment, asthma treatments, and the like. In some embodiments, the treatment comprises an antiviral treatment.

The term "effective amount" refers to an amount of a therapeutic agent that is sufficient to exert a physiological effect in the subject. The term "responsivity" refers to a change in gene product levels of genes in a subject in response to the subject being infected with a virus compared to the gene expression levels of the genes in a subject that is not infected with a virus, or a control subject. In some embodiments, "responsivity" refers to a change in gene expression levels of those genes in a subject in response to the subject being infected with a virus. In certain embodiments, the genes comprise those found in Table 2.

The term "appropriate treatment regimen" refers to the standard of care needed to treat a specific disease or disorder. Often such regimens require the act of administering to a subject a therapeutic agent(s) capable of producing a curative effect in a disease state. For example, a therapeutic agent for treating a subject having bacteremia is an antibiotic which include, but are not limited to, penicillins, cephalosporins, fluroquinolones, tetracyclines, macrolides, and aminoglycosides. A therapeutic agent for treating a subject having a viral respiratory infection includes, but is not limited to oseltamivir, RNAi antivirals, inhaled ribavirin, monoclonal antibody respigam, zanamivir, and neuraminidase blocking agents. The invention contemplates the use of the methods of the invention to determine treatments with antivirals or antibiotics that are not yet available. Appropriate treatment regimes also include treatments for ARIs resulting from non-infectious illness, such as allergy treatments, including but not limited to, administration of anti-histamines, decongestants, anticholinergic nasal sprays, leukotriene inhibitors, mast cell inhibitors, steroid nasal sprays etc. and asthma treatments, including but not limited to, inhaled corticosteroids, leukotriene modifiers, long-acting beta agonists, combinations inhalers (e.g., fluticasone-salmeterol; budesonide-formoterol; mometasone-formoterol, etc.), theophylline, short-acting beta agonists, ipratropium, oral and intravenous corticosteroids, omalizumab and the like.

Often such regimens require the act of administering to a subject a therapeutic agent(s) capable of producing reduction of symptoms associated with a disease state. Examples such therapeutic agents include, but are not limited to, NSAIDS, acetaminophen, anti-histamines, beta-agonists, anti-tussives, CXCR2 antagonists (e.g., Danirixin), or other medicaments that reduce the symptoms associated with the disease process.

Methods of Generating Classifiers (Training)

The present disclosure provides methods of generating a classifier(s) (also referred to as training) for use in the methods of determining the presence of and/or etiology of an ARI in a subject. In other aspects, the present disclosure provides methods for determining the etiology of an ARV in a subject. Gene, protein, or peptide expression-based classifiers have been developed that can be used to identify and characterize the presence of and/or etiology of an acute respiratory infection in a subject with a high degree of accuracy.

Hence, and as shown in FIG. 5, one aspect of the present disclosure provides a method of making an acute respiratory viral infection/illness (ARV) classifier comprising, consisting of, or consisting essentially of (i) obtaining a biological sample from a plurality of subjects suffering from acute respiratory symptoms of a known etiology; (ii) processing the gene product fraction from the biological sample (e.g., isolating protein and/or peptides from said sample to create an expressed proteome); (iii) measuring the expression levels of a plurality of the gene products (e.g., proteins and/or peptides) (i.e., some or all of the gene products expressed in the proteome); normalizing the expression levels; generating an ARV infection classifier to include normalized gene product (e.g., peptide and/or protein) expression levels and a "weighting" coefficient value; and optionally, (vi) uploading the classifier (e.g., peptide identity and weighing coefficient) to a database.

In some embodiments, the sample is not purified after collection. In some embodiments, the sample may be purified to remove extraneous material, before or after lysis of cells. In some embodiments, the sample is purified with cell lysis and removal of cellular materials, isolation of nucleic acids, and/or reduction of abundant transcripts such as globin or ribosomal RNAs.

In some embodiments, the method further includes uploading the final gene product (e.g., protein and/or peptide) target list for the generated classifier, the associated weights ($w_n$), and threshold values to one or more databases.

The methodology for training described herein may be readily translated by one of ordinary skill in the art to different gene product (e.g., protein and/or peptide) expression detection (e.g., protein/peptide detection and quantification) platforms.

The methods and assays of the present disclosure may be based upon gene products (e.g., protein and/or peptide) expression, for example, through direct measurement of proteins, measurement of derived or component materials (e.g., peptides), and measurement of other products (e.g., metabolites). Any method of extracting and screening gene product expression may be used and is within the scope of the present disclosure.

In some embodiments, the measuring comprises the detection and quantification (e.g., semi-quantification) of the gene products (e.g. proteins and/or peptides) in the sample. In some embodiments, the gene product (e.g., protein and/or peptide) expression levels are adjusted relative to one or more standard level(s) ("normalized"). As known in the art, normalizing is done to remove technical variability inherent to a platform to give a quantity or relative quantity (e.g., of expressed genes).

In some embodiments, the measurement of differential expression of specific protein or peptide molecules from biological samples may be accomplished using a range of technologies, reagents, and methods. These include direct measure of protein or peptide components using mass spectrometric technologies, or a spectrum of technologies utilizing immuno-reagents.

Protein mass spectrometry (MS) provides a tool for comprehensive proteomic survey of biological samples, as well as for targeted identification and measurement of specific protein, peptides, or metabolites. Many technical variations exist that differ in specificity, sensitivity, dynamic range, throughput, and cost, though each involve the conversion of proteins into component peptide fragments followed by their volatilization and measurement of their mass-to-charge ratio and intensity, paired with comparison to protein databases for identification. MS methods are often paired with pre-fractionation or purification (e.g. liquid chromatography) to reduce complexity of samples. One variation of targeted MS measurement, multiple/selective reaction monitoring (MRM/SRM), provides significant improvements in sensitivity and coefficients of variation, and provides opportunity for targeted measurement of multiple protein or peptide analytes. In some embodiments, the viral classifier comprises expression levels of 1, 5, 10, 15, 20, 25 or 26 of the gene products (measurable, e.g., using mass spectrometric methods or immunoreagents specific for said proteins and/or peptides) listed as part of a viral ARI classifier in Table 2. In certain embodiments, the pre-defined set of gene products comprises from 1-26 proteins and/or component peptides/epitopes of gene products listed in Table 2.

The accepted gold-standard assay for protein measurement is immunoassay, which exploits the diversity and specificity of antigen binding by immunoglobulins. In such assays, monoclonal antibodies or their antigen binding domains, or polyclonal antisera (population of immunoglobulins, are used alone (e.g. immunohistochemistry) or in combination (e.g. sandwich immunoassay) to specifically bind target protein or peptide of interest. Such assays have been developed in combination with a wide range of labeling or signal enhancement strategies to allow detection of target molecules. These include fluorescent, luminescent, colorimetric, histochemical, magnetic, radioactive, and photon scattering properties, or through change in density or mass. Assay platform using these strategies include enzyme-linked immunosorbent assays (ELISA and immunospot), flow cytometry, immunohistochemistry and immunofluorescence imaging, as well as multiplexed immunoassay platforms utilizing bead, chip, and gel substrates including lateral flow immunochromatography (e.g. pregnancy test), protein array (e.g. planar glass or silicon array), flow cytometrix microbead (e.g. Luminex), and two-dimensional (e.g. paper-based capture and signal detection) or three-dimensional matrix (e.g. hydrogel).

Hence, it should be understood that there are many methods of gene product (e.g., protein and peptide) quantification and detection that may be used by a platform in accordance with the methods disclosed herein.

The expression levels are typically normalized following detection and quantification as appropriate for the particular platform using methods routinely practiced by those of ordinary skill in the art.

With gene product (e.g., protein and/or peptide) detection and quantification and a matched normalization methodology in place for platform, it is simply a matter of using carefully selected and adjudicated patient samples for the training methods. For example, the cohort described herein below was used to generate the appropriate weighting values (coefficients) to be used in conjunction with the gene product (e.g., proteins and/or peptides) in the signature for a platform. These subject-samples could also be used to generate coefficients and cut-offs for a test implemented using a different gene products (e.g., protein and/or peptide) detection and quantification platform.

In some embodiments, the signatures may be obtained using a supervised statistical approach known as sparse linear classification in which sets of gene products are identified by the model according to their ability to separate phenotypes during a training process that uses the selected set of patient samples. The outcomes of training is a gene product (e.g., protein and/or peptide) signature(s) and classification coefficients for the classification comparison. Together the signature(s) and coefficient(s) provide a classifier or predictor. Training may also be used to establish threshold or cut-off values.

Threshold or cut-off values can be adjusted to change test performance, e.g., test sensitivity and specificity. For example, the threshold for viral ARI may be intentionally lowered to increase the sensitivity of the test for viral infection, if desired.

In some embodiments, the classifier generating comprises iteratively: (i) assigning a weight for each normalized gene product (e.g., protein and/or peptide) expression value, entering the weight and expression value for each gene product (e.g., protein and/or peptide) into a classifier (e.g., a linear regression classifier) equation and determining a score for outcome for each of the plurality of subjects, then (ii) determining the accuracy of classification for each outcome across the plurality of subjects, and then (iii) adjusting the weight until accuracy of classification is optimized Gene products (e.g. proteins and/or peptides) having a non-zero weight are included in the respective classifier.

In some embodiments, the classifier is a linear regression classifier and said generating comprises converting a score of said classifier to a probability using a link function. As known in the art, the link function specifies the link between the target/output of the model (e.g., probability of viral infection) and systematic components (in this instance, the combination of explanatory variables that comprise the predictor) of the linear model. It says how the expected value of the response relates to the linear predictor of explanatory variable.

Methods of Classification

Figure 6:
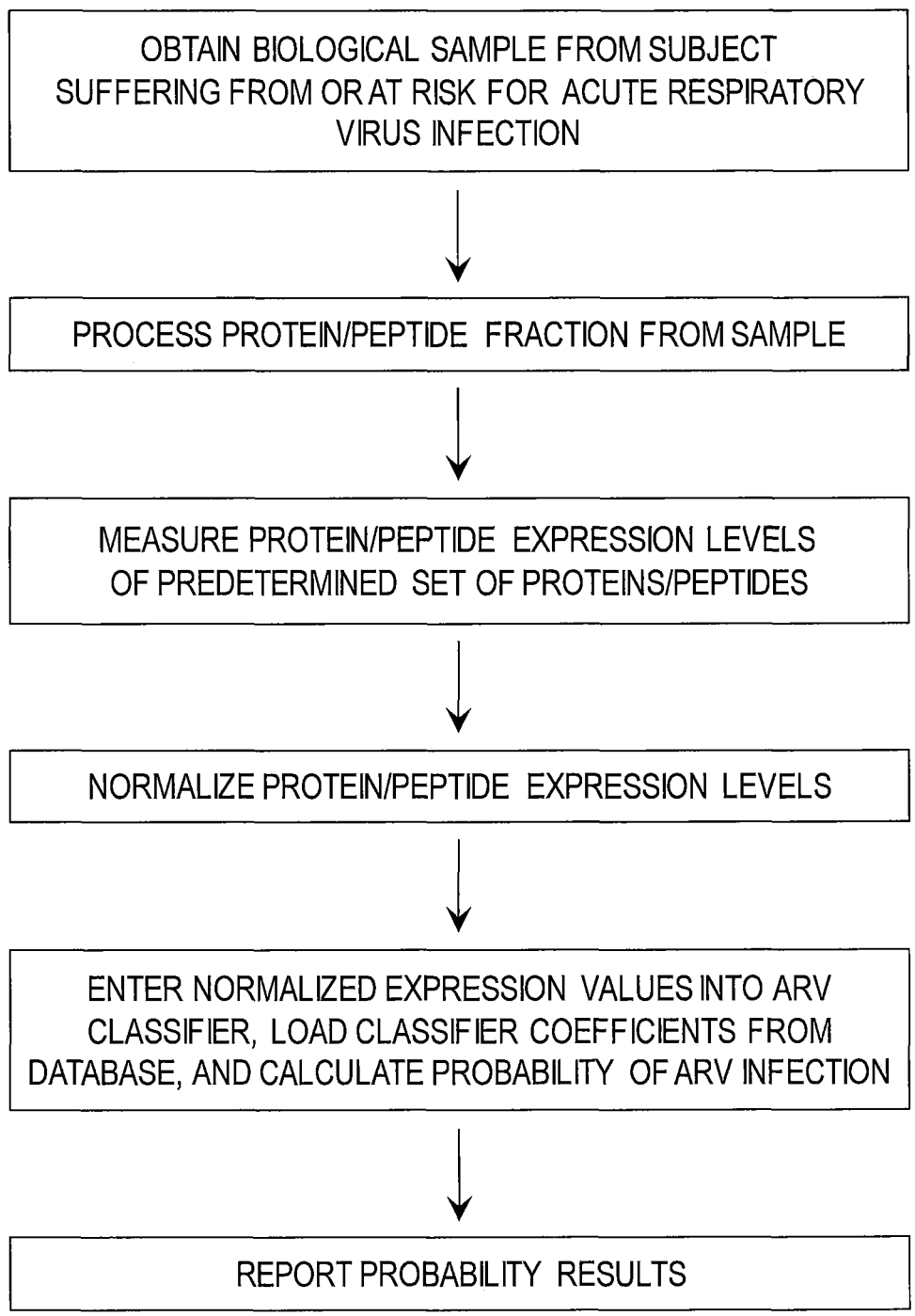
FIG. 6 is a flow chart outlining the analyzing steps in accordance with one embodiment of the present disclosure.

Another aspect of the present disclosure provides methods for determining whether a patient has a respiratory illness due to a viral infection. Further, the methods provided herein allow for one skilled in the art to determine the etiology of an acute respiratory infection/illness in a subject. The method for making this determination relies upon the use of classifiers obtained as taught herein. A simple overview is shown in FIG. 6. Such methods may include: a) measuring the expression levels of pre-defined sets of gene products b) normalizing expression levels for the technology used to make said measurement; c) taking those values and entering them into a viral classifier (i.e., predictors) that have pre-defined weighting values (coefficients) for each of the gene products in each signature; d) comparing the output of the classifier to pre-defined thresholds, cut-off values, confidence intervals or ranges of values that indicate likelihood of infection; and optionally e) jointly reporting the results of the classifiers.

These signatures are derived using carefully adjudicated groups of patient samples with the condition(s) of interest (training—FIG. 5). With reference to FIG. 6, after obtaining a biological sample from the patient (e.g., a NPL sample), in some embodiments the gene product (e.g., protein) is extracted. The gene product (e.g., protein [or a defined region of each protein, i.e. peptides]), is quantified for all, or a subset, of the genes in the signatures. Depending upon the apparatus that is used for quantification, the gene product(s) (e.g., protein or peptides) may have to be first purified from the sample.

The signature is reflective of a clinical state. For example, the viral ARI signature is defined by a group of biomarkers that distinguish patients with viral ARI from those without viral ARI (including patients with either bacterial ARI or non-infectious illness). Further, the viral ARI signature is defined by a group of biomarkers that help determine the etiology of viral infection.

Another aspect of the present disclosure provides a method for determining the etiology of an an acute respiratory viral (ARV) illness in a subject suffering therefrom, or at risk of thereof, comprising, consisting of, or consisting essentially of: (a) obtaining a biological sample from the subject; (b) measuring on a platform the gene product (e.g., protein and/or peptide) expression levels of a pre-defined set of gene products (i.e., signature) in said biological sample; (c) normalizing the gene product (e.g., protein and/or peptide) expression levels to generate normalized gene product values; (d) entering the normalized gene product (e.g., protein and/or peptide) expression values into one or more acute respiratory virus illness classifiers, said classifier(s) comprising pre-defined weighting values (i.e., coefficients)

for each of the genes of the pre-determined set of gene products for the platform, optionally wherein said classifier(s) are retrieved from one or more databases; and (e) calculating an etiology probability for one or more of a viral ARI illness based upon said normalized gene products (e.g., protein and/or peptide) expression values and said classifier(s), to thereby determine the etiology of the virus illness in the subject. In some embodiments, the determination is to identify influenza virus.

The classifiers that are developed during training and using a training set of samples are applied for prediction purposes to diagnose new individuals ("classification"). For each subject or patient, a biological sample is taken and the normalized levels of expression (i.e., the relative amount of gene product [e.g., protein or peptide] expression) in the sample of each of the gene products specified by the signatures found during training are the input for the classifier. The classifier also uses the weighting coefficients discovered during training for each gene product. As outputs, the classifiers are used to compute probability values. Each probability value may be used to determine the presence or absence of a virus (e.g., human rhinovirus (HRV), human syncytial virus (HSV), influenza, or combinations thereof) infecting, or likely to infect, the subject.

In some embodiments, these values may be reported relative to a reference range that indicates the confidence with which the classification is made. In some embodiments, the output of the classifier may be compared to a threshold value, for example, to report a "positive" in the case that the classifier score or probability exceeds the threshold indicating the presence of one or more of the viruses. If the classifier score or probability fails to reach the threshold, the result would be reported as "negative" for the respective condition.

It should be noted that a classifier obtained with one platform may not show optimal performance on another platform. This could be due to the promiscuity of probes or other technical issues particular to the platform. Accordingly, also described herein are methods to adapt a signature as taught herein from one platform for another.

Methods of Treating a Subject with an ARV

Another aspect of the present disclosure provides a method of treating an acute respiratory viral (ARV) infection/illness whose etiology is unknown in a subject, said method comprising, consisting of, or consisting essentially of (a) obtaining a biological sample from the subject; (b) determining the gene product (e.g., protein and/or peptide) expression profile of the subject from the biological sample by evaluating the expression levels of pre-defined sets of gene products; (c) normalizing gene product (e.g., protein and/or peptide) expression levels as required for the technology used to make said measurement to generate a normalized value; (d) entering the normalized values into a viral classifier (i.e., predictors) that have pre-defined weighting values (coefficients) for each of the gene products in each signature; (e) comparing the output of the classifiers to pre-defined thresholds, cut-off values, or ranges of values that indicate infection and/or likelihood of infection; (f) classifying the presence or absence of viral etiology of the infection; and (g) administering to the subject an appropriate treatment regimen as identified by step (f). In some embodiments, step (g) comprises administering an antiviral therapy.

After the etiology of the ARV of the subject has been determined, she may undergo treatment, for example antiviral therapy, and/or she may be quarantined to her home for the course of the infection.

The person performing the biological sample procurement (e.g. NPL) need not perform the comparison, however, as it is contemplated that a laboratory may communicate the gene product (e.g., protein and/or peptide) classification results to a medical practitioner for the purpose of identifying the etiology of the ARV and for the administration of appropriate treatment. Additionally, it is contemplated that a medical professional, after examining a patient, would order an agent to obtain a NPL or respiratory sample, have the sample assayed for the classifiers, and have the agent report patient's viral etiological status to the medical professional. Once the medical professional has obtained the classification result, the medical professional could order suitable treatment and/or quarantine.

The methods provided herein can be effectively used to determine the presence or absence of ARV infection in order to correctly treat the patient and reduce inappropriate use of antibiotics. Further, the methods provided herein have a variety of other uses, including but not limited to, (1) a host-based test to detect individuals who have been exposed to a pathogen and have impending, but not symptomatic, illness (e.g., in scenarios of natural spread of diseases through a population but also in the case of bioterrorism); (2) a host-based test for monitoring response to a vaccine or a drug, either in a clinical trial setting or for population monitoring of immunity; (3) a host-based test for screening for impending illness prior to deployment (e.g., a military deployment or on a civilian scenario such as embarkation on a cruise ship); and (4) a host-based test for the screening of livestock for ARV infections (e.g., avian flu and other potentially pandemic viruses).

The methods described herein are also useful in screening a population of subjects for the presence or absence of a virus in, for example, a pandemic outbreak. In such instances, quickly being able to determine whether a subject is infected with an acute respiratory virus will be critical to help prevent the spread of the virus and to administer appropriate treatment to the subject thereby increasing their chances of surviving. Hence, another aspect of the present disclosure provides a method for determining the presence or absence of a respiratory virus in a population of subjects comprising, consisting of, or consisting essentially of: (a) obtaining a biological sample from the subjects; (b) measuring on a platform expression levels of a pre-defined set of gene products (i.e., signature) in said biological samples; (c) normalizing the gene product expression levels to generate normalized expression values; (d) entering the normalized gene product expression values into one or more acute respiratory virus illness classifiers, said classifier(s) comprising pre-defined weighting values (i.e., coefficients) for each of the gene products of the pre-determined set of proteins and/or peptides for the platform, optionally wherein said classifier(s) are retrieved from one or more databases; and (e) calculating presence probability for one or more of a viral ARI illness based upon said normalized expression values and said classifier(s), to thereby determine the presence or absence of a respiratory virus in the population of subjects. In some embodiments, the methods further comprises administering an antiviral treatment to the subject(s) that have been determined to have an acute viral infection. In other embodiments, the method may further comprise quarantining those subjects determined to have an acute respiratory infection.

The methods described herein are also useful for practitioners to help determine when an antibiotic should or should not be prescribed to a subject suffering from an acute respiratory infection. Overuse and misapplication of antibacterial therapies have led to unfortunate consequences, such as the development of antibiotic resistant strains of bacteria. Thus, another aspect of the present disclosure provides a method for determining whether an antibiotic should administered to a subject suffering from a respiratory virus infection comprising, consisting of, or consisting essentially of: (a) obtaining a biological sample from the subject; (b) measuring on a platform expression levels of a pre-defined set of gene products (i.e., signature) in said biological sample; (c) normalizing the gene product expression levels to generate normalized expression values; (d) entering the normalized gene product expression values into one or more acute respiratory virus illness classifiers, said classifier(s) comprising pre-defined weighting values (i.e., coefficients) for each of the gene products of the pre-determined set of proteins and/or peptides for the platform, optionally wherein said classifier(s) are retrieved from one or more databases; and (e) calculating presence probability for one or more of a viral ARI illness based upon said normalized expression values and said classifier(s), to thereby determine the presence of a respiratory virus in the subject; and (f) not administering to the subject an antibacterial therapy if the presence of a respiratory virus is determined.

Kits

Another aspect of the present disclosure provides a kit for determining the presence or absence of viral etiology of an ARI/illness in a subject comprising, consisting of, or consisting essentially of (a) a means for extracting a biological sample; (b) a means for generating one or more arrays or assay panels consisting of a plurality of antibodies, antibody fragments, aptamers, or other analyte specific or signal-generating reagents (e.g. labeled secondary antibody) for use in measuring gene product expression levels as taught herein; and (c) instructions for use.

Another aspect of the present disclosure provides a kit for determining the presence or absence of viral etiology of an ARI illness in a subject comprising, consisting of, or consisting essentially of (a) a means for extracting a biological sample; (b) a means for measuring expression levels of one or more gene products consisting of "spike-in" labeled peptides or protein fragments (e.g. stable isotope labeled peptides) for use in relative quantitation of endogenous gene product expression levels (e.g. mass spectrometry) as taught herein; and (c) instructions for use.

Yet another aspect of the present disclosure provides a kit for detecting the presence of a respiratory virus in a subject comprising, consisting of, or consisting essentially of (a) a means for extracting a biological sample; (b) a means for generating one or more arrays consisting of a plurality of antibodies or other analyte specific reagents for use in measuring gene product expression levels as taught herein; and (c) instructions for use.

Classification Systems

Another aspect of the present disclosure provides a classification system and/or computer program product that may be used in or by a platform, according to various embodiments described herein. A classification system and/or computer program product may be embodied as one or more enterprise, application, personal, pervasive and/or embedded computer systems that are operable to receive, transmit, process and store data using any suitable combination of software, firmware and/or hardware and that may be stand-alone and/or interconnected by any conventional, public and/or private, real and/or virtual, wired and/or wireless network including all or a portion of the global communication network known as the Internet, and may include various types of tangible, non-transitory computer readable medium.

In one embodiment, the classification system may include a processor subsystem, including one or more Central Processing Units (CPU) on which one or more operating systems and/or one or more applications run. The processor(s) may be either electrically interconnected or separate. Processor(s) are configured to execute computer program code from memory devices, such as memory, to perform at least some of the operations and methods described herein, and may be any conventional or special purpose processor, including, but not limited to, digital signal processor (DSP), field programmable gate array (FPGA), application specific integrated circuit (ASIC), and multi-core processors.

The memory subsystem may include a hierarchy of memory devices such as Random Access Memory (RAM), Read-Only Memory (ROM), Erasable Programmable Readonly Memory (EPROM) or flash memory, and/or any other solid state memory devices.

A storage circuit may also be provided, which may include, for example, a portable computer diskette, a hard disk, a portable Compact Disk Read-Only Memory (CDROM), an optical storage device, a magnetic storage device and/or any other kind of disk- or tape-based storage subsystem. The storage circuit may provide non- volatile storage of data/parameters/classifiers for the classification system. The storage circuit may include disk drive and/or network store components. The storage circuit may be used to store code to be executed and/or data to be accessed by the processor. In some embodiments, the storage circuit may store databases that provide access to the data/parameters/classifiers used for the classification system such as the signatures, weights, thresholds, etc. Any combination of one or more computer readable media may be utilized by the storage circuit. The computer readable media may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. As used herein, a computer readable storage medium may be any tangible medium that can contain, or store a program for use by or in connection with an instruction execution system, apparatus, or device.

An input/output circuit may include displays and/or user input devices, such as keyboards, touch screens and/or pointing devices. Devices attached to the input/output circuit may be used to provide information to the processor by a user of the classification system. Devices attached to the input/output circuit may include networking or communication controllers, input devices (keyboard, a mouse, touch screen, etc.) and output devices (printer or display). The input/output circuit may also provide an interface to devices, such as a display and/or printer, to which results of the operations of the classification system can be communicated so as to be provided to the user of the classification system.

An optional update circuit may be included as an interface for providing updates to the classification system, Updates may include updates to the code executed by the processor that are stored in the memory and/or the storage circuit. Updates provided via the update circuit may also include updates to portions of the storage circuit related to a database and/or other data storage format which maintains information for the classification system, such as the signatures, weights, thresholds, etc.

The sample input circuit of the classification system may provide an interface for the platform as described hereinabove to receive biological samples to be analyzed. The sample input circuit may include mechanical elements, as well as electrical elements, which receive a biological sample provided by a user to the classification system and transport the biological sample within the classification system and/or platform to be processed. The sample input circuit may include a bar code reader that identifies a bar-coded container for identification of the sample and/or test order form. The sample processing circuit may further process the biological sample within the classification system and/or platform so as to prepare the biological sample for automated analysis. The sample analysis circuit may automatically analyze the processed biological sample. The sample analysis circuit may be used in measuring, e.g., gene product levels of a pre-defined set of proteins and/or peptides with the biological sample provided to the classification system. The sample analysis circuit may also generate normalized expression values by normalizing the gene product (e.g., protein and/or peptide) expression levels. The sample analysis circuit may retrieve from the storage circuit an ARV infection/illness classifier comprising pre-defined weighting values (i.e., coefficients) for each of the gene products (e.g., proteins and/or peptides) of the pre-defined set of gene products. The sample analysis circuit may enter the normalized expression values into one or more acute respiratory illness classifiers selected from the ARV classifier. The sample analysis circuit may calculate an etiology probability for one or more of an AVR based upon said classifier(s) and control output, via the input/output circuit, of a determination of presence or absence of viral etiology of ARI/illness, or some combination thereof.

The sample input circuit, the sample processing circuit, the sample analysis circuit, the input/output circuit, the storage circuit, and/or the update circuit may execute at least partially under the control of the one or more processors of the classification system. As used herein, executing "under the control" of the processor means that the operations performed by the sample input circuit, the sample processing circuit, the sample analysis circuit, the input/output circuit, the storage circuit, and/or the update circuit may be at least partially executed and/or directed by the processor, but does not preclude at least a portion of the operations of those components being separately electrically or mechanically automated. The processor may control the operations of the classification system, as described herein, via the execution of computer program code.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the classification system, partly on the classification system, as a stand-alone software package, partly on the classification system and partly on a remote computer or entirely on the remote computer or server. In the latter scenario, the remote computer may be connected to the classification system 1 100 through any type of network, including a local area network (LAN) or a wide area network (WAN), or the connection may be made to an external computer (for example, through the Internet using an Internet Service Provider) or in a cloud computer environment or offered as a service such as a Software as a Service (SaaS).

In some embodiments, the system includes computer readable code that can transform quantitative, or semi-quantitative, detection of gene expression to a cumulative score or probability of the etiology of the AVR.

In some embodiments, the system is a sample-to-result system, with the components integrated such that a user can simply insert a biological sample to be tested, and some time later (preferably a short amount of time, e.g., 30 or 45 minutes, or 1, 2, or 3 hours, up to 8, 12, 24 or 48 hours) receive a result output from the system.

It is to be understood that the present disclosure is not limited in its application to the details of construction and the arrangement of components set forth in the following description or illustrated in the following drawings. The present disclosure is capable of other embodiments and of being practiced or of being carried out in various ways.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the present disclosure.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Yet another aspect of the present disclosure provides all that is disclosed and illustrated herein. The following examples are illustrative only and are not intended to be limiting in scope.

EXAMPLES

Example 1. Nasopharyngeal Protein Biomarkers of Acute Respiratory Virus Infection Infection of respiratory mucosa with viral pathogens triggers a complex cascade of immunologic events in the affected host. We sought to characterize this cascade through proteomic analysis of nasopharyngeal lavage in human subjects experimentally challenged with influenza A/H3N2 or human rhinovirus, and to develop targeted assays measuring peptides involved in this host response allowing classification of acute respiratory virus infection. Unbiased proteomic discovery analysis identified 3285 peptides corresponding to 438 unique proteins, and revealed that infection with H3N2 induces significant alterations in protein expression. These include proteins involved in acute inflammatory response, innate immune response, and complement cascade. In addition to providing insights into the nature of the biological response to viral infection of the upper respiratory tract, the most significantly altered proteins can be combined into a proteomic signature that accurately classifies the infected state. Verification of this signature using targeted mass spectrometry in independent cohorts of subjects challenged with either influenza or rhinovirus demonstrates that it performs with a high degree of accuracy (0.8623 AUROC, 75% TPR, 97.46% TNR). With further development as a clinical diagnostic, this signature may have utility in rapid screening for emerging infections, avoidance of inappropriate antimicrobial therapy, and more rapid implementation of appropriate therapeutic and public health strategies.

1. Introduction

Acute respiratory viral (ARV) infections are among the most common reasons for patient visits in primary and acute care settings (Hong et al., 2004; Johnstone, Majumdar, Fox, & Marrie, 2008). Many viruses cause such acute respiratory illness including human rhinovirus (HRV), respiratory syncytial virus (RSV) and influenza. These viruses can be associated with a range of clinical severity from being largely asymptomatic to mild, self-limited illness to respiratory failure and death. Influenza alone causes 25 to 50 million infections annually in the USA, resulting in several hundred thousand hospitalizations and 20-40,000 deaths (Thompson et al., 2010).

Despite viral etiologies driving most cases of acute respiratory infection, definitive diagnostic tools for these syndromes are lacking. Even highly sensitive pathogen-specific tests such as PCR are dependent upon proper sampling technique and inclusion of virus-type-specific reagents and processing methods. Moreover, detection of a specific microbe in a clinical sample does not necessarily indicate the cause of the acute clinical syndrome. For example, it has been reported that HRV has been detected in up to 44% of asymptomatic individuals (Byington et al., 2015; Johnston et al., 1993). Therefore, better tools that help providers define the etiology of a suspected infectious syndrome in a safe, rapid, accurate, and cost-effective manner are of paramount importance for both individual and public health as recently noted by the Presidential Advisory Council on Combating Antibiotic-Resistant Bacteria (House, 2014), and others (O'Neill, 2015; Organization, 2015). A complementary diagnostic strategy to pathogen detection could focus on utilizing the varied (but pathogen-class specific) host-response to infection (Ramilo & Mejias, 2009; A. K. Zaas et al., 2014).

This approach discriminates between infection and colonization. It is pathogen-agnostic and therefore circumvents another limitation of pathogen detection assays, which due to technical limitations are only capable of detecting a limited subset of microorganisms. Furthermore, categorizing infection based on host response provides additional insights into the mechanisms of infection and disease response, and may offer new targets, pathways, or strategies for therapeutic intervention.

We recently identified gene expression patterns in peripheral whole blood capable of differentiating (Huang et al., 2011; McClain et al., 2016; Tsalik et al., 2016; Woods et al., 2013; A. K. Zaas et al., 2009) individuals with symptomatic infection due to influenza H3N2, HRV, or RSV from uninfected individuals with >90% accuracy. Moreover, this ARV signature was validated in an independent population of patients with influenza A infection, demonstrating an ability to distinguish from bacterial respiratory infections (93% accuracy) and healthy controls (100% accuracy) (A. K. Zaas et al., 2009). Thus, host derived biomarkers have been shown to be capable of making these types of distinction. However, considering the technical challenges inherent in developing peripheral blood host gene expression classifiers as a diagnostic tool—including semi-invasive venipuncture, RNA instability, processing complexity, relatively high cost of RNA profiling, and time to result—we sought to extend this host response paradigm for ARV diagnosis to an alternative and potentially more suitable sample matrix and analyte class.

Upon contact with the respiratory epithelium, respiratory viruses incite activation of type I interferons (IFNs) and pro-inflammatory cytokines, orchestrate proliferation of inflammatory cells and the innate immune response, and regulate induction of adaptive immunity (Bhoj et al., 2008; Koyama, Ishii, Coban, & Akira, 2008; Yoneyama & Fujita, 2010). Based on the prominent role of the nasopharyngeal epithelium in mediating ARV infections, we hypothesized that nasopharyngeal lavage (NPL) would reflect the in situ host response and serve as a potential target for diagnostic development. Furthermore, the NPL protein fraction represents an accessible sample matrix, providing a highly tractable diagnostic analyte class. Multiple reaction monitoring (MRM), a quantitative mass spectrometry (MS) platform for facile development of multiplexed, quantitative assays for measuring specific protein levels in biologic fluids and is routinely used for biomarker verification in clinical cohorts (Boja & Rodriguez, 2011; Gerszten, Can, & Sabatine, 2010; Kiyonami et al., 2011). In addition to being customizable for nearly any target protein, MRM assays provide a more specific quantitation of individual proteins and protein isoforms by targeting multiple unique peptides per protein target. Combined with internal stable-isotope labeled (SIL) peptide standards, these assays match or exceed the quantitative precision of ELISA assays with low femtomole limits of quantitation and analytical precision coefficient of variation<10% across clinically sized cohorts (Addona et al., 2009; Aebersold, Burlingame, & Bradshaw, 2013).

Using human viral challenge cohorts for influenza A/H3N2 and HRV, we have discovered and independently verified multiple NPL protein biomarkers capable of classifying human influenza A and HRV infection from uninfected individuals. This work reinforces the important concept that host response to infection, particularly in the NPL proteome, serves as a potential basis for diagnostic testing. It also sheds light on the complex interactions of host and pathogen in two of the most common infectious diseases in humans.

2. Materials and Methods 2.1 Study Design

All pathogen exposures were approved by the relevant Institutional Review Boards and conducted according to the Declaration of Helsinki. All volunteers provided informed consent. The objective of these experimental challenge studies was to generate clinico-molecular classifiers of ARV infection through the development and characterization of high-density sample and data sets across the course of respiratory virus exposure, infection, and resolution. A description of methods used in each challenge study can be found in Supplementary Materials and have been described previously (Liu et al., 2016; McClain et al., 2016; Woods et al., 2013; A. K. Zaas et al., 2009). Briefly, healthy volunteers underwent extensive pre-enrollment health screening and were excluded for positive baseline antibody titers of the strain of virus used in each challenge (Influenza A H3N2 A/Wisconsin/67/2005 or HRV serotype 39). Following 24-48 hours in quarantine, we instilled viral inoculum into bilateral nares of subjects using standard methods. At predetermined intervals, biological samples and clinical/symptom data were collected. NPL sampling was performed daily for each participant. The H3N2 #2 cohort included an early (36 hour post-inoculation) oseltamivir treatment arm, while HRV #2 included a blinded "sham" inoculation (saline only) control group. NPL analyses included baseline and time T samples from all individuals in each challenge study with complete and unambiguous symptomatology and microbiology data, and available NPL samples. Sample phenotype labels were blinded for MRM analysis, but were assayed in a manner to ensure that samples from an individual, and from within a challenge study, would be processed in same batch and assayed in close temporal proximity, to minimize batch effects between distinct phenotypes.

2.2 Case Definitions

Self-reported symptoms were recorded at predetermined intervals prior to inoculation and at least twice daily throughout the time-course of infection and resolution as reported previously (Jackson, Dowling, Spiesman, & Boand, 1958; A. K. Zaas et al., 2009) and described in Supplementary Materials. This modified Jackson score requires subjects to rank 8 symptoms of upper respiratory infection (headache, sore throat, rhinorrhea, rhinitis, sneezing, coughing, myalgia, malaise) on a standardized scale of 0 (no symptoms) to 3 (high symptoms). Symptom scores were tabulated for each study participant to assign symptom status as symptomatic or asymptomatic (Supplementary Table S2A). For each symptomatic subject, time T was identified as time of maximal symptoms. The average time T was then defined for that cohort, which served as the time chosen for asymptomatic subjects (Table 1). Participants were tested for virus shedding based on quantitative culture assays as described previously (A. K. Zaas et al., 2009) and outlined in Supplementary Table S2B. For the purpose of the current analysis, we differentiated between "symptomatic" and "shedding". A symptomatic subject shedding virus was labeled as "infected". Asymptomatic non-shedders were "uninfected". Discordance between symptom and shedding status were reconciled by measuring a previously published peripheral blood gene expression score, as described in supplementary materials. This tiebreaker was a gene expression analysis (GEA) representing the host peripheral blood response to viral infection (Supplementary Table S2C) (Hero, Arzouni, McClain, & Burke). GEA was only applied as a tiebreaker and not to subjects where the symptom and shedding status agreed.

2.3 Sample Collections

Sample collections for subjects in H3N2 cohort #1 and HRV cohort #1 have been described previously (A. K. Zaas et al., 2009). Samples for H3N2 cohort #2 and HRV cohort #2 were collected, processed, and analyzed similarly. Briefly, biological samples were collected prior to inoculation (baseline) and at predetermined intervals throughout the course of infection and resolution. Nasopharyngeal lavage procedures were performed using sterile 0.9% saline solution (5 ml into each nares), as described in Supplementary Materials, prior to inoculation and at 24-hour intervals post-inoculation and stored in aliquots at −80° C. This study focused on comparison of pre-inoculation (baseline) samples with samples taken at or shortly following time T.

2.4 Unbiased 2D-LC-MS/MS

NPL samples were processed for proteomic analyses as described in Supplementary Materials. For the pooled 2D-LC-MS/MS discovery analysis, four sample pools were created representing the four groups in H3N2 #1 challenge—Uninf-BL (n=4), Uninf-T (n=6), Inf-BL (n=6), and Inf-T (n=8)—with equal protein mass (2 ug) from each participant. Normalized pooled samples (2D-LC-MS/MS) and individual participant samples (MRM) were reduced, alkylated, and digested with trypsin as described in Supplementary Materials. Prior to analysis, all samples were spiked with ADH1_YEAST digest (Massprep standard, Waters Corporation) as an internal technical standard. Unbiased proteomic discovery analysis was performed using Nanoscale Capillary UPLC-MS/MS as described in Supplementary Materials. Briefly, quantitative 10-fraction 2D-LC-MS/MS was performed on duplicate injections for each sample pool, providing accurate mass and intensity (abundance) acquisitions with qualitative identification of the resulting peptide fragments via searching against a SwissProt_Human (www.uniprot.org) database that also contained a reversed-sequence "decoy" database for false positive rate determination. Analytical reproducibility of the label-free 2D-LC-MS/MS method was assessed by calculating the variation in measured abundance of the spiked ADH1_YEAST standard, demonstrating a coefficient of variation of 10.6% across all eight injections. For quantitative processing, peptide quantities across all ten 2D-LC fractions were summed and the dataset was intensity-scaled to the robust mean (excluding highest and lowest 10% of detected features) across all quantitative acquisitions. The final quantitative dataset for NPL was based on 3285 peptides and contained 438 unique proteins.

2.5 Targeted MRM

Following the selection of 25 candidate protein targets from the unbiased discovery data, all individual samples were subjected to a targeted MRM assay as detailed in Supplementary Materials. MRM assay development and transition selection was performed within the open-access Skyline (MacCoss Laboratory, Univ of Washington) software. Initially, up to five unique peptides were selected from each candidate protein based on average precursor ion intensity. Five transitions for each precursor ion were selected based on 1) qualitative DDA discovery MS/MS data, 2) other discovery datasets for which the same peptide sequence was identified or 3) from the PeptideAtlas (ww. PeptideAtlas.org) public repository. Following deployment of the initial MRM assay on a healthy human control NPL pool, the MRM method was optimized to choose three transitions from the two most robust peptides per protein.

Figure 7A:
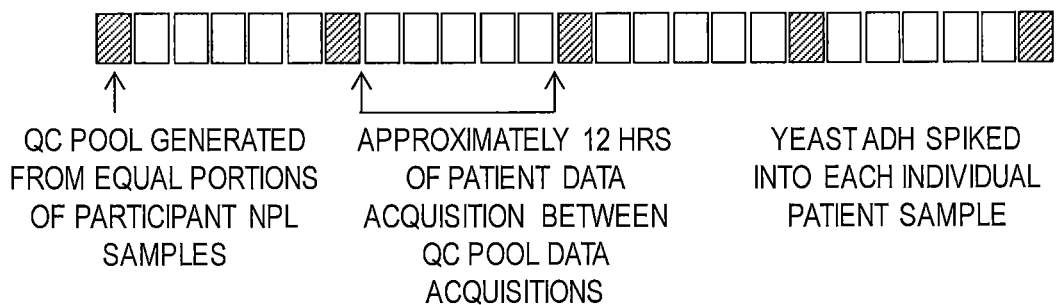
FIG. 7A-FIG. 7C provide MRM Data acquisition design and reproducibility metrics. MRM data acquisition strategy (FIG. 7A) includes assay of QC pool (filled boxes) approximately every 12 hrs of data acquisition time, with spiked exogenous Yeast ADH peptides (open boxes) spiked into each individual sample.
Figure 7B:
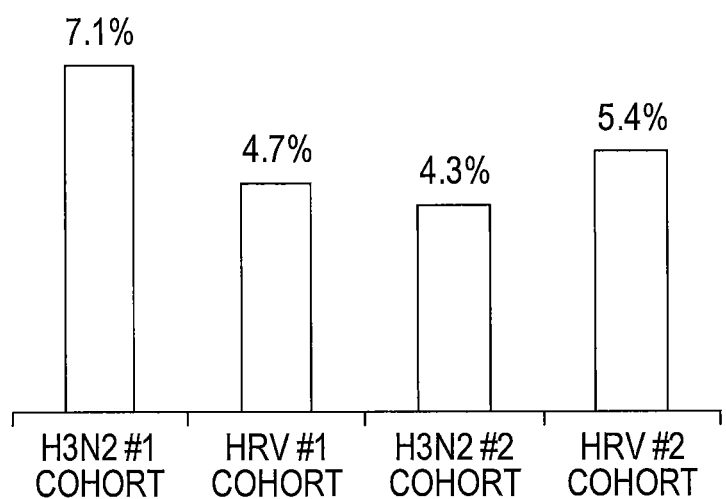
Figure 7C:
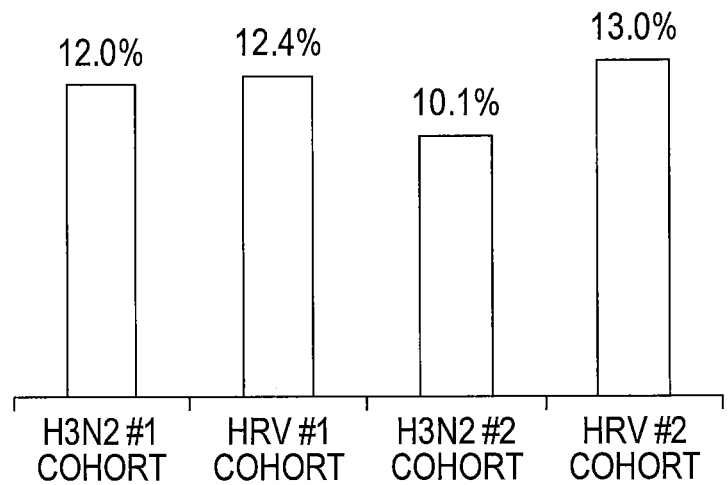

Custom SIL peptides were ordered for each candidate peptide to be assayed, and were spiked into each individual digested NPL participant sample at one of four ratios relative to endogenous peptide as described in Supplementary Materials. Each of the four patient cohorts (two H3N2 and two HRV) was run as individual run blocks and samples within a cohort were randomized in injection order across the cohort. Single MRM assays were performed on spiked NPL samples with a target quantity of up to 1 ug on-column. Four samples (3 from H3N2 #1 and 1 from H3N2 #2) were prepared and MRM quantification was attempted, but did not have sufficient protein material to generate robust quantitative data and therefore were excluded from subsequent analyses. To assess analytical variation, an equal portion of each patient's SIL spiked NPL sample was used to generate a QC pool, which was run approximately every 12 hrs across the entire cohort. In addition, all samples were spiked with five SIL peptides from yeast_ADH as an internal technical control. MRM assay reproducibility metrics are shown in FIG. 7A-FIG. 7C.

2.6 Data Processing

We examined 51 human peptide analytes (plus 5 yeast ADH) from 26 different human proteins. Eighty subjects from the four viral challenge studies were assayed although four subjects had insufficient NPL material at one time point resulting in 156 samples. Four peptides with >2 missing values were excluded from analysis. Missing values and zeroes (11 sample-analytes) were imputed with half the observed minimum value of a given peptide, and expression levels from the remaining 47 peptides were log transformed and carried forward for further analysis. Simple batch (study) correction was performed by removing study-wise mean values from each peptide. Final analysis included 47 human peptides measured in 156 samples.

2.7 Statistical Analysis

Univariate testing was performed using two-sided t-tests with Benjamini-Hochberg FDR corrected p-values. For classification we used sparse logistic regression, in particular a Least Absolute Shrinkage and Selection Operator (LASSO) generalized linear model with binomial likelihood (Friedman, Hastie, & Tibshirani, 2010). Performance metrics and model parameters were obtained via nested leave-one-out cross-validation (LOOCV). As classification performance metrics we consider area under receiver operating curve (AUROC) (Fawcett, 2006), true positive rate (TPR), and true negative rate (TNR). A 17 protein (30 peptide) relaxed classifier ($\alpha=0.1$ rather than 1.0) was subjected to pathway association analysis using DAVID 6.7 Functional Annotation Tool (Huang da, Sherman, & Lempicki, 2009) using UniProt accession identifiers and human background.

3. Results

3.1 Influenza A/H3N2 and Human Rhinovirus Challenge Cohorts

Four independent viral challenge studies were conducted (Table 1)—two challenges with influenza A/H3N2 and two with HRV, and were described previously (McClain et al., 2016; Woods et al., 2013; A. K. Zaas et al., 2009). Clinical and self-reported symptom data, along with corresponding samples, were collected multiple times per day across the course of exposure, infection, and resolution. For each challenge participant, standardized algorithms were applied to assign phenotype labels describing symptomatic, shedding, and "infected" status (Supplementary Tables S2A, S2B, S2C, respectively) across the time-course. Since symptom and shedding status were not always congruent, we required that both be present to define a patient as "infected". When both were absent, that subject was labeled "uninfected". When discordant, we applied a tiebreaker based on gene expression analysis (GEA) representing the host peripheral blood response to viral infection (Supplementary Table S2C) (Hero et al.). Of the 80 challenge participants included in this analysis, just over half (42/80) of the participants were adjudicated as becoming infected (H3N2 #1: 9 of 15 infected; H3N2 #2: 10 of 21; HRV #1: 10 of 20; and HRV #2: 13 of 24).

TABLE 1

Description of experimental ARV challenge cohorts

| Cohort | H3N2 #1 | H3N2 #2 | HRV #1 | HRV #2 |
|---|---|---|---|---|
| Subjects included in challenge | 17 | 21 | 20 | 30 |
| Subjects included in NPL analysis | 15 | 21 | 20 | 24 |
| Symptomatic | 9 | 13 | 12 | 15 |
| Shedding positive | 10 | 10 | 12 | 15 |
| Number discordant[1] | 1 | 7 | 4 | 9 |
| Mean Sx time T (in hrs) | 69 | 68 | 66 | 76 |
| Corresponding Asx time T (in hrs) | 69.5 | 71 | 72 | 72 |

[1]Individuals with discordant symptom and shedding labels, i.e. symptomatic non-shedders, or asymptomatic shedders.
NPL = Nasopharyngeal lavage.
Sx = Symptomatic.
Asx = Asymptomatic.
Time T represents the time of maximal symptoms.

Table 1. Description of experimental ARV challenge cohorts. Four experimental HRV challenge cohorts (two influenza A/H3N2 and two HRV) are described, including adjudicated phenotype summary data for each. Individuals with discordant[1] symptom and shedding labels, i.e. symptomatic non-shedders, or asymptomatic shedders, are shown. Sx=symptomatic; Asx=asymptomatic; mean Sx and Asx time T represents the average time of maximal self-reported symptoms among subject included in NPL analysis.

3.2 Proteomics Discovery and Verification Strategy

An overview of the proteomic discovery and candidate biomarker verification strategy is depicted in FIG. 1. Despite being a readily accessible matrix, one technical challenge of studying NPL is the variability in protein yield from subject to subject. To overcome this limitation, we utilized a two-phase biomarker discovery strategy: The first phase used pooled NPL samples from a single H3N2 challenge for in-depth MS-based discovery proteomics to assist in identification and prioritization of candidate biomarkers. In the second phase, targeted assays were developed for these candidates using the more sensitive and quantitatively reproducible MRM approach. Verification of the utility of the markers was then performed in the original and three independent challenge cohorts using targeted MRM quantitation.

3.3 Identification of Candidate Protein Biomarkers Using Pooled NPL from H3N2 Challenge Study Discovery proteomics was performed on the H3N2 #1 challenge cohort using open-platform, 2-dimensional liquid chromatography, tandem MS (2D-LC-MS/MS) analysis of four sets of pooled NPL samples (uninfected and infected individuals at baseline and time of maximal symptoms, time T) using equal protein mass per participant sample. Across the four unique NPL sample pools, a total of 3285 peptides corresponding to 438 unique proteins were identified at a 1.0% peptide-level false discovery rate (FDR).

We next investigated the variable expression of NPL proteins in infected and uninfected viral challenge pooled samples. Three criteria were used to prioritize suitable peptides for subsequent MRM quantification from the entire collection of 438 identified NPL proteins (Supplementary Table S3). First, we sought a minimum two-fold change in expression between baseline and time T in the infected pool in at least 2 peptides/protein; this criterion was used to classify proteins that would increase or decrease as a function of infection within the same individuals over time. Levels of 107 proteins increased at least two-fold, while 61 proteins decreased at least two-fold from baseline to time T. The second criterion was a greater than two-fold difference between infected and time-matched uninfected subjects; this criteria was to enable specificity of the proteins by comparing test and control subjects at a time where symptoms are present. This included 36 proteins with higher expression and 33 proteins with lower expression. The third criterion excluded proteins that might reflect general nasal trauma stemming from repeated collections. To address this, we calculated the expression change between the time of maximal symptoms for infected subjects (Inf-T) relative to similar times for uninfected subjects (Uninf-T), and prioritized candidates with unique response to infection at time T. Additionally, four proteins met 2 of 3 criteria and also had a reported association with infection (IC1) (A. K. Zaas et al., 2009) and inflammation (APOA1, APOA2, and APOA4) (Pirillo, Catapano, & Norata, 2015) and were included in the verification phase. Based on these criteria, 25 proteins were selected for subsequent MRM assay development—13 had increased and 12 had decreased expression in infected participants.

3.4 MRM Quantification of Candidate Biomarkers in Individual NPL Samples

MRM is a quantitative LC-MS/MS method utilizing synthetic, SIL peptides as internal standards, and provides absolute specificity for the target analyte and relative abundance measurements (Addona et al., 2009; Kiyonami et al., 2011). A total of 51 unique peptide MRM assays were designed to target two unique peptides for each of the 25 prioritized candidate biomarker proteins, plus human serum albumin. and yeast alcohol dehydrogenase as a spiked exogenous control. Two proteins yielded only a single peptide that was suitable for an MRM assay—Statherin (only one viable SIL peptide could be synthesized) and Filaggrin (one of two SIL peptides was insoluble). A third protein, Calcyphosin, yielded a third suitable peptide assay from the publicly available PeptideAtlas database.

Following development, MRM assays were performed on 156 individual NPL samples from 80 subjects across four viral challenge study cohorts. This included the original influenza H3N2 cohort (H3N2 #1), a second H3N2 cohort (H3N2 #2), and two HRV challenge cohorts (HRV #1 and #2). From the original set of 51 human , peptide assays designed, 47 peptides representing 26 proteins were successfully measured.

Figure 2A:
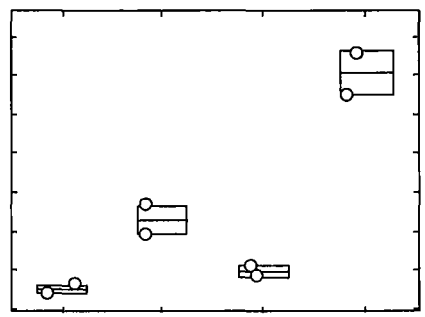
FIG. 2A-FIG. 2B are graphs showing the comparison of expression levels of peptides from 4 proteins (CFAB, TIG1, TBA1B, STAT) in H3N2 #1 challenge cohort as measured by (FIG. 2A) LC/LC-MS/MS unbiased discovery methods in sample pools (duplicate measures of multi-peptide meta-protein is shown), and (FIG. 2B) targeted MRM analysis of unique peptides from individual participant samples in accordance with one embodiment of the present disclosure. Four representative proteins (CFAB, TIG1, TBA1B, STAT) in H3N2 #1 challenge cohort were measured by LC/LC-MS/MS unbiased discovery methods in sample pools (duplicate measures of multi-peptide meta-protein is shown), and targeted MRM analysis of unique peptides (EAGIPE-FYDYDVALIK (SEQ ID NO:28); YGLVTYATYPK (SEQ ID NO:27); VHVVFSTER (SEQ ID NO:47); VLAEVQEGR (SEQ ID NO:46); IHFPLATYAPVISAEK (SEQ ID NO:52); AVFVDLEPTVIDEVR (SEQ ID NO:51); FGYGYGPYQPVPEQPLYPQPYQPQYQQYTF (SEQ ID NO:50)) from individual participant samples from the same H3N2 #1 cohort. MRM data are expressed as relative ratio (endogenous "light" peptide to spiked SIL "heavy" peptide). Box-and-whisker plots for each group indicate intra-quartile range (box) with upper and lower (whisker) values representing 99% data coverage. Circles represent uninfected (Uninf) and infected (Inf) individuals at baseline (BL, prior to inoculation with virus) and time of maximal symptoms (T). Uninf-BL=participants at baseline (prior to inoculation with virus) who do not go on to become infected. Uninf-T=uninfected at equivalent time T (matched time to time T of infected individuals). Inf-BL=participants at baseline (prior to inoculation with virus) for individuals who go on to become infected. Inf-T=infected at time of maximal symptoms.
Figure 2A:
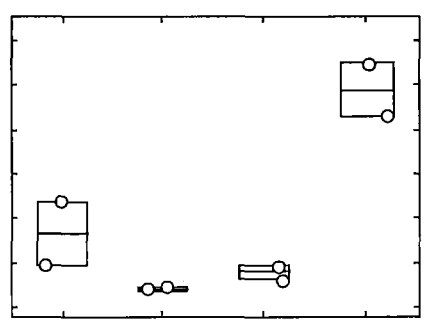
Figure 2A:
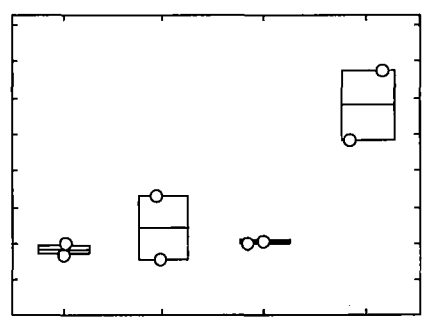
Figure 2A:
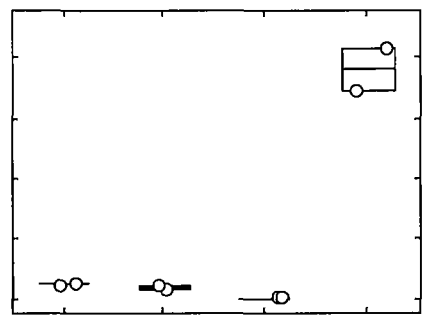
Figure 2B:
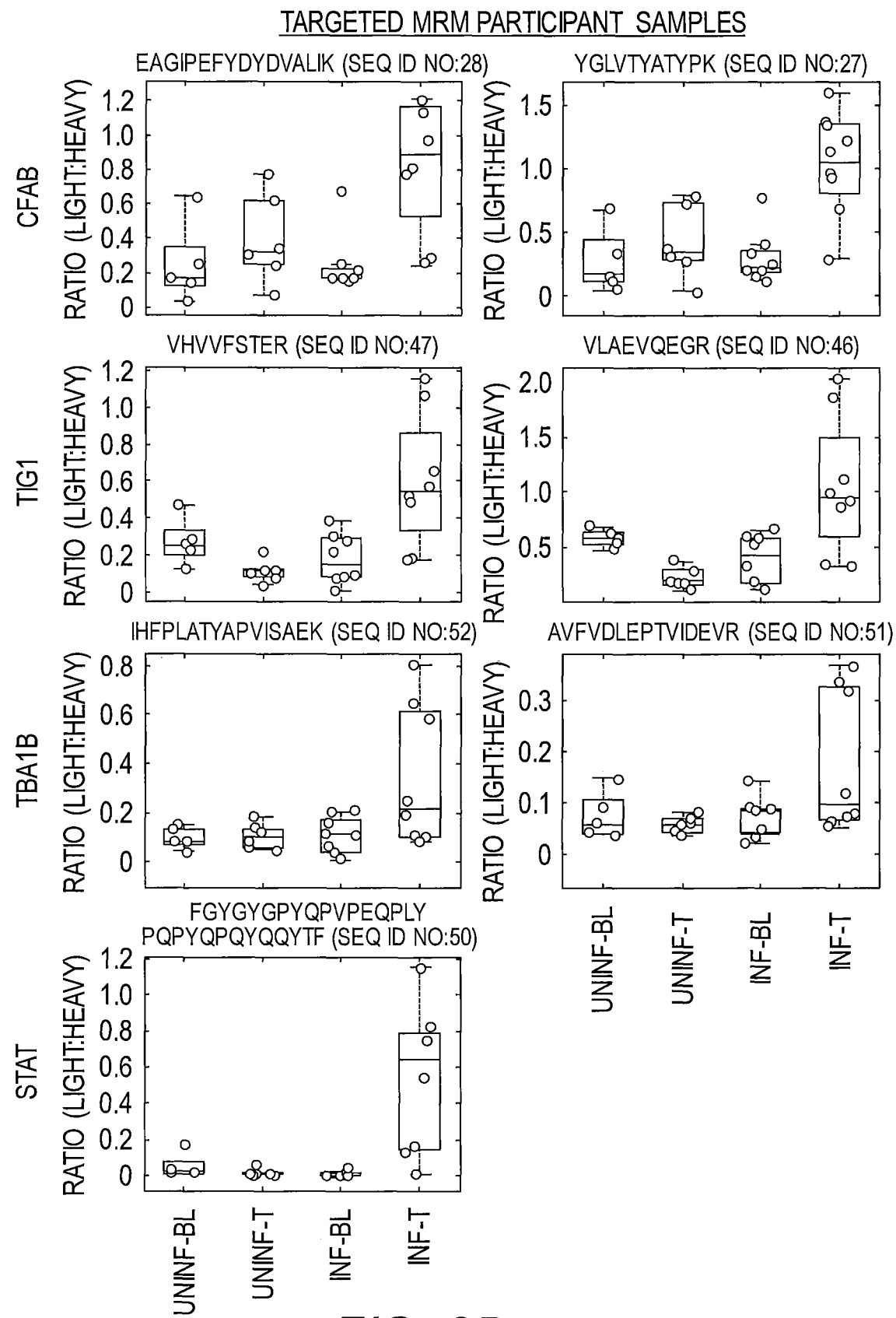

For the H3N2 #1 cohort, we observed that both the direction and magnitude of change in protein expression was consistent between the initial pooled discovery measurements (FIG. 2A) and the targeted MRM peptide measurements (FIG. 2B). This was expected, since the pooled sample is the biological average of all samples included in the pool. For example, retinoic acid receptor responder protein TIG1 was measured across three unique peptides in the pooled discovery data set, with an average fold change from uninfected to infected time T of 3.3-fold. Targeted MRM assays developed for two TIG1 peptides demonstrated average increased expression of 2.3- and 2.0-fold when assayed in individual NPL samples (Table 2). Similarly, two complement factor B (CFAB) peptides displayed 2.0- and 2.0-fold increased expression when assayed in individual H3N2 #1 samples by MRM, compared to a 3.6-fold increase for the summed 24-peptide CFAB protein composite assayed in the pooled H3N2 #1 discovery dataset. Also as expected, the pooled discovery dataset shows much more narrow standard deviation (FIG. 2A), as this deviation is due only to technical variability, whereas the variability in the targeted MRM experiment of all individuals (FIG. 2B) is able to discern the actual biological variation. These combined results provided confidence that the pooled-sample 2D-LC-MS/MS phase 1 discovery strategy gives a good measure of the average protein expression level in situations where the matrix of interest is extremely sample-limited, and that the phase 2 targeted MRM assays reproduce protein expression changes candidates selected using the pooled data, while also providing biological variance with higher sensitivity.

TABLE 2

Expression ratios for 26 candidate biomarker proteins in pooled discovery and targeted MRM assays

| UniProt Gene Symbol/ Protein Name | Unbiased Pool Peptides | UNBIASED (POOL) H3N2 #1 [3]Criterion | | | Targeted MRM Peptides | TARGETED MRM (INDIVIDUAL) H3N2 #1/2 and HRV #1/2 [4]Fold change $[T/BL]_{Inf}$ (FDR) |
|---|---|---|---|---|---|---|
| | | 1 | 2 | 3 | | |
| CFAB/Complement factor B | 34 | 3.6 | 2.1 | 1.6 | 2 | 2.0, 2.0 (1.8e−4, 2.2e−4) |
| IC1/Plasma protease C1 inhibitor | 8 | 6.4 | 1.8 | 1.0 | 2 | 1.3, 1.8 (0.089, 3.9e−4) |
| A1AT/Alpha-1-antitrypsin | 100 | 5.1 | 2.1 | 1.3 | 2 | 1.7, 1.7 (7.8e−4, 5.0e−4) |
| A1AG1/Alpha-1-acid glycoprotein 1 | 19 | 4.1 | 2.6 | 1.1 | 2 | 1.8, 1.8 (3.9e−4, 3.9e−3) |
| ALB/Albumin | 805 | 2.4 | 1.4 | 1.0 | 2 | 1.5, 1.6 (7.8e−4, 7.8e−4) |
| TIG1/Retinoic acid receptor responder prot 1 | 3 | 3.3 | 4.2 | 5.7 | 2 | 2.3, 2.0 (6.2e−4) |
| LCN15/Lipocalin-15 | 6 | −2.5 | −3.7 | −2.9 | 2 | −3.2, −3.3 (1.1e−3, 1.1e−3) |
| TBA1B/Tubulin alpha-1B chain | 3 | 2.8 | 2.6 | 2.2 | 2 | 1.8, 1.9 (1.0e−3, 8.6e−4) |
| CYTA/Cystatin-A | 5 | −2.6 | −2.8 | −2.4 | 2 | −3.5, −2.8 (8.6e−4, 6.7e−4) |

TABLE 2-continued

Expression ratios for 26 candidate biomarker proteins in pooled discovery and targeted MRM assays

| UniProt Gene Symbol/<br>Protein Name | Unbiased Pool Peptides | UNBIASED (POOL) H3N2 #1 [3]Criterion | | | Targeted MRM Peptides | TARGETED MRM (INDIVIDUAL) H3N2 #1/2 and HRV #1/2 [4]Fold change $[T/BL]_{Inf}$ (FDR) |
|---|---|---|---|---|---|---|
| | | 1 | 2 | 3 | | |
| APOA1/Apolipoprotein A-I | 57 | 5.1 | −1.3 | −1.8 | 2 | 2.1 (1.2e−3) |
| ANGT/Angiotensinogen | 6 | 4.9 | 2.3 | 1.5 | 2 | 1.4, 1.7 (0.018, 8.4e−3) |
| SPR1A/Cornifin-A | 2 | −2.7 | −2.0 | −1.2 | 2 | −2.2, −1.8 (9.0e−3, 3.9e−3) |
| CASPE/Caspase-14 | 10 | −3.8 | −2.1 | −2.2 | 2 | −3.1, −2.7 (6.7e−4, 1.0e−3) |
| APOA4/Apolipoprotein A-IV | 7 | 11.4 | 1.1 | 1.0 | 2 | 2.2, 2.0 (1.3e−3, 1.4e−3) |
| AMY1/Alpha-amylase 1 | 7 | −2.4 | −2.9 | −1.7 | 2 | −2.1 (2.9e−3) |
| VMO1/Vitelline membrane outer layer prot 1 | 3 | −2.0 | −2.9 | −1.4 | 2 | −2.2, −2.6 (0.016, 8.7e−3) |
| ANXA2/Annexin A2 | 8 | −2.0 | −2.0 | −1.6 | 2 | −1.5, −1.6 (5.7e−3, 4.7e−3) |
| CAYP1/Calcyphosin | 4 | 7.5 | 2.5 | 2.1 | 3 | 2.6, 2.7, 2.4 (2.9e−3, 1.6e−3, 2.4e−3) |
| GGCT/Gamma-glutamylcyclotransferase | 2 | −4.6 | −2.0 | −1.7 | 2 | −1.7, −2.1 (0.029, 9.9e−4) |
| DCD/Dermcidin | 3 | −7.4 | −2.5 | −4.3 | 2 | −2.3, −2.2 (6.4e−3, 6.4e−3) |
| SPRR3/Small proline-rich protein 3 | 2 | 2.4 | 2.1 | 1.2 | 2 | −1.6, −1.9 (0.023, 7.8e−3) |
| APOA2/Apolipoprotein A-I | 9 | 8.7 | 1.3 | 1.3 | 2 | 1.7, 1.5 (0.016, 0.07) |
| STAT/Statherin | 2 | 112.6 | 17.5 | 140.0 | 1 | 5.4 (1.0e−3) |
| PROL4/Proline-rich protein 4 | 66 | −2.6 | −2.0 | −2.3 | 2 | −1.1 (0.802) |
| GSTA2/Glutathione S-transferase A2 | 3 | 9.1 | 4.2 | 1.6 | 2 | 1.0 (0.902) |
| FILA/Filaggrin | 2 | −7.3 | −3.8 | −3.9 | 1 | −1.6 (0.061) |

[1] Included due to potential biological significance;
[2] Included as potential endogenous control;
[3] Fold change in pooled analysis for each of 3 prioritization criteria;
[4] Average fold change per peptide across all cohorts (p-values adjusted for false discovery rate)

Table 2. Candidate biomarker protein relative expression ratios. Rows represents the 26 host NPL proteins for which MRM assays were developed. UniProt gene symbol and protein names are shown for each candidate protein, with number of peptides measured for both unbiased pool and targeted MRM analyses. Unbiased pool ratios are shown for selection criteria 1, 2, and 3, as described in Supplementary Table S3. Fold expression changes from BL to T for infected individuals, as measured by peptide-specific MRM assay, across all four ARV challenge studies are shown with two-sided t-test Benjamini-Hochberg FDR-adjusted p-values (in parentheses) for each peptide, respectively.

TABLE 2A 26 proteins included ARV signature

| UniProt Protein ID | Protein name | Notes |
|---|---|---|
| P00330 | ADH1_YEAST | exogenous control |
| P02763 | A1AG1_HUMAN | |
| P01009 | A1AT_HUMAN | |
| P04745 | AMY1_HUMAN | |
| P01019 | ANGT_HUMAN | |
| P07355 | ANXA2_HUMAN | |
| P02647 | APOA1_HUMAN | |
| P02652 | APOA2_HUMAN | |
| P06727 | APOA4_HUMAN | |
| Q13938 | CAYP1_HUMAN | |
| P31944 | CASPE_HUMAN | |
| P00751 | CFAB_HUMAN | |
| P35321 | SPR1A_HUMAN | |
| P01040 | CYTA_HUMAN | |
| P81605 | DCD_HUMAN | |
| P20930 | FILA_HUMAN | |
| O75223 | GGCT_HUMAN | |
| P09210 | GSTA2_HUMAN | |
| Q6UWW0 | LCN15_HUMAN | |
| P05155 | IC1_HUMAN | |
| Q16378 | PROL4_HUMAN | |
| P49788 | TIG1_HUMAN | |
| Q9UBC9 | SPRR3_HUMAN | |
| P02808 | STAT_HUMAN | |
| P68363 | TBA1B_HUMAN | |

TABLE 2A-continued 26 proteins included ARV signature

| UniProt Protein ID | Protein name | Notes |
|---|---|---|
| Q7Z5L0 | VMO1_HUMAN | |
| P02768 | ALBU_HUMAN | |

3.5 Independent Verification in Additional Viral Challenge Cohorts

Figure 3:
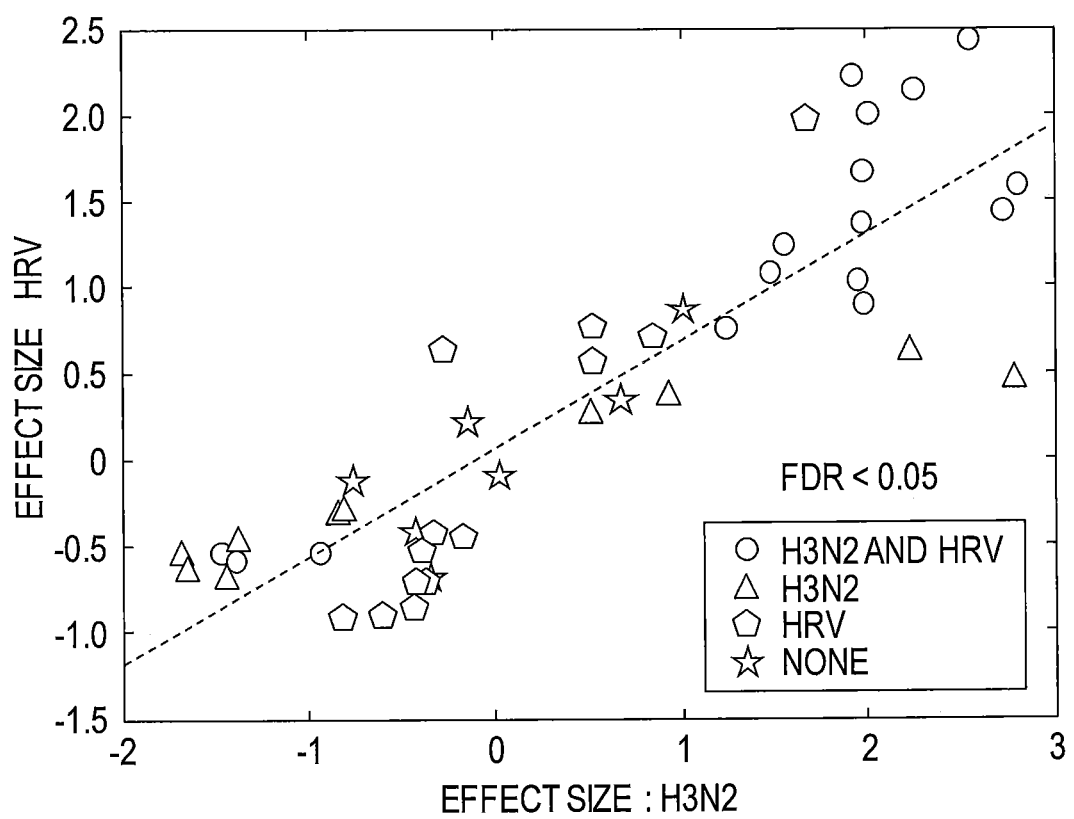
FIG. 3 is a graph showing the correlation of the peptide expression changes for all four H3N2 and HRV cohorts (r=0.871) in accordance with one embodiment of the present disclosure. Graph shows peptides with significant expression changes (Benjamini-Hochberg FDR<0.05) in response to H3N2 infection (10 peptides), HRV infection (14 peptides), both H3N2 and HRV infection (16 peptides), or neither cohort as measured by MRM.

We then sought to independently verify candidate peptide expression changes in individual participant samples from a second H3N2 challenge cohort, as well as two additional challenge studies using a second common ARV, human rhinovirus. Individual participant NPL samples from the 3 additional cohorts were processed and measured using the same panel of experimental and control peptide MRM assays derived from the H3N2 #1 cohort. In a combined analysis across the four independent ARV cohorts, we found that median sample-wise peptide expression intensity was relatively constant across all samples regardless of infection status, though 26 of 47 peptide analytes measured to be differentially expressed (Benjamini-Hochberg FDR<0.05) at the time of maximal symptoms in the infected H3N2 subjects. Likewise, 30 peptide analytes were differentially expressed (Benjamini-Hochberg FDR<0.05) in the HRV subjects at time T, with 16 peptides overlapping between the two H3N2 and two HRV cohorts. The direction and magnitude of change for all 40 peptide analytes (10 H3N2 only, 14 HRV only, 16 in both) that were significantly differentially expressed in either the H3N2 or HRV cohorts are highly correlated (r=0.871) between viral groups (FIG. 3), indicating that these analytes are likely not virus type-specific or useful in differentiating between H3N2 and HRV. This finding provided a basis for investigating the utility of these protein assays in a multi-analyte classification model of ARV infection.

3.6 Classification Model of ARV Infection

Figure 4A:
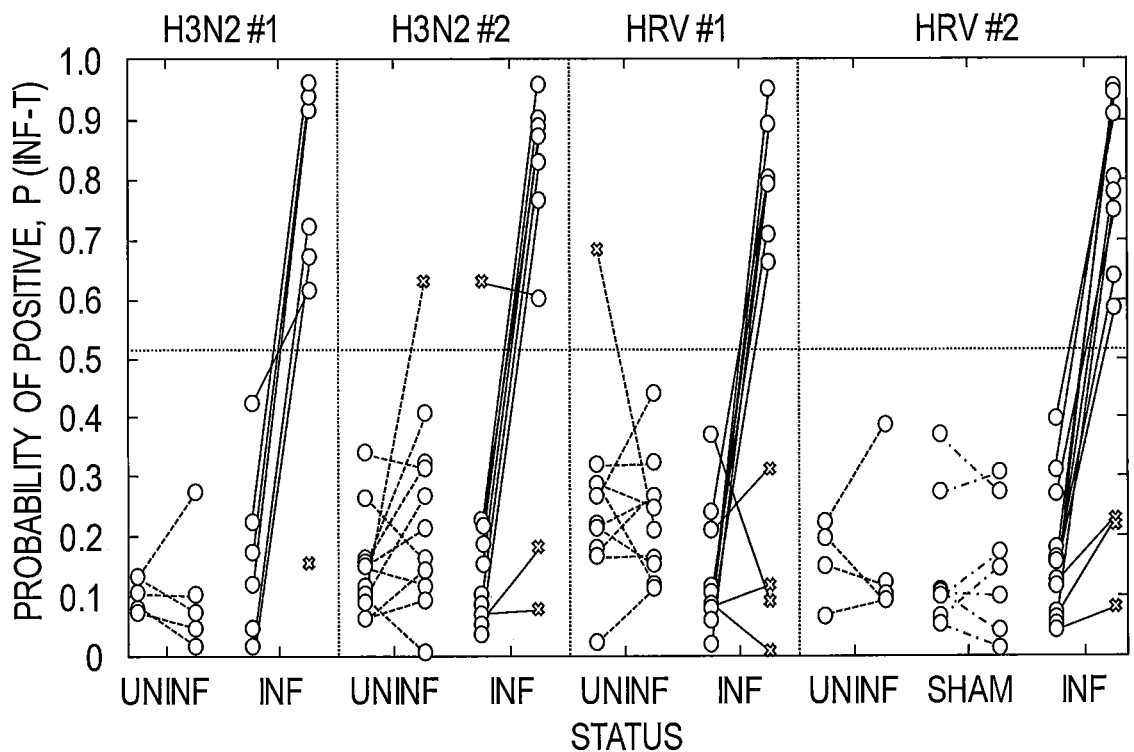
FIG. 4A-FIG. 4B are graphs showing the performance of NPL peptide classification model in independent ARV cohorts in accordance with one embodiment of the present disclosure. The model was fit to discriminate Inf-T from Inf-BL and Uninf-T.

To build an NPL protein classifier that distinguishes infected from uninfected subjects we utilized LASSO sparse logistic regression (Friedman et al., 2010) to build a list of potential logistic regression models. The classifier was trained to discriminate samples from infected individuals at time T (Inf-T) from paired baseline measures (Inf-BL) and from uninfected individuals at time T (Uninf-T). FIG. 4A shows the performance of a NPL classification model that selected 10 peptides (9 unique proteins), in the four independent challenge cohorts, including discordant individuals adjudicated using GEA status as a tiebreaker. For this analysis we ignored the paired nature of samples in the training and classification tasks in order to better estimate the accuracies in a situation in which baseline samples are not available. Overall classifier performance (FIG. 4B) in LOOCV yielded an AUROC of 0.8623 (95% CI: 0.7538-0.9315, bootstrapped 10K samples) with a 75% TPR and 97.46% TNR. Baseline samples from the asymptomatic cohort were withheld from model training since this was not a phenotype the model was trying to identify. However, they represent a cohort of asymptomatic individuals available for validation. Applying the model to these 37 samples revealed only one misclassification error (2.7%). LOOCV confusion matrix and identities of the 10 peptide classifier with weights are shown in Tables 3A and 3B, respectively. We also performed analyses separately on infection status of individuals independently of the GEA status (i.e., including only symptomatic shedders and asymptomatic shedders) with no surprisingly increased classification performance, 0.8821 LOOCV-AUC (vs. 0.8623), and on all individuals using shedding as outcome (ignoring symptoms) with 0.8610 LOOCV-AUC.

TABLE 3A 10-peptide classification model performance on ARV challenge cohorts

| Actual\Predicted | Others[1] | Inf at T |
|---|---|---|
| Others[1] | 77 | 2 |
| Inf at T | 10 | 30 |

[1]Inf-BL and Uninf-T;
Confusion matrix based on LOOCV using 10 peptide (9 protein) classification model

TABLE 3B

Identity and contribution of peptides in classification model

| Weight[1] | Gene Symbol | Peptide Sequence |
|---|---|---|
| 0.927 | A1AG1 | EQLGEFYEALDCLR (SEQ ID NO: 6) |
| 0.850 | TIG1 | VLAEVQEGR (SEQ ID NO: 46) |
| -0.266 | ANXA2 | TNQELQEINR (SEQ ID NO: 15) |
| -0.260 | LCN15 | VPALGYLDVR (SEQ ID NO: 40) |
| 0.249 | ANGT | ADSQAQLLLSTVVGVFTAPGLHLK (SEQ ID NO: 13) |

TABLE 3B-continued

Identity and contribution of peptides in classification model

| Weight[1] | Gene Symbol | Peptide Sequence |
|---|---|---|
| 0.228 | CFAB | EAGIPEFYDYDVALIK (SEQ ID NO: 28) |
| 0.198 | TBA1B | IHFPLATYAPVISAEK (SEQ ID NO: 52) |
| 0.154 | CAYP1 | EAVIAAAFAK (SEQ ID NO: 24) |
| 0.126 | STAT | FGYGYGPYQPVPEQPLYPQPYQPQ YQQYTF (SEQ ID NO: 50) |
| 0.081 | CFAB | YGLVTYATYPK (SEQ ID NO: 27) |

[1]Peptide weight contribution to classification model (negative value indicates down-regulated upon infection)

Table 3. 10-peptide classification model performance. (A) Classifier performance on individual samples from all four ARV cohorts as represented by LOOCV confusion matrix, with (B) identity and contribution (weight) for 10 peptides, with amino acid sequence in one-letter notation. Average peptide length is 11.8 amino acids, with range between 8 and 30 residues. Negative weight values indicate down-regulation upon infection.

3.7 Symptomatic but Uninfected Sham Controls

The experimental design of the HRV #2 challenge included a "sham" inoculation control group (FIG. 4A, panel HRV #2 in green), with several participants receiving intranasal inoculation of saline without HRV. Four of the seven sham controls reported symptoms sufficient to be classified as symptomatic, despite receiving no HRV inoculum and showing no microbiological evidence of infection. Interestingly, all four subjects were classified as negative by NPL MRM analysis, consistent with absence of HRV shedding and no observed GEA host response (Hero et al.) in the blood mRNA ARV infection pathway (Huang et al., 2011; McClain et al., 2016; Woods et al., 2013) for these subjects.

3.8 Pathway Analysis

Figure 4B:
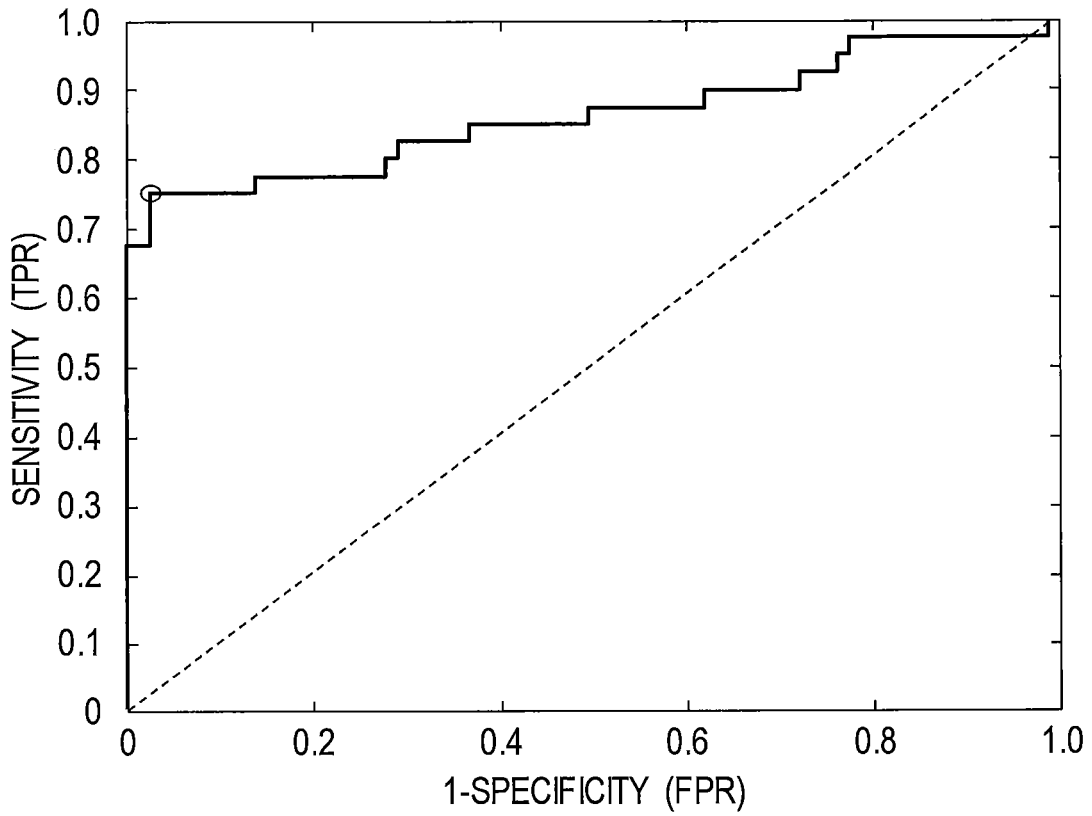

Since the classifier tested in FIG. 4A-FIG. 4B includes only 9 unique proteins, we repeated the analysis using a more relaxed variable selection parameter to better describe the biological pathways involved (LASSO regularization parameter, $\alpha=0.1$ rather than 1.0). The new classifier has nearly identical performance (0.8765 AUROC, 75% TPR, and 97.46 TNR) but selected 30 of 47 peptides (17 unique proteins). Pathway association analysis was performed using DAVID 6.7 Functional Annotation Tool (Huang da et al., 2009) using the 17 proteins selected by this expanded classifier as being informative in differentiating infected from uninfected individuals (results in Supplementary Table S5). Significant annotation clusters were primarily driven by 5 proteins (A1AG1, CFAB, A1AT, IC1, and APOA4), and were associated with Gene Ontology (GO) biological process terms acute inflammatory response (GO:0002526; p=1.6e−4), innate immune response (GO:0045087; p=9.9e−3), inflammatory response (GO:0006954; p=5.0e−3), and defense response (GO:0006952; p=3.9e−3). Similar results were seen when expanding the query to include all 26 protein candidates used in the phase 2 MRM analyses.

4. Discussion

We conducted unbiased and targeted protein analyses on human NPL samples collected from four independent ARV challenge cohorts (two influenza A H3N2, two HRV) to define host protein expression patterns characteristic of response to viral respiratory infection. The results demonstrate that robust changes in secreted proteins occur in the NPL of infected individuals, and that a subset of proteins is capable of accurately classifying the infected state of the individual.

Despite changes to the assay approach and methods in transitioning from pooled phase 1 discovery with unbiased 2D-LC-MS/MS proteomics to individual measurements in phase 2 discovery with MRM, we observed good reproduction of both the direction and magnitude of peptide expression measurements between the methods. This provides confidence in the specificity and quantitative performance of both methods. Importantly, this approach enabled accurate selection of candidate biomarkers in a pooled phase 1 discovery where sample amounts were severely limited on individual samples, and precluded the ability to analyze all samples using unbiased 2D-LC-MS/MS. Though some biomarker candidate attrition was expected because the biological variance is not available from the pooled data, with appropriate strategic filtering of the candidates we were able to have a high success rate for statistical validation between phase 1 (pooled discovery) and phase 2 (individual MRM measurements).

Investigations by our group and others have shown differential expression of host genes at the RNA level in peripheral blood in response to ARV infections (Ramilo et al., 2007; Woods et al., 2013; Aimee K. Zaas et al., 2013; A. K. Zaas et al., 2009), with heavy representation of genes in the IFN-signaling canonical pathway and innate immune response signaling. Analysis of differentially expressed NPL proteins in infected individuals demonstrates involvement in several biological pathways critical to mounting a host defense to virus infection, including innate immune responses, acute inflammatory responses, and defense response pathways. The inclusion of three members of the complement system (CFAB, A1AT, and IC1) is particularly consistent with an innate immune response, as the complement system enhances the ability of antibodies and phagocytic cells to clear pathogens from the infected site (Ricklin, Hajishengallis, Yang, & Lambris, 2010). Despite the apparently related pathways involved, there does not appear to be extensive overlap between the differentially expressed nasal proteins identified in our H3N2 #1 challenge study, and the previous peripheral blood RNA signatures of ARV infection characterized in the same challenge cohort (A. K. Zaas et al., 2009). One gene product that is increased at both the NPL peptide and peripheral blood RNA level upon influenza infection (C. M. Cameron et al., 2008; M. J. Cameron et al., 2007; A. K. Zaas et al., 2009) is IC1 (SERPING1 gene). IC1 (also called C1-inhibitor) is a peptidase inhibitor belonging to the serpin superfamily and has an important role in innate immunity through modulation of the classical pathway of complement activation (Gaboriaud et al., 2004). As the complement system has the potential to be damaging to host tissues, complement control proteins must tightly regulate activation. IC1 binds to complement protein C1 to inhibit activation of the classical complement pathway, and thus its discovery fits well with our understanding of the biology of these diseases.

Notably absent from this NPL protein analysis are proinflammatory cytokine and chemokine gene products which have previously been shown to be strong contributors to the host response both in peripheral blood and near the site of ARV infection (Kimura, Yoshizumi, Ishii, Oishi, & Ryo, 2015). Oshansky and colleagues assayed nasal lavage samples from a cohort of healthy and naturally-infected influenza patients using a multiplex cytokine/chemokine assay panel, reporting correlation of inflammatory cytokines MCP-3 and IFN-$\alpha$2 with disease progression (Oshansky et al., 2014). An aptamer-based detection method was subsequently used to screen the same cohort and generate quantitative measures of over 1000 protein analytes from nasal lavage, showing differential expression of 162 proteins including cytokines associated with immune response to infection (Marion et al., 2016). We did not identify inflammatory cytokines to be differentially expressed in our pooled NPL analysis. It is possible that cytokine proteins in NPL samples are expressed at levels below the detection limits of LC/MS-based methods, and that coupling targeted methods capable of detecting and quantifying cytokines directly may provide enhanced datasets for biomarker discovery.

The inclusion of "sham" infected participants in the HRV #2 cohort provided an important opportunity to assess the accuracy of standard clinical symptom assessments in the diagnosis of ARV infection. The clinical definition of symptomatic, even when applying standardized symptom scoring and algorithms, includes elements of subjectivity and thus may be imperfect in describing such infections. The finding that, despite the apparent presence of symptoms of infection, MRM analysis classified all seven individuals as uninfected suggests that this NPL biomarker assay has a lower false positive rate in diagnosing HRV infection than standard symptom status measures.

Experimental challenge studies provide an excellent model for studying ARV infection and illness, with pre-screened volunteers, known time of exposure, standardized pathogen exposure, and extensive sampling and data collection through the course of illness. However, experimental challenges do not perfectly replicate natural ARV infection and illness in humans. Volunteers in these studies are young and healthy, and represent a relatively homogenous population. In contrast, patients presenting to clinical care are demographically heterogeneous, have a variety of comorbidities, present at various times in the course of their illness, and contain a far greater breadth of potential pathogens beyond the two studied here. As such, additional validation should be performed in a more diverse population, such as patients presenting to clinical care with community-onset disease. While the generalizability of this study's findings will require additional validation, the high TNR of 97.46% suggests this assay may provide value in ruling out ARV infection.

Categorizing infection based upon host response represents an emerging strategy with great potential for complementing current pathogen-based diagnostics, as well as providing additional insights into the pathobiology of infection. The results presented in this study provide evidence that a protein-based host response to ARV infection can be detected in the nasopharyngeal space, and that this response involves perturbation of pathways involved in acute inflammation and innate immune response. Further, this work demonstrates that targeted assays measuring peptides involved in this response allow classification of ARV infection with a high degree of accuracy. Validation of these findings across independent experimentally infected Influenza A and human rhinovirus cohorts suggests a robust and generalized response to viral infection. With further development as a clinical diagnostic, this signature may have utility in rapid screening for emerging infections, avoidance of inappropriate antimicrobial therapy, and more rapid implementation of appropriate therapeutic and public health strategies. Nonetheless, as with other validated biomarkers, additional validation in community-based cohorts may further demonstrate the potential utility of such an assay in its clinical applications. Furthermore, testing this approach across a larger series of upper respiratory viruses may aid in understanding its full potential utility and limitations. An assay that combines host protein biomarkers with nasal viral antigen detection may be quite valuable in clinical care to optimize therapeutic decision making. And whilst a positive result from such an assay may avoid the use of inappropriate microbial therapy, it will likely require vigilance on the part of the clinician to exclude bacterial co-infection when clinically indicated.

Our previous demonstration of the potential for host response-based pre-symptomatic detection of H3N2 infection using blood RNA expression (McClain et al., 2016) raises the intriguing possibility that an NPL protein host response assay might be useful in early detection of ARV infection, and should be evaluated. The availability of a proteomic 'signature' that accurately classifies ARV infection and might be migrated to simple and inexpensive antibody-based tests that are routinely used in both clinical laboratory and over-the-counter diagnostic applications represents an important advance, and may one day yield a ARV host response test that is safe, simple, rapid, inexpensive, and accurate.

REFERENCES

Addona, T. A., Abbatiello, S. E., Schilling, B., Skates, S. J., Mani, D. R., Bunk, D. M., . . . Carr, S. A. (2009). Multi-site assessment of the precision and reproducibility of multiple reaction monitoring-based measurements of proteins in plasma. *Nat Biotechnol,* 27(7), 633-641. doi:10.1038/nbt.1546

Aebersold, R., Burlingame, A. L., & Bradshaw, R. A. (2013). Western blots versus selected reaction monitoring assays: time to turn the tables? *Mol Cell Proteomics,* 12(9), 2381-2382. doi:10.1074/mcp.E113.031658

Bhoj, V. G., Sun, Q., Bhoj, E. J., Somers, C., Chen, X., Tones, J. P., . . . Chen, Z. J. (2008). MAVS and MyD88 are essential for innate immunity but not cytotoxic T lymphocyte response against respiratory syncytial virus. *Proc Natl Acad Sci U S A,* 105(37), 14046-14051. doi:10.1073/pnas.0804717105

Boja, E. S., & Rodriguez, H. (2011). The path to clinical proteomics research: integration of proteomics, genomics, clinical laboratory and regulatory science. *Korean J Lab Med,* 31(2), 61-71. doi:10.3343/kjlm.2011.31.2.61

Byington, C. L., Ampofo, K., Stockmann, C., Adler, F. R., Herbener, A., Miller, T., . . . Pavia, A. T. (2015). Community Surveillance of Respiratory Viruses Among Families in the Utah Better Identification of Germs-Longitudinal Viral Epidemiology (BIG-LoVE) Study. *Clin Infect Dis,* 61(8), 1217-1224. doi:10.1093/cid/civ486

Cameron, C. M., Cameron, M. J., Bermejo-Martin, J. F., Ran, L., Xu, L., Turner, P. V., . . . Kelvin, D. J. (2008). Gene expression analysis of host innate immune responses during Lethal H5N1 infection in ferrets. *J Virol,* 82(22), 11308-11317. doi:10.1128/jvi.00691-08

Cameron, M. J., Ran, L., Xu, L., Danesh, A., Bermejo-Martin, J. F., Cameron, C. M., . . . Kelvin, D. J. (2007). Interferon-mediated immunopathological events are associated with atypical innate and adaptive immune responses in patients with severe acute respiratory syndrome. *J Virol,* 81(16), 8692-8706. doi:10.1128/jvi.00527-07

Fawcett, T. (2006). An introduction to ROC analysis. *Pattern recognition letters,* 27(8), 861-874.

Friedman, J., Hastie, T., & Tibshirani, R. (2010). Regularization Paths for Generalized Linear Models via Coordinate Descent. *J Stat Softw,* 33(1), 1-22.

Gaboriaud, C., Thielens, N. M., Gregory, L. A., Rossi, V., Fontecilla-Camps, J. C., & Arlaud, G. J. (2004). Structure and activation of the C1 complex of complement: unraveling the puzzle. *Trends Immunol,* 25(7), 368-373. doi:10.1016/j.it.2004.04.008

Gerszten, R. E., Can, S. A., & Sabatine, M. (2010). Integration of proteomic-based tools for improved biomarkers of myocardial injury. *Clin Chem,* 56(2), 194-201. doi:10.1373/clinchem.2009.127878

Hero, A. O., Arzouni, N., McClain, M. T., & Burke, T. W. Individualized gene enrichment analysis of activation of acute respiratory infection signature over time. *manuscript in preparation.*

Hersh, A. L., Shapiro, D. J., Pavia, A. T., & Shah, S. S. (2011). Antibiotic Prescribing in Ambulatory Pediatrics in the United States. *Pediatrics,* 128(6), 1053-1061. doi:10.1542/peds.2011-1337

Hong, C. Y., Lin, R. T., Tan, E. S., Chong, P. N., Tan, Y. S., Lew, Y. J., & Loo, L. H. (2004). Acute respiratory symptoms in adults in general practice. *Fam Pract,* 21(3), 317-323.

House, W. (2014). *National strategy for combating antibiotic-resistant bacteria.* 2014 September Huang da, W., Sherman, B. T., & Lempicki, R. A. (2009). Bioinformatics enrichment tools: paths toward the comprehensive functional analysis of large gene lists. *Nucleic Acids Res,* 37(1), 1-13. doi:10.1093/nar/gkn923

Huang, Y., Zaas, A. K., Rao, A., Dobigeon, N., Woolf, P. J., Veldman, T., . . . Hero, A. O., 3rd. (2011). Temporal dynamics of host molecular responses differentiate symptomatic and asymptomatic influenza a infection. *PLoS Genet,* 7(8), e1002234. doi:10.1371/journal.pgen.1002234

Jackson, G. G., Dowling, H. F., Spiesman, I. G., & Boand, A. V. (1958). Transmission of the common cold to volunteers under controlled conditions. I. The common cold as a clinical entity. *AMA Arch Intern Med,* 101(2), 267-278.

Johnston, S. L., Sanderson, G., Pattemore, P. K., Smith, S., Bardin, P. G., Bruce, C. B., . . . Holgate, S. T. (1993). Use of polymerase chain reaction for diagnosis of picornavirus infection in subjects with and without respiratory symptoms. *J Clin Microbiol,* 31(1), 111-117.

Johnstone, J., Majumdar, S. R., Fox, J. D., & Marrie, T. J. (2008). Viral infection in adults hospitalized with community-acquired pneumonia: prevalence, pathogens, and presentation. *Chest,* 134(6), 1141-1148. doi: 10.1378/chest.08-0888

Kimura, H., Yoshizumi, M., Ishii, H., Oishi, K., & Ryo, A. (2015). Cytokine production and signaling pathways in respiratory virus infection. *Pathophysiology and epidemiology of virus-induced asthma,* 4(276), 29.

Kiyonami, R., Schoen, A., Prakash, A., Peterman, S., Zabrouskov, V., Picotti, P., . . . Domon, B. (2011). Increased selectivity, analytical precision, and throughput in targeted proteomics. *Mol Cell Proteomics,* 10(2), M110 002931. doi:10.1074/mcp.M110.002931

Koyama, S., Ishii, K. J., Coban, C., & Akira, S. (2008). Innate immune response to viral infection. *Cytokine,* 43(3), 336-341. doi:10.1016/j.cyto.2008.07.009

Liu, T.-Y., Burke, T., Park, L. P., Woods, C. W., Zaas, A. K., Ginsburg, G. S., & Hero, A. O. (2016). An individualized predictor of health and disease using paired reference and target samples. *BMC Bioinformatics,* 17(1), 1-15. doi:10.1186/s12859-016-0889-9

Marion, T., Elbahesh, H., Thomas, P. G., DeVincenzo, J. P., Webby, R., & Schughart, K. (2016). Respiratory Mucosal Proteome Quantification in Human Influenza Infections. *PLoS One,* 11(4), e0153674. doi:10.1371/journal.pone.0153674

McCaig, L. F., & Hughes, J. M. (1995). Trends in antimicrobial drug prescribing among office-based physicians in the United States. *Jama,* 273(3), 214-219.

McClain, M. T., Nicholson, B. P., Park, L. P., Liu, T.-Y., Hero, A. O., Tsalik, E. L., . . . Woods, C. W. (2016). A Genomic Signature of Influenza Infection Shows Potential for Presymptomatic Detection, Guiding Early Therapy, and Monitoring Clinical Responses. *Open Forum Infectious Diseases,* 3(1). doi:10.1093/ofid/ofw007

O'Neill, J. (2015). *Rapid Diagnostics: Stopping Unnecessary Use of Antibiotics.*

Organization, W. H. (2015). Global Action Plan on Antimicrobial Resistance.

Oshansky, C. M., Gartland, A. J., Wong, S. S., Jeevan, T., Wang, D., Roddam, P. L., . . . Thomas, P. G. (2014). Mucosal immune responses predict clinical outcomes during influenza infection independently of age and viral load. *Am J Respir Crit Care Med,* 189(4), 449-462. doi:10.1164/rccm.201309-1616OC Pirillo, A., Catapano, A. L., & Norata, G. D. (2015). HDL in infectious diseases and sepsis. *Handb Exp Pharmacol,* 224, 483-508. doi:10.1007/978-3-319-09665-0_15

Ramilo, O., Allman, W., Chung, W., Mejias, A., Ardura, M., Glaser, C., . . . Chaussabel, D. (2007). Gene expression patterns in blood leukocytes discriminate patients with acute infections. *Blood,* 109(5), 2066-2077. doi:10.1182/blood-2006-02-002477

Ramilo, O., & Mejias, A. (2009). Shifting the paradigm: host gene signatures for diagnosis of infectious diseases. *Cell Host Microbe,* 6(3), 199-200. doi:10.1016/j.chom.2009.08.007

Ricklin, D., Hajishengallis, G., Yang, K., & Lambris, J. D. (2010). Complement: a key system for immune surveillance and homeostasis. *Nat Immunol,* 11(9), 785-797.

Thompson, M., Shay, D., Zhou, H., Bridges, C., Cheng, P., Burns, E., . . . Cox, N. (2010). Estimates of deaths associated with seasonal influenza-United States, 1976-2007. *Morbidity and Mortality Weekly Report,* 59(33), 1057-1062.

Tsalik, E. L., Henao, R., Nichols, M., Burke, T., Ko, E. R., McClain, M. T., . . . Woods, C. W. (2016). Host gene expression classifiers diagnose acute respiratory illness etiology. *Science Translational Medicine,* 8(322), 322ra311-322ra311. doi:10.1126/scitranslmed.aad6873

Woods, C. W., McClain, M. T., Chen, M., Zaas, A. K., Nicholson, B. P., Varkey, J., . . . Ginsburg, G. S. (2013). A host transcriptional signature for presymptomatic detection of infection in humans exposed to influenza H1N1 or H3N2. *PLoS One,* 8(1), e52198. doi:10.1371/journal.pone.0052198

Yoneyama, M., & Fujita, T. (2010). Recognition of viral nucleic acids in innate immunity. *Rev Med Virol,* 20(1), 4-22. doi:10.1002/rmv.633

Zaas, A. K., Burke, T., Chen, M., McClain, M., Nicholson, B., Veldman, T., . . . Ginsburg, G. S. (2013). A Host-Based RT-PCR Gene Expression Signature to Identify Acute Respiratory Viral Infection. *Science Translational Medicine,* 5(203), 203ra126-203ra126. doi:10.1126/scitranslmed.3006280

Zaas, A. K., Chen, M., Varkey, J., Veldman, T., Hero, A. O., 3rd, Lucas, J., . . . Ginsburg, G. S. (2009). Gene expression signatures diagnose influenza and other symptomatic respiratory viral infections in humans. *Cell Host Microbe,* 6(3), 207-217. doi:10.1016/j.chom.2009.07.006

Zaas, A. K., Garner, B. H., Tsalik, E. L., Burke, T., Woods, C. W., & Ginsburg, G. S. (2014).

The current epidemiology and clinical decisions surrounding acute respiratory infections. *Trends Mol Med,* 20(10), 579-588. doi:10.1016/j.molmed.2014.08.001

Example 2: Nasopharyngeal Protein Biomarkers of Acute Respiratory Virus Infection (Supplemental Materials)

Table S1. Additional ARV challenge cohort descriptions.
Table S2A. Symptomatic case definition algorithm
Table S2B. Viral shedding case definition algorithm.
Table S2C. Assignment of infected/uninfected status.
Table S3. Criteria for prioritization of candidate markers from pooled H3N2 NPL samples.
Table S4. 56 Peptides included in MRM assay development.
Table S5. 13 individuals misclassified using NPL classifier
Table S6. Pathway analysis using DAVID Functional Annotation Tool.

TABLE S1

| | Additional ARV challenge cohort description | | | |
|---|---|---|---|---|
| Challenge Study | H3N2 #1 | H3N2 #2 | HRV #1 | HRV #2 |
| Virus strain | A/Wisconsin/67/2005 | A/Wisconsin/67/2005 | HRV serotype 39 | HRV serotype 39 |
| Year | 2009 | 2011 | 2008 | 2010 |
| Location | Retroscreen | Retroscreen/hVivo | Univ of Virginia | Duke Univ |

TABLE S1-continued

Additional ARV challenge cohort description

| Challenge Study | H3N2 #1 | H3N2 #2 | HRV #1 | HRV #2 |
|---|---|---|---|---|
| IRB Protocol | Pro00006750 | Pro00029521 | Pro00003477 | Pro00022448 |
| #Subjects | 17 | 21 | 20 | 30 |
| #Subjects in this analysis (# infected) | 15 (9) | 21 (10) | 20 (10) | 24 (13) |
| Sub-group | | early tx group (n = 7) | | sham group (n = 8) |

Table S1. Additional ARV challenge cohort description. Cohort descriptions include specific influenza A and HRV strains used in the four challenge studies, as well as site, IRB protocol, total number of participants, number included in this analysis (with number phenotyped as infected). H3N2 #2 challenge included an early treatment subgroup, and HRV #2 included a sham inoculation subgroup.

TABLE S2A

Symptomatic case definition algorithm

1. Select maximal symptom score for each of 8 symptom categories for each day.
2. Sum maximal symptom score for each symptom category for each day across all 8 symptoms. Baseline adjustment: for subjects with non-zero baseline symptoms, subtract baseline score (per symptom category) from all other post-inoculation daily symptoms for that symptom category.
3. Sum the baseline-adjusted daily sums from (2) in 5-day running windows (post-inoculation).
4. Participant is "symptomatic" if any baseline-adjusted 5-day symptom sum is ≥6.
5. Symptom onset is the first day of a 2-day window with total score from (2) of ≥2 for both days.
6. Time T for symptomatic individuals is the first time point of maximal summed symptom scores.

Table S2A. Symptomatic case definition algorithm. Description of the modified Jackson symptom scoring algorithm used in defining challenge participants as symptomatic or asymptomatic based upon self-reported symptoms recorded at least twice daily, along with determination of times of symptom onset and maximal symptoms (time T).

TABLE S2B

Viral shedding case definition algorithm

1. Virus assay from nasal swab by quantitative culture at least daily ≥24 post-inoculation (expressed as TCID50/ml or pfu/ml).
2. Shedding positive if ≥2 measurable positive titer >1.25 results. For HRV, any ≥2 measurable titer (>0) is considered positive shedding. Need not be on same or consecutive days.
3. Shedding positive if ≥1 strong positive titer ≥3.0 result.

Table S2B. Viral shedding case definition algorithm. Description of the method used in defining challenge participants as shedding or non-shedding based on quantitative culture results. Values are expressed at TCID50/ml or pfu/ml.

TABLE S2C

| Assignment of infected or uninfected status | | | | | | |
|---|---|---|---|---|---|---|
| Symptomatic | + | − | + | + | − | − |
| Virus Shedding | + | − | − | − | + | + |
| GEA (RNA host response) | n/a | n/a | + | − | + | − |
| Infection | Inf | Uninf | Inf | Uninf | Inf | Uninf |

Table S2C. Assignment of Infected or Uninfected status. Individual challenge participants were deemed infected or uninfected based upon a combination of two or three criteria.

TABLE S3

Criteria for prioritization of candidate markers from pooled H3N2 NPI samples

Criterion 1: ≥2-fold change in expression among Infected subjects at time T relative to paired baseline (i.e., $[T/BL]_{inf} > \pm 2$-fold), with at least 2 peptides used for quantitation
Criterion 2: ≥2-fold change in expression among Infected subjects at time T relative to Uninfected subjects at time T (i.e., $[Inf/Uninf]_{time\ T} \geq \pm 2$-fold)
Criterion 3: For each protein, the ratio of the fold change (baseline to time T) for Infected versus Uninfected must be >1-fold (i.e., ratio of $[T/BL]_{Inf}$ vs $[T/BL]_{Uninf} > 1$-fold)

Uninf = uninfected individuals;
Inf = infected individuals;
BL = baseline;
T = time of maximal symptoms (time T).

Table S3. Criteria for prioritization of candidate markers from pooled H3N2 NPL samples. These three criteria were applied to 2D-LC-MS/MS data generated on four pools of NPL samples from H3N2 #1 challenge cohort. Expression ratios generated from these criteria are shown in Table 2.

TABLE S4

| Peptides included in MRM assay development | | | |
|---|---|---|---|
| Protein ID | name | Peptide Sequence | Notes |
| P00330\|ADH1_YEAST | Alcohol dehydrogenase 1 | ANELLINVK (SEQ ID NO: 1) | 1 |

TABLE S4-continued

Peptides included in MRM assay development

| Protein ID | name | Peptide Sequence | Notes |
|---|---|---|---|
| P00330\|ADH1_YEAST | Alcohol dehydrogenase 1 | IGDYAGIK (SEQ ID NO: 2) | 1 |
| P00330\|ADH1_YEAST | Alcohol dehydrogenase 1 | VLGIDGGEGK (SEQ ID NO: 3) | 1 |
| P00330\|ADH1_YEAST | Alcohol dehydrogenase 1 | EALDFFAR (SEQ ID NO: 4) | 1 |
| P00330\|ADH1_YEAST | Alcohol dehydrogenase 1 | VVGLSTLPEIYEK (SEQ ID NO: 5) | 1 |
| P02763\|A1AG1_HUMAN | Alpha-1-acid glycoprotein 1 | EQLGEFYEALDCLR (SEQ ID NO: 6) | 2 |
| P02763\|A1AG1_HUMAN | Alpha-1-acid glycoprotein 1 | SDVVYTDWK (SEQ ID NO: 7) | 3 |
| P01009\|A1AT_HUMAN | Alpha-1-antitrypsin | LSITGTYDLK (SEQ ID NO: 8) | 3 |
| P01009\|A1AT_HUMAN | Alpha-1-antitrypsin | SVLGQLGITK (SEQ ID NO: 9) | 3 |
| P04745\|AMY1_HUMAN | Alpha-amylase 1 | TSIVHLFEWR (SEQ ID NO: 10) | 4 |
| P04745\|AMY1_HUMAN | Alpha-amylase 1 | ALVFVDNHDNQR (SEQ ID NO: 11) |  |
| P01019\|ANGT_HUMAN | Angiotensinogen | ALQDQLVLVAAK (SEQ ID NO: 12) |  |
| P01019\|ANGT_HUMAN | Angiotensinogen | ADSQAQLLLSTVVGVFTAPGLHLK (SEQ ID NO: 13) | 2 |
| P07355\|ANXA2_HUMAN | Annexin A2 | GVDEVTIVNILTNR (SEQ ID NO: 14) | 3 |
| P07355\|ANXA2_HUMAN | Annexin A2 | TNQELQEINR (SEQ ID NO: 15) | 2 |
| P02647\|APOA1_HUMAN | Apolipoprotein A-I | LLDNWDSVTSTFSK (SEQ ID NO: 16) | 4 |
| P02647\|APOA1_HUMAN | Apolipoprotein A-I | ATEHLSTLSEK (SEQ ID NO: 17) |  |
| P02652\|APOA2_HUMAN | Apolipoprotein A-II | EPCVESLVSQYFQTVTDYGK (SEQ ID NO: 18) |  |
| P02652\|APOA2_HUMAN | Apolipoprotein A-II | SKEQLTPLIK (SEQ ID NO: 19) |  |
| P06727\|APOA4_HUMAN | Apolipoprotein A-IV | LTPYADEFK (SEQ ID NO: 20) |  |
| P06727\|APOA4_HUMAN | Apolipoprotein A-IV | LAPLAEDVR (SEQ ID NO: 21) | 3 |
| Q13938\|CAYP1_HUMAN | Calcyphosin | SLDADEFR (SEQ ID NO: 22) | 3 |
| Q13938\|CAYP1_HUMAN | Calcyphosin | LGLVLDQAEAEGVCR (SEQ ID NO: 23) | 3 |
| Q13938\|CAYP1_HUMAN | Calcyphosin | EAVIAAAFAK (SEQ ID NO: 24) | 2 |
| P31944\|CASPE_HUMAN | Caspase-14 | LALILCVTK (SEQ ID NO: 25) | 3 |
| P31944\|CASPE_HUMAN | Caspase-14 | VYIIQACR (SEQ ID NO: 26) | 3 |

TABLE S4-continued

Peptides included in MRM assay development

| Protein ID | name | Peptide Sequence | Notes |
|---|---|---|---|
| P00751\|CFAB_HUMAN | Complement factor B | YGLVTYATYPK (SEQ ID NO: 27) | 2 |
| P00751\|CFAB_HUMAN | Complement factor B | EAGIPEFYDYDVALIK (SEQ ID NO: 28) | 2 |
| P35321\|SPR1A_HUMAN | Cornifin-A | VPEPCQPK (SEQ ID NO: 29) | 3 |
| P35321\|SPR1A_HUMAN | Cornifin-A | VPEPCPSTVTPAPAQQK (SEQ ID NO: 30) | 3 |
| P01040\|CYTA_HUMAN | Cystatin-A | TQVVAGTNYYIK (SEQ ID NO: 31) | 3 |
| P01040\|CYTA_HUMAN | Cystatin-A | SLPGQNEDLVLTGYQVDK (SEQ ID NO: 32) | 3 |
| P81605\|DCD_HUMAN | Dermcidin | ENAGEDPGLAR (SEQ ID NO: 33) | |
| P81605\|DCD_HUMAN | Dermcidin | DAVEDLESVGK (SEQ ID NO: 34) | |
| P20930\|FILA_HUMAN | Filaggrin | HSGIGHGQASSAVR (SEQ ID NO: 35) | |
| O75223\|GGCT_HUMAN | Gamma-glutamylcyclotransferase | NPSAAFFCVAR (SEQ ID NO: 36) | |
| O75223\|GGCT_HUMAN | Gamma-glutamylcyclotransferase | VSEEIEDIIK (SEQ ID NO: 37) | 3 |
| P09210\|GSTA2_HUMAN | Glutathione S-transferase A2 | AILNYIASK (SEQ ID NO: 38) | |
| P09210\|GSTA2_HUMAN | Glutathione S-transferase A2 | ISNLPTVK (SEQ ID NO: 39) | 4 |
| Q6UWW0\|LCN15_HUMAN | Lipocalin-15 | VPALGYLDVR (SEQ ID NO: 40) | 2 |
| Q6UWW0\|LCN15_HUMAN | Lipocalin-15 | TQDVSPQALK (SEQ ID NO: 41) | 3 |
| P05155\|IC1_HUMAN | Plasma protease C1 inhibitor | DFTCVHQALK (SEQ ID NO: 42) | |
| P05155\|IC1_HUMAN | Plasma protease C1 inhibitor | LLDSLPSDTR (SEQ ID NO: 43) | 3 |
| Q16378\|PROL4_HUMAN | Proline-rich protein 4 | FPSVSLQEASSFFR (SEQ ID NO: 44) | |
| Q16378\|PROL4_HUMAN | Proline-rich protein 4 | HPQEQPLW (SEQ ID NO: 45) | 4 |
| P49788\|TIG1_HUMAN | Retinoic acid receptor responder protein 1 | VLAEVQEGR (SEQ ID NO: 46) | 2 |
| P49788\|TIG1_HUMAN | Retinoic acid receptor responder protein 1 | VHVVFSTER (SEQ ID NO: 47) | 3 |
| Q9UBC9\|SPRR3_HUMAN | Small proline-rich protein 3 | VPEPGYTK (SEQ ID NO: 48) | |
| Q9UBC9\|SPRR3_HUMAN | Small proline-rich protein 3 | VPEPGSIK (SEQ ID NO: 49) | |
| P02808\|STAT_HUMAN | Statherin | FGYGYGPYQPVPEQPLYPQPYQPQYQQYTF (SEQ ID NO: 50) | 2 |

TABLE S4-continued

Peptides included in MRM assay development

| Protein ID | name | Peptide Sequence | Notes |
|---|---|---|---|
| P68363\|TBA1B_HUMAN | Tubulin alpha-1B chain | AVFVDLEPTVIDEVR (SEQ ID NO: 51) | 3 |
| P68363\|TBA1B_HUMAN | Tubulin alpha-1B chain | IHFPLATYAPVISAEK (SEQ ID NO: 52) | 2 |
| Q7Z5L0\|VMO1_HUMAN | Vitelline membrane outer layer protein 1 homolog | VEAPTTLGDNTAANNVR (SEQ ID NO: 53) | |
| Q7Z5L0\|VMO1_HUMAN | Vitelline membrane outer layer protein 1 homolog | GLGDDTALNDAR (SEQ ID NO: 54) | |
| P02768\|ALBU_HUMAN | Serum albumin | LVNEVTEFAK (SEQ ID NO: 55) | 3 |
| P02768\|ALBU_HUMAN | Serum albumin | RPCFSALEVDETYVPK (SEQ ID NO: 56) | 3 |

1 exogenous yeast control peptides;
2 ten peptide signature included in ARV classifier;
3 expanded 30 peptide signature for pathway analysis (α = 0.1);
4 unsuccessful assays excluded due to multiple missing values Table S4. Peptides included in MRM assay development. Rows represent the 56 peptide MRM assays developed and tested in this study, including 5 exogenous (spiked) Yeast ADH peptides[1]. 10-peptides included in the NPL ARV classifier[2] and expanded 30-peptide classifier[3] are indicated in Notes column. Four peptides[4] failed to yield a successful MRM assay. Of the 56 peptides, 46 were unique for one specific isoform of a targeted protein (protein isoform information can be found in file "NasalMRMAssay_Targeted-Peptide_Redundancy.xlsx" at https://bitbucket.org/rhenao/npl_ebm).

TABLE S5

13 individuals misclassified using NPL classifier

| Cohort | Subj ID | Sx/Asx | Shed +/- | GEA +/- | Infected | NPL@ BL[1] | NPL@ T[1] | Notes |
|---|---|---|---|---|---|---|---|---|
| H3N2 #1 | 15 | Sx | + | + | Inf | n/a | -* | |
| H3N2 #2 | 1 | Sx | + | + | Inf | - | -* | early Tx |
| H3N2 #2 | 4 | Sx | + | + | Inf | - | -* | |
| H3N2 #2 | 8 | Sx | - | + | Inf | +* | + | |
| H3N2 #2 | 13 | Asx | - | - | Uninf | - | +* | early Tx |
| HRV #1 | 5 | Sx | + | - | Inf | - | -* | |
| HRV #1 | 6 | Sx | + | - | Inf | - | -* | |
| HRV #1 | 9 | Sx | + | - | Inf | - | -* | |
| HRV #1 | 10 | Sx | - | - | Uninf | +* | - | |
| HRV #1 | 11 | Sx | + | + | Inf | - | -* | |
| HRV #2 | 9 | Sx | + | + | Inf | - | -* | |
| HRV #2 | 15 | Asx | + | + | Inf | - | -* | |
| HRV #2 | 22 | Sx | + | + | Inf | - | -* | |

[1] incorrect NPL classification (relative to Inf/Uninf status) shown with asterisk (*)

Table S5. Individuals misclassified using NPL classifier. NPL protein-based classification did not match the infection status label for 13 individual samples at baseline (NPL@BL) or time T (NPL@T).

TABLE S6

Pathway analysis using DAVID Functional Annotation Tool

| GO term | Biological Process | Count | p-value | Benjamini-Hochberg |
|---|---|---|---|---|
| GO: 0002526 | Acute inflammatory response | 4 | 1.6e-4 | 7.9e-2 |
| GO: 0045087 | Innate immune response | 3 | 9.9e-3 | 5.8e-1 |
| GO: 0006954 | Inflammatory response | 4 | 5.0e-3 | 4.8e-1 |
| GO: 0006952 | Defense response | 5 | 3.9e-3 | 4.9e-1 |

Table S6. Pathway analysis using DAVID Functional Annotation Tool. Pathway association analysis was performed using expanded 17 protein classifier. Annotation clusters are shown with Gene Ontology (GO) biological process terms and names, along with number of proteins present in each process.

Supplementary Methods

Challenge Cohort Descriptions

Influenza H3N2. Influenza A H3N2 (A/Wisconsin/67/2005; H3N2 cohort #1) experimental challenge was conducted as described previously (Woods et al., 2013; Aimee K. Zaas et al., 2013; A. K. Zaas et al., 2009). Healthy volunteers (n=17; 15 included in this analysis) received bilateral intranasal inoculation with influenza A H3N2/Wisconsin/67/2005 (H3N2). NPL specimens were collected at 24hr intervals throughout duration of the 6 days in quarantine, aliquoted, and stored at −80C. All participants received oral oseltamivir (Roche Pharmaceuticals, 75 mg) twice daily as treatment or prophylaxis at beginning at day 6. In this cohort, two individuals were excluded from secondary analyses (no protein data were generated) as described previously (Woods et al., 2013). These two subjects were asymptomatic and shedding negative, but showed evidence of antibody seroconversion at day 28. Thus, it could not be determined whether or when influenza infection occurred. A second H3N2 (H3N2 cohort #2) experimental challenge study was subsequently conducted and described (McClain et al., 2016). Briefly, healthy volunteers (n=21; 21 included in this analysis) were inoculated with influenza A H3N2 (A/Wisconsin/67/2005) into bilateral nares. At predetermined intervals, biological samples including NPL (daily) were obtained from each participant, aliquoted, and stored at −80° C. All participants received oral oseltamivir (75 mg) twice daily either at 36 hours (early treatment arm) or at 5 days post-inoculation (standard treatment arm). All subjects were negative by rapid antigen testing (BinaxNow Rapid Influenza Antigen; Inverness Medical Innovations, Inc) at time of discharge.

Human Rhinovirus. Human Rhinovirus (serotype 39; HRV cohort #1) experimental challenge was described previously (A. K. Zaas et al., 2009). Briefly, healthy volunteers underwent prescreening, and participants meeting inclusion criteria (n=20; 20 included in this analysis) were inoculated intranasally and admitted to quarantine facility. Biological specimens, including NPL fluids, were collected at baseline and at predetermined intervals post-inoculation. A second, independent HRV (HRV cohort #2) experimental challenge study was subsequently conducted and described (Liu et al., 2016). As previously, healthy volunteers (n=30 total; 24 included in this analysis) were inoculated intranasally with HRV serotype 39 and biological specimens and clinical/symptom data were collected throughout the time-course. This challenge cohort also included a blinded, "sham" infected (saline only), control group (n=8; 7 included in this analysis). In this second cohort, six individuals were excluded from secondary analyses (no protein data were generated) for suspected baseline contamination (two), incomplete timecourse resulting in essential samples or data missing (three), or subject withdrawal from protocol 24 hr post-inoculation (one).

Participant Case Definitions

Case definitions. Self-reported symptoms were recorded at predetermined intervals prior to inoculation and at least twice daily throughout the time-course of infection and resolution using a modified Jackson score method as reported previously (Jackson, Dowling, Spiesman, & Boand, 1958; A. K. Zaas et al., 2009). This modified Jackson score requires subjects to self-report 8 symptoms of upper respiratory infection (headache, sore throat, rhinorrhea, rhinitis, sneezing, coughing, myalgia, malaise) on a standardized scale of 0 to 3 (no symptoms (0), just noticeable symptoms (1), bothersome but can still do activities (2), and bothersome and cannot do activities (3)). Participants were classified as "symptomatic" based on a modified Jackson score of ≥6 over a consecutive five-day period (Supplementary Table S2A). Standardized symptom scores were tabulated for each study to determine infection rate and time of maximal symptoms (time T), the first time point of maximal summed symptom scores. For asymptomatic individuals, a matched "time T" was defined as the average of time T for symptomatic individuals within the same cohort. Shedding status was determined based on viral quantitative culture as described previously (A. K. Zaas et al., 2009) and outlined in Supplementary Table S2B.

GEA "tiebreaker". In the case of individuals with discordant shedding and symptom labels (e.g. symptomatic but non-shedding), a third criterion based on the peripheral blood gene expression analysis (GEA) of host response to ARV infection was applied as a "tiebreaker" to establish infection status (A. O. Hero, in preparation). This GEA approach utilized a 26-gene signature (Huang et al., 2011; A. K. Zaas et al., 2009) to determine the presence or absence of the acute respiratory viral infection molecular signature. Assignment of infected (Inf) or uninfected (Uninf) status based on these criteria is summarized in Supplementary Table S2C. There are 21 (26%) discordant individuals (see Table 1 for breakdown), 12 symptomatic non-shedders and 9 asymptomatic shedders. From these, 4 (3 asymptomatic shedders) were labeled as infected and 17 (11 symptomatic non-shedders) as uninfected by the tiebreaker analysis. This means that in 2/3 of the individuals the tiebreakers analysis gave preference to shedding over symptoms. Only 1 symptomatic non-shedder was observed, and therefore the GEA tiebreaker led to an infected label with no shedding detected. To address the possibility that another respiratory virus might be responsible for the observed symptoms and GEA response, we performed PCR-based respiratory panel testing (Biofire Respiratory Panel) on NP swab sample (time T) from this participant. Results for this participant sample were negative for all 20 respiratory pathogens tested.

Sample Collection and Processing

NPL sample collection. The nasopharyngeal lavage procedure was performed as follows: deliver sterile 0.9% saline solution (5 ml into each nares) into nasopharyngeal space (while subject occludes soft palate and makes "humming" sound close to back of throat), using a sterile syringe attached to sterile rubber tubing. Expelled nasal wash is collected (typical yield 6-7 ml) into sterile collection cup, and immediately vortexed, aliquoted, and stored at −80C. NPL samples were collected at baseline (pre-inoculation), and at 24 hr intervals post inoculation.

NPL Pooling and Sample Processing. 500 uL of neat NPL from each participant was filtered through a 0.22 um cellulose acetate filters (Agilent) to remove particulates and then subjected to a buffer exchange into 50 mM ammonium bicarbonate (pH 8.0) and concentration using 10 kDa Amicon Ultra centrifugation cartridges (Millipore) according to manufacturer protocol. Micro Bradford assays (Pierce) were then performed to estimate total protein concentrations and all samples were normalized to 0.12 ug/uL in 50 mM ammonium bicarbonate, pH 8.0. Due to low total protein quantity, a four sample pools representing four groups (Asx BL, Asx T, Sx BL, and Sx T) were created. For each participant sample with at least 5 ug total NPL protein available, an equal NPL protein mass (2 ug total protein) was included in the appropriate pool. Normalized pooled samples (2D-LC-MS/MS) and individual participant samples (MRM) were supplemented with 0.2% Rapigest SF (Waters Corp) surfactant prior to being reduced with 10 mM dithiolthreitol for 20 min at 60° C. and alkylated with 20 mM iodoacetamide for 45 min at room temperature. Samples (pooled or individual) were proteolycially digested with trypsin (1:50 enzyme:total protein ratio) at 37° C. for 18 hr. Following digestion, Rapigest surfactant was hydrolyzed with 0.1% TFA (pH 2.5) at 60° C. for 2 hr and insoluble material was removed by centrifugation at 15,000 rpm for 10 min Samples were dried using vacuum centrifugation and resuspended at 0.6 ug/uL in either 200 mM ammonium formate, pH 10.0, or 2% MeCN/0.1% formic acid, pH 3, for pooled or individual samples, respectively. Prior to LC-MS analysis, all samples were spiked with ADH1_YEAST digest (Massprep standard, Waters Corporation) as an internal standard (50 fluol ADH per ug total NL protein).

Discovery LC/LC-MS/NIS

Discovery Proteomics: Open Platform Nano-scale Capillary UPLC-MS/MS

Quantitative 10-fraction two-dimensional liquid chromatography—tandem mass spectrometry (2D-LC-MS/MS) was performed on 3 µg of protein digest per sample pool in duplicate. The method uses LC/LC in a high-low pH reversed phase/reversed phase configuration on a nanoAcquity UPLC system (Waters Corp) coupled to a Synapt G2 HDMS high resolution accurate mass tandem MS (Waters Corp.) with nanoelectrospray ionization in a manner similar to previously described (Dowell, Frost, Zhang, & Li, 2008; Gilar, Olivova, Daly, & Gebler, 2005a, 2005b). Peptides were first trapped at 2 µl/min at 97/3 v/v water/MeCN in 20 mM ammonium formate (pH 10) on a 5 µm XBridge BEH130 C18 300 um×50 mm column (Waters). A series of step-elutions of MeCN at 2 µl/min was used to elute peptides from the $1^{st}$ dimension column. Ten steps of 7.4%, 10.8%, 12.6%, 14.0%, 15.3%, 16.7%, 18.3%, 20.4%, 23.5% and 65.0% MeCN were utilized for the unbiased analyses; these percentages were optimized for delivery of an approximately equal load to the $2^{nd}$ dimension column for each fraction. For $2^{nd}$ dimension separation, the eluent from the $1^{st}$ dimension was first diluted 10-fold online with 99.8/0.1/0.1 v/v/v water/MeCN/formic acid and trapped on a 5 µin Symmetry C18 180 µm×20 mm trapping column (Waters). The $2^{nd}$ dimension separations were performed on a 1.7 µm Acquity BEH130 C18 75 µm×150 mm column (Waters) using a linear gradient of 7% to 35% MeCN with 0.1% formic acid over 37 min, at a flow rate of 0.5 µl/min and column temperature of 35° C. Quantitative acquisitions were performed on the Synapt G2 MS operating in a data-independent acquisition (MSE) mode, using 0.6 second alternating cycle time between low (6V) and high (15-40V) collision energy (CE). Scans performed at low CE measure peptide accurate mass and intensity (abundance), while scans at elevated CE allow for qualitative identification of the resulting peptide fragments via database searching. Additional qualitative only acquisitions were performed on the Synapt G2 MS operating in a data-dependent acquisition (DDA) mode, with MS/MS spectra acquired for the top three precursor ions using charge-state dependent CID energy settings. A 120 sec dynamic exclusion limit was employed for all DDA acquisitions. The total analysis cycle time for each sample injection was approximately 12 hours.

Following duplicate quantitative analysis of each of the four pooled samples and four supplementary qualitative analyses of a pool of the pooled samples, all 12 MS/MS data files were imported into Rosetta Elucidator v3.3 (Rosetta Biosoftware, Inc) and were aligned based on the accurate mass and retention time of detected ions ("features") using PeakTeller algorithm (Elucidator). The relative peptide abundance was calculated based on area-under-the-curve (AUC) of aligned features across all runs. The overall dataset had 1,505,293 quantified features, and high collision energy (peptide fragment) data were collected in 589,177 spectra for sequencing by database searching. MS/MS data were searched against a SwissProt_Human (www.uniprot.org) database (20,265 forward entries) that also contained a reversed-sequence "decoy" database for false positive rate determination. Search tolerances were 10 ppm precursor and either 0.04 Da or 25 ppm product ions for DDA data and MSE data, respectively. After individual peptide scoring using PeptideProphet algorithm (Elucidator), the data was annotated at a <1% peptide false discovery rate (FDR). For quantitative processing, peptide quantities across all ten LC/LC fractions were summed and the dataset was intensity scaled to the robust mean (excluded highest and lowest 10% of detected features) across all quantitative acquisitions. The final quantitative dataset for NPL was based on 3285 peptides and contains 438 unique proteins.

Targeted MRM

Quantitation and Verification: MRM Assay Design and Peptide Measurements

MRM assays were performed on a Waters 1D NanoAcquity UPLC coupled through an electrospray ionization interface to a Waters Xevo TQ mass spectrometer operating in a positive-ion targeted MRM mode. Reversed-phase chromatographic separations were performed on a 1.7 um BEH C18 75 um×250 mm UPLC column operating at 300 nL/min with a linear gradient from 5% MeCN/0.1% formic acid to 40% MeCN/0.1% formic acid over 90 minutes. The Xevo TQ mass spectrometer was set to an auto-dwell determination with a 35V cone voltage and a peptide dependent collision voltage. All MRM assay development and transition selection was performed within the open-access Skyline (MacCoss Laboratory, Univ of Washington) software. Initially, up to five unique peptides were selected from each candidate protein based on average precursor ion intensity of those peptides which did not contain a missed cleavage, were not semi-tryptic, and did not contain a deamidation (N and Q) or oxidation (M). Five transitions for each precursor ion were selected based on 1) qualitative DDA discovery MS/MS data, 2) other discovery datasets for which the same peptide sequence was identified or 3) from the PeptideAtlas (www.PeptideAtlas.org) public repository. Initial MRM assay was performed on 1 ug of a healthy human control NPL pool, retention time scheduling (5 minute windows) was enabled, and the MRM method was optimized to choose three transitions from the two most robust peptides per protein.

Custom stable-isotope labeled (SIL) peptides (C13/N15 C-terminal Arg or Lys) were ordered (SpikeTide TQL product line, JPT Technologies, Berlin, Germany) and trypsin digested according to manufacturers recommended protocol (Supplementary Table S3).

SpikeTide SIL peptides were spiked into each individual digested NPL participant sample (input NPL protein mass was standardized based on Bradford assay) at one of four ratios relative to endogenous peptide (25, 50, 100, or 415 mol SIL peptide/1 ug of endogenous NPL peptide) based on MS signal response of SIL peptide alone injections. Each of the four patient cohorts (two H3N2 and two HRV) was run as individual run blocks and samples within a cohort were randomized in injection order across the cohort. Singlicate MRM assays were performed on spiked NPL samples with a target quantity of up to 1 ug on-column. Two independent strategies were employed to evaluate quantitative reproducibility between samples (FIG. 7A-FIG. 7C). The first was to spike five yeast ADH peptides (50fmol SIL peptide/ug of endogenous NPL protein) into each individual sample prior to (SIL labeled peptide) or after (non-SIL labeled) proteolytic digestion. The coefficient of variation in the ratio of the SIL to non-SIL peptides was then calculated across each of the four unique cohorts. The average coefficient of variation in these five yeast ADH peptides in the initial H3N2 #1 cohort (7.1%) was consistent with the H3N2 #2 (4.3%), HRV #1 (4.7%), and HRV #2 (5.4%) cohorts. The second strategy was to generate a quality control pools for each cohort with equal portions of each individual sample within that cohort. This was then run approximately every 12 hours across the entire acquisition window, including the first and last injection. The average coefficient of variation in ratio of the 56 SIL to non-SIL peptides in the H3N2 #1 derivation cohort (12.0%) was consistent with the H3N2 #2 (10.1%), HRV #1 (12.4%), and HRV #2 (13.0%) cohorts. These quality metrics demonstrate the reproducibility of the developed MRM assay and ensure no analytical artifacts contributed significantly to endogenous protein expression changes resulting from ARV infection.

Classification Model

Classification Errors

Supplementary Table S5 shows phenotypic data for individuals with incorrect NPL model classification at BL or T. Symptom status (Sx/Asx), shedding status (Shed +/−), GEA status (GEA +/−), infection call (Inf/Uninf), and NPL classification (+/−) are shown for each sample incorrectly classified by NPL model.

Pathway analysis. We repeated the classifier analysis using a more relaxed variable selection parameter (alpha=0.1 rather than 1.0) to provide a more extensive protein candidate list for functional annotation. The new classifier selected 30 of 47 peptides (17 unique proteins; Supplementary Table S3) and demonstrated nearly identical performance (0.8765 AUC, 75% TPR, and 97.46 TNR). Pathway association analysis was performed using DAVID 6.7 Functional Annotation Tool (Huang da, Sherman, & Lempicki, 2009) using UniProt accession identifiers and human background. Significant Gene Ontology biological processes containing members of this expanded classifier are shown in Supplementary Table S6.

Supplementary References

Dowell, J. A., Frost, D. C., Zhang, J., & Li, L. (2008). Comparison of two-dimensional fractionation techniques for shotgun proteomics. *Anal Chem*, 80(17), 6715-6723. doi:10.1021/ac8007994

Gilar, M., Olivova, P., Daly, A. E., & Gebler, J. C. (2005a). Orthogonality of separation in two-dimensional liquid chromatography. *Anal Chem*, 77(19), 6426-6434. doi:10.1021/ac050923i Gilar, M., Olivova, P., Daly, A. E., & Gebler, J. C. (2005b). Two-dimensional separation of peptides using RP-RP-HPLC system with different pH in first and second separation dimensions. *J Sep Sci*, 28(14), 1694-1703.

Huang da, W., Sherman, B. T., & Lempicki, R. A. (2009). Bioinformatics enrichment tools: paths toward the comprehensive functional analysis of large gene lists. *Nucleic Acids Res*, 37(1), 1-13. doi:10.1093/nar/gkn923

Huang, Y., Zaas, A. K., Rao, A., Dobigeon, N., Woolf, P. J., Veldman, T., . . . Hero, A. O., III. (2011). Temporal Dynamics of Host Molecular Responses Differentiate Symptomatic and Asymptomatic Influenza A Infection. *PLoS Genet*, 7(8), e1002234. doi:10.1371/journal.pgen.1002234

Jackson, G. G., Dowling, H. F., Spiesman, I. G., & Boand, A. V. (1958). Transmission of the common cold to volunteers under controlled conditions. I. The common cold as a clinical entity. *AMA Arch Intern Med*, 101(2), 267-278.

Liu, T.-Y., Burke, T., Park, L. P., Woods, C. W., Zaas, A. K., Ginsburg, G. S., & Hero, A. O. (2016). An individualized predictor of health and disease using paired reference and target samples. *BMC Bioinformatics*, 17(1), 1-15. doi:10.1186/s12859-016-0889-9

McClain, M. T., Nicholson, B. P., Park, L. P., Liu, T.-Y., Hero, A. O., Tsalik, E. L., . . . Woods, C. W. (2016). A Genomic Signature of Influenza Infection Shows Potential for Presymptomatic Detection, Guiding Early Therapy, and Monitoring Clinical Responses. *Open Forum Infectious Diseases*, 3(1). doi:10.1093/ofid/ofw007

Woods, C. W., McClain, M. T., Chen, M., Zaas, A. K., Nicholson, B. P., Varkey, J., . . . Ginsburg, G. S. (2013). A host transcriptional signature for presymptomatic detection of infection in humans exposed to influenza H1N1 or H3N2. *PLoS One*, 8(1), e52198. doi:10.1371/journal.pone.0052198

Zaas, A. K., Burke, T., Chen, M., McClain, M., Nicholson, B., Veldman, T., . . . Ginsburg, G. S. (2013). A Host-Based RT-PCR Gene Expression Signature to Identify Acute Respiratory Viral Infection. *Science Translational Medicine*, 5(203), 203ra126-203ra126. doi:10.1126/scitranslmed.3006280

Zaas, A. K., Chen, M., Varkey, J., Veldman, T., Hero, A. O., 3rd, Lucas, J., . . . Ginsburg, G. S. (2009). Gene expression signatures diagnose influenza and other symptomatic respiratory viral infections in humans. *Cell Host Microbe*, 6(3), 207-217. doi:10.1016/j.chom.2009.07.006

Any patents or publications mentioned in this specification are indicative of the levels of those skilled in the art to which the present disclosure pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present disclosure is well adapted to carry out the objects and obtain the ends and advantages mentioned, as well as those inherent therein. The present disclosure described herein is presently representative of preferred embodiments, are exemplary, and are not intended as limitations on the scope of the invention. Changes therein and other uses will occur to those skilled in the art which are encompassed within the spirit of the present disclosure as defined by the scope of the claims.

We claim:

1. A method of treating a subject having an acute respiratory viral (ARV) illness, wherein the ARV illness is caused by an influenza pathogen, said method comprising:
   (1) determining an etiology of the illness comprising:
      (a) obtaining a biological sample from the nasopharyngeal space or endotracheal site of the subject;
      (b) measuring on a platform expression levels of pre-determined set of proteins and/or peptides for the platform in said biological sample, wherein the pre-determined set of proteins and/or peptides comprises form 9 to 26 proteins and/or component peptides/epitopes listed in Table 2/2A or Table S4, and comprises A1AG1, TIG1, ANXA2, LCN15, ANGT, CFAB, TBA1B, CAYP1 and STAT, and wherein the measuring comprises detection and quantification of the proteins and/or component peptides/epitopes;
      (c) normalizing the expression levels to generate normalized expression values;
      (d) entering the normalized expression values into one or more acute respiratory virus (ARV) illness classifiers, said classifier(s) comprising pre-defined weighting values for each of the proteins and/or peptides for the platform; and
      (e) calculating an etiology probability for the ARV illness based upon said normalized expression values and said classifier(s),
      wherein said subject is determined to have the ARV illness; and
   (2) administering to the subject an appropriate treatment regimen,
   wherein said appropriate treatment regimen comprises an antiviral therapy.

2. The method of claim 1, wherein the obtaining the biological sample comprises a lavage, swab, curettage, or expectorate of the nasopharyngeal space or endotracheal site of the subject.

3. The method of claim 1, wherein the obtaining the biological sample comprises a nasopharyngeal lavage.

4. The method of claim 1, wherein the obtaining the biologic sample comprises capturing a nasal or respiratory spray onto a paper-based matrix for extraction or direct assay.

5. The method of claim 1, wherein the measuring comprises a quantitative mass spectrometry or an immunoassay.

6. The method of claim 5, wherein the platform comprises a quantitative mass spectrometry platform.

7. The method of claim 6, wherein the measuring comprises multiple reaction monitoring (MRM).

8. The method of claim 1, wherein the classifier(s) have a negative predictive value of greater than 90%.

9. The method of claim 1, wherein the entering comprises retrieving the classifier(s) from one or more databases.

10. The method of claim 1, wherein the determining the etiology of the illness further comprises determining a threshold for the determination of the etiology of the illness.

11. The method of claim 1, wherein the determining the etiology of the illness further comprises comparing the probability to pre-defined thresholds, cut-off values, or ranges of values that indicate an infection or a likelihood of infection.

12. The method of claim 1, wherein the determining the etiology of the illness further comprises generating a report assigning the subject a score indicating the probability of the presence and/or etiology of the ARV illness.

13. The method of claim 1, wherein the determining the etiology of the illness further comprises pathogen detection from said biological sample.

14. The method of claim 1, wherein the ARV illness is caused by an H3N2 influenza A pathogen.

15. The method of claim 1, wherein the pre-determined set of proteins and/or peptides further comprises at least one of A1AT, IC1, and/or APOA4.

16. A method of treating a subject having an acute respiratory viral (ARV) illness, wherein the ARV illness is caused by a human rhinovirus (HRV) pathogen, said method comprising:

(1) determining an etiology of the illness comprising:

(a) obtaining a biological sample from the nasopharyngeal space or endotracheal site of the subject;

(b) measuring on a platform expression levels of a pre-determined set of proteins and/or peptides for the platform in said biological sample, wherein the pre-determined set of proteins and/or peptides comprises from 9 to 26 proteins and/or component peptides/epitopes listed in Table 2/2A or Table S4, and comprises A1AG1, TIG 1, ANXA2, LCN15, ANGT, CFAB, TBA1B, CAYP1, and STAT, and wherein the measuring comprises detection and quantification of the proteins and/or component peptides/epitopes;

(c) normalizing the expression levels to generate normalized expression values;

(d) entering the normalized expression values into one or more ARV illness classifiers, said classifier(s) comprising pre-defined weighting values for each of the proteins and/or peptides for the platform; and (e) calculating an etiology probability for the ARV illness based upon said normalized expression values and said classifier(s), wherein said subject is determined to have the ARV illness; and (2) administering to the subject an appropriate treatment regimen, wherein said appropriate treatment regimen comprises one or more therapeutic agents capable of producing a reduction of symptoms associated with the ARV illness.

17. The method of claim 16, wherein the obtaining the biological sample comprises a lavage, swab, curettage, or expectorate of the nasopharyngeal space or endotracheal site of the subject.

18. The method of claim 16, wherein the obtaining the biologic sample comprises capturing a nasal or respiratory spray onto a paper-based matrix for extraction or direct assay.

19. The method of claim 16, wherein the measuring comprises a quantitative mass spectrometry or an immunoassay.

20. The method of claim 16, wherein the appropriate treatment regimen comprises a non-steroidal anti-inflammatory drug (NSAID), acetaminophen, an anti-histamine, a beta-agonist, an anti-tussive, or a CXCR2 antagonist.

\* \* \* \* \*

UNITED STATES PATENT AND TRADEMARK OFFICE
CERTIFICATE OF CORRECTION

PATENT NO. : 12,247,977 B2  
APPLICATION NO. : 16/483113  
DATED : March 11, 2025  
INVENTOR(S) : Burke et al.

Page 1 of 2

It is certified that error appears in the above-identified patent and that said Letters Patent is hereby corrected as shown below:

In the Specification

Column 3, Line 3: Please correct "test):" to read --test).--

Column 8, Line 40: Please insert a paragraph break between "belongs." and "One"

Column 10, Line 26: Please correct "ART-like" to read --ARI-like--

Column 10, Line 40: Please correct "TagMan®" to read --TaqMan®--

Column 16, Line 38: Please insert a paragraph break between "FIG. 5)." and "With"

Column 22, Line 57: Please insert a paragraph break between "herein." and "The"

Column 23, Lines 61-62: Please remove the paragraph break between "2014)." and "This"

Column 24, Line 40: Please correct "Can" to read --Carr--

Column 25, Lines 8-9: Please remove the paragraph break between "in" and "Supplementary"

Column 31, Line 59, Table 2A: Please correct "075223" to read --O75223--

Column 33, Lines 19-20: Please remove the paragraph break between "yielded an" and "AUROC"

Column 40, Lines 35-36: Please remove the paragraph break between "(2014)." and "The current"

Column 42, Line 38, Table S3: Please correct "NPI" to read --NPL--

Column 42, Line 41, Table S3: Please correct "> ±2 fold" to read --≥ ±2 fold--

Signed and Sealed this  
Twenty-sixth Day of August, 2025

Coke Morgan Stewart  
*Acting Director of the United States Patent and Trademark Office*

CERTIFICATE OF CORRECTION (continued)
U.S. Pat. No. 12,247,977 B2

Column 50, Line 66: Please correct "50 fluol" to read --50 fmol--

Column 51, Line 27: Please correct "5 μin" to read --5 μm--

Column 52, Lines 44-45: Please remove the paragraph break between "Table S3)." and "SpikeTide"

Column 52, Line 49: Please correct "mol" to read --fmol--

In the Claims

Column 75, Line 8, Claim 16: Please correct "9to 26proteins" to read --9 to 26 proteins--

Column 75, Line 10, Claim 16: Please correct "TIG 1" to read --TIG1--